(12) United States Patent
Cheng et al.

(10) Patent No.: US 8,703,197 B2
(45) Date of Patent: Apr. 22, 2014

(54) BRANCHED POLYAMINES FOR DELIVERY OF BIOLOGICALLY ACTIVE MATERIALS

(75) Inventors: Wei Cheng, Singapore (SG); Daniel J. Coady, San Jose, CA (US); Amanda C. Engler, San Jose, CA (US); James L. Hedrick, Pleasanton, CA (US); Pei Yun Teo, Singapore (SG); Chuan Yang, Singapore (SG); Yi Yan Yang, Singapore (SG)

(73) Assignees: International Business Machines Corporation, Armonk, NY (US); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/613,338

(22) Filed: Sep. 13, 2012

(65) Prior Publication Data
US 2014/0080215 A1  Mar. 20, 2014

(51) Int. Cl.
*A61K 47/30* (2006.01)
*C07D 321/00* (2006.01)
*C07H 21/00* (2006.01)

(52) U.S. Cl.
USPC ........... 424/486; 514/772; 536/23.1; 549/228

(58) Field of Classification Search
USPC ........... 424/486; 514/772; 536/23.1; 549/228
See application file for complete search history.

(56) References Cited

U.S. PATENT DOCUMENTS

| | | | |
|---|---|---|---|
| 6,696,038 B1 | 2/2004 | Mahato et al. | |
| 8,450,505 B2 * | 5/2013 | Hedrick | 549/228 |
| 2005/0059068 A1 | 3/2005 | Huang et al. | |
| 2007/0231392 A1 | 10/2007 | Wagner et al. | |
| 2009/0233359 A1 | 9/2009 | Kwon et al. | |
| 2010/0075420 A1 | 3/2010 | Saraf et al. | |
| 2010/0305281 A1 * | 12/2010 | Fujiwara et al. | 525/461 |
| 2011/0182996 A1 | 7/2011 | Fukushima et al. | |

FOREIGN PATENT DOCUMENTS

| | | |
|---|---|---|
| CN | 101575416 A | 11/2009 |
| CN | 101638484 A | 2/2010 |
| EP | 2172508 A1 | 4/2010 |
| EP | 1320386 B1 | 3/2011 |

OTHER PUBLICATIONS

He et al, Macromolecular Chem. and Phys. 211: 2366-2381, 2010.*
Pasquier et al, Biomacromolecules 8:2874-2882, 2007.*
Pasquier et al, Macromol. Biosci. 8:903-915, 2008.*
He et al, Macromolecular Chem. and Phys. 211:2366-2381, 2010.*
Luo et al, Biomaterials 32:9925-9939, 2011; avail. online Sep. 17, 2011.*
Doody, et al., "Characterizing the structure/function parameter space of hydrocarbon-conjugated branched polyethylenimine for DNA delivery in vitro," Journal of Controlled Release, 2006, 16, 227-237, Jul. 25, 2006.
Gabrielson, et al., "Efficient polyethylenimine-mediated gene delivery proceeds via a caveolar pathway in HeLa cells," Journal of Controlled Release 136 (2009) 54-61, Available online Feb. 13, 2009.
Goel, V., Thesis titled "Quat-Primer" polymers based on b-PEI and their application in composites, Aachen University, Germany, Jan. 26, 2010.
Griffiths, et al., "Derivatizing weak polyelectrolytes—Solution properties, self-aggregation, and association with anionic surfaces of hydrophobically modified poly(ethylene imine)," Journal of Colloid and Interface Science 314 (2007) 460-469; Available online Jun. 7, 2007.
Guo, et al., "Receptor-Targeted Gene Delivery Via Folate-Conjugated Polyethyleninnine," AAPS Pharmsci 1999; 1 (4); Published: Dec. 10, 1999.
Gusachenko, et al., "PEI—Cholesterol Conjugates with Different Levels of Modification" Journal of Biomaterials Science, Polymer Edition, 2009, 20:7-8, 1091-1110.
Huang, et al., "Inhibition of Bcl-2 expression by a novel tumor-specific RNA interference system increases chemosensitivity to 5-fluorouracil in Hela cells," Acta Pharmacologica Sinica Feb. 2006; 27 (2):242-248.
Livak, et al., "Analysis of Relative Gene Expression Data Using Real-Time Quantitative PCR and the 2-ΔΔCT Method", METHODS 25, 402-408 (2001).
Pasquier, et al., "Amphiphilic Branched Polymers as Antimicrobial Agents," Macromol. Biosci. 2008, 8, 903-915;published online: Sep. 10, 2008.
Pasquier, et al., "From Multifunctionalized Poly(ethylene imine)s toward Antimicrobial Coatings," Biomacromolecules, 2007, 8 (9), 2874-2882; Published on Web Aug. 3, 2007.
Pratt, et al., "Tagging alcohols with cyclic carbonate: a versatile equivalent of (meth)acrylate for ring-opening polymerization", ChemComm 2008, 114-116. First published on web Oct. 25, 2007.
Yang, et al., "The role of non-covalent interactions in anticancer drug loading and kinetic stability of polymeric micelles," Biomaterials 33 (2012) 2971-2979; Available online Jan. 13, 2012.
Zanta, et al., "In Vitro Gene Delivery to Hepatocytes with Galactosylated Polyethylenimine," Bioconjugate Chem. 1997, 8, 839-844; published Oct. 1, 1997.
Zhao, et al., "Starburst low-molecular weight polyethylenimine for efficient gene delivery," J Biomed Mater Res Part A 2012:100A:134-140; Published online Oct. 14, 2011.
Zintchenko, et al., "Simple Modifications of Branched PEI Lead to Highly Efficient siRNA Carriers with Low Toxicity," Bioconjugate Chem. 2008, 19, 1448-1455; published on web Jun. 14, 2008.
KIPO, International search report and written opinion, PCT/US2013/057976; mailed Dec. 19, 2013.

* cited by examiner

*Primary Examiner* — Kevin Hill
(74) *Attorney, Agent, or Firm* — Michael R. Roberts

(57) ABSTRACT

A branched polyamine comprises about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of formula (2):

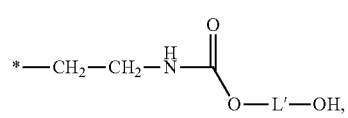

wherein (n'+q) is a number equal to about 45 to about 70, the starred bond of formula (2) is linked to a backbone nitrogen of the branched polyamine, L' is a divalent radical comprising 3 to 30 carbons, and q/(n'+q)×100% equals about 9% to about 47%.

27 Claims, 33 Drawing Sheets

BRANCHED POLYAMINES FOR DELIVERY OF BIOLOGICALLY ACTIVE MATERIALS

This invention was made under a joint research agreement between International Business Machines Corporation and the Agency For Science, Technology and Research.

Incorporated herein by reference is the Sequence Listing contained in the text file named 1361338 Sequence Listing ST25.txt created Oct. 10, 2012, having a size of 2 kilobytes.

BACKGROUND

The invention relates to branched polyamines for delivery of biologically active materials, and more specifically, to carbamate functionalized branched polyethylenimines comprising hydrophobic carbamate end groups for gene delivery.

Nucleic acid-based therapy holds great promise in treating human diseases. In principle, not only can faulty and defective genes be corrected and replaced by functional ones, but redundant gene expression could also be repressed to normal level by the use of RNA interference. In general, there are two major types of gene delivery vectors, viral and non-viral vectors. Although viral vectors have superior transduction capabilities, the immunogenic and oncogenic potential of viral vectors limits their clinical applications. To circumvent this problem, a number of non-viral gene delivery systems have been reported, which include (1) complex of nucleic acids with various cationic molecules including lipids, polymers and peptides and (2) conjugation of nucleic acids with natural ligands such as, for example, cholesterol and cell penetration peptide. Non-viral gene delivery vectors are receiving increasing attention due to biosafety, low production cost, ease of transportation and storage, reproducibility, and tunable functionalities for targeting specific cell types.

Among the various types of non-viral vectors branched polyethylenimine (bPEI), which contains primary, secondary and tertiary amine groups, provides high gene transfection efficiency in vitro. In particular, bPEI having a weight average molecular weight (Mw) of about 25 kDa and number average molecular weight (Mn) of about 10 kDa, referred to herein as bPEI-25, is regarded as an industry standard. bPEI-25 has a high cationic charge density at physiological pH, where about 20% of amine groups (i.e. primary amines) of bPEI-25 are protonated. This allows bPEI-25 to interact electrostatically with negatively charged nucleic acids over a broad pH range and to complex them into nanoparticles. Once bPEI-25/nucleic acid nanocomplexes are internalized by the cells, the secondary and tertiary amines facilitate the release of the nucleic acids from the endosomes through the "proton sponge effect". In the case of deoxyribonucleic acid (DNA), the uptake of the released nucleic acids into the nucleus confers high gene transfer efficiency.

Despite its high gene transfection efficiency, the net positive charge of bPEI-25 has major drawbacks concerning toxicity, aggregation and undesired non-specific interactions of bPEI-25/nucleic acid complexes with cellular and non-cellular components, particular in vivo. Adverse effects include liver necrosis, adhesion of aggregated platelets and shock after systemic injection of higher doses.

In view of the cytotoxic issues faced by bPEI-25, low molecular weight branched polyethylenimine (Mw about 2.0 kDa, Mn about 1.8 kDa, referred to herein as bPEI-2) has gained interest as well due to its favorable cytotoxicity profile. Low molecular weight enables bPEI-2 to be excreted from the kidneys when used for in vivo therapeutic purposes. However, the major disadvantage of bPEI-2 is its inefficient transfection ability rendering it inadequate for use as a gene transfection vector.

Thus, an ongoing need exists to develop more efficient and less cytotoxic polyethylenimine derivatives for delivery of biologically active materials.

SUMMARY

Accordingly, a branched polyamine is disclosed, comprising:

about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of formula (2):

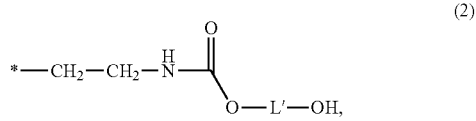

wherein:
(n'+q) is a number equal to about 45 to about 70,
the starred bond of formula (2) is linked to a backbone nitrogen of the branched polyamine,
L' is a divalent radical comprising 3 to 30 carbons, and
q/(n'+q)×100% equals about 9% to about 47%.

Also disclosed is a branched polyamine comprising:
about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of the formula (4):

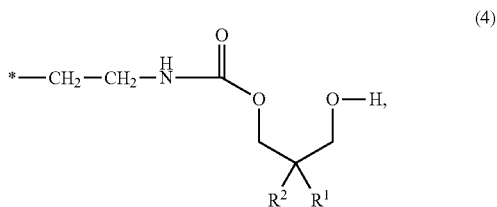

wherein
the starred bond of formula (4) is linked to a backbone nitrogen of the branched polyamine,
$R^1$ is hydrogen, methyl, or ethyl,
$R^2$ is hydrogen or a monovalent radical comprising 1 to 27 carbons,
(n'+q) is a number equal to about 45 to about 70, and
q/(n'+q)×100% equals about 9% to about 47%.

Further disclosed is a method comprising:
treating a branched first polymer comprising about 45 to about 70 primary amine groups, a plurality of secondary amine groups, and a plurality of tertiary amine groups with a cyclic carbonate monomer without polymerizing the cyclic carbonate monomer, thereby forming a branched polyamine comprising i) about 45 to about 70 backbone tertiary amine groups, ii) about 90 to about 140 backbone secondary amine groups, iii) a positive number n' greater than 0 of backbone terminating primary amine groups, and iv) a positive number q greater than 0 of backbone terminating carbamate groups of formula (2):

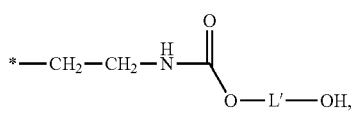

(2)

wherein:

(n'+q) is a number equal to about 45 to about 70, the starred bond of formula (2) is linked to a backbone nitrogen of the branched polyamine, L' is a divalent radical comprising 3 to 30 carbons, and $q/(n'+q) \times 100\%$ equals about 9% to about 47%.

Also disclosed is a complex comprising:

a gene; and a branched polyamine comprising about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of formula (2):

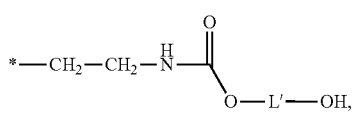

(2)

wherein:

(n'+q) is a number equal to about 45 to about 70, the starred bond of formula (2) is linked to a backbone nitrogen of the branched polyamine, L' is a divalent linking group comprising 3 to 30 carbons, and $q/(n'+q) \times 100\%$ equals about 9% to about 47%.

Also disclosed is a method of treating a cell comprising contacting the cell with the above-described complex.

Further disclosed is a branched polyamine having a structure according to formula (5):

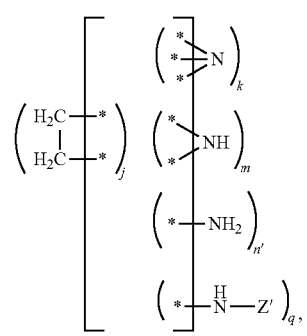

(5)

wherein j, k, m, n' and q represent molar amounts greater than 0, j has a value about 185 to about 280, k has a value of about 45 to about 70, m has a value of about 90 to about 140, (n'+q) has a value of about 45 to about 70, and $q/(n'+q) \times 100\%$ has a value of about 9% to about 47%, and each Z' is an independent moiety selected from the group consisting of

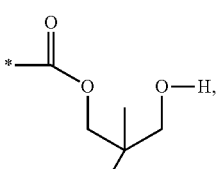
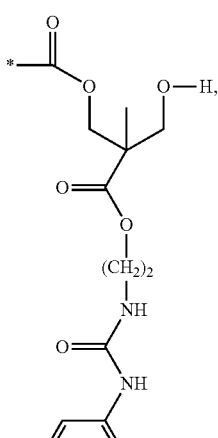
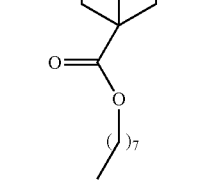
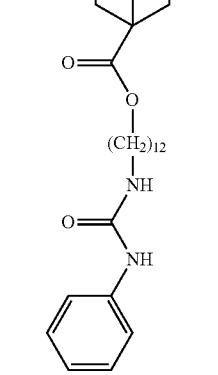
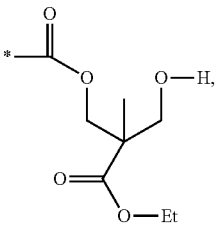
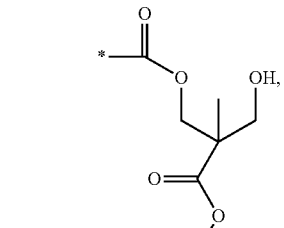
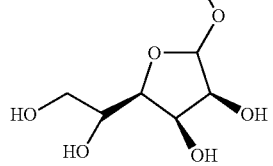

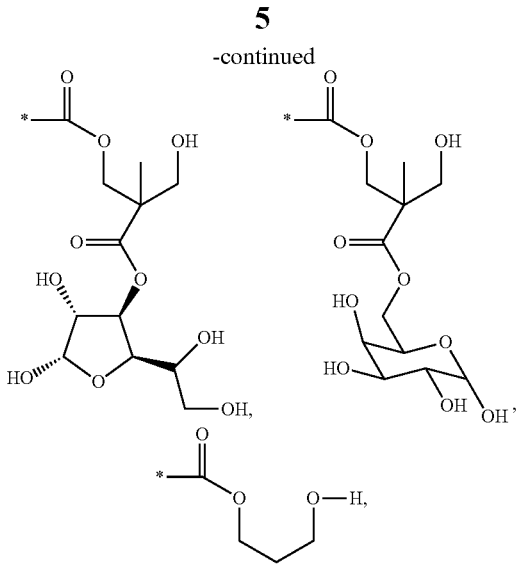

and combinations thereof.

The above-described and other features and advantages of the present invention will be appreciated and understood by those skilled in the art from the following detailed description, drawings, and appended claims.

DETAILED DESCRIPTION

Figure 1:
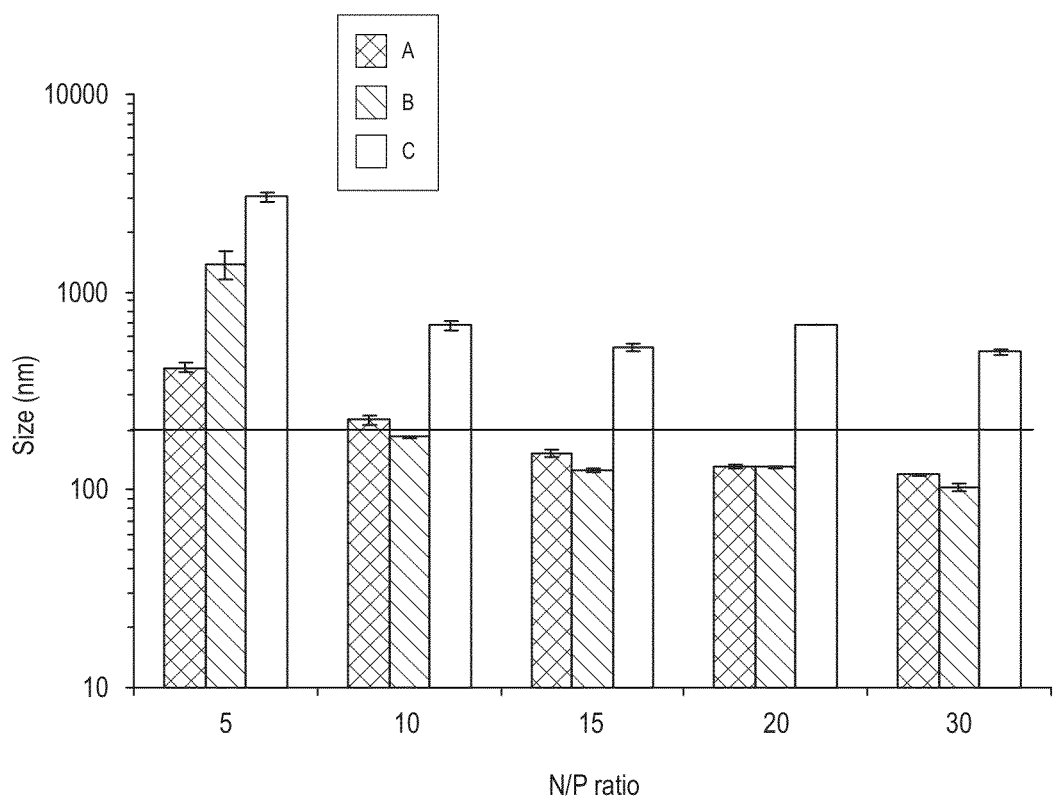
FIG. 1 is a bar graph showing particle sizes of green fluorescent protein (GFP) reporter gene complexes prepared with carbamate functionalized branched polyethylenimine polymers A, B, and C. A, B, and C were prepared from a commercially available bPEI-25. The gene complexes were prepared at N/P 5 to 30. "N/P" refers to the molar ratio of nitrogen of the carbamate functionalized bPEI-25 polymer to phosphorus of the gene, and is indicative of the net charge of the carbamate functionalized bPEI-25/gene complex. A control gene complex of bPEI-25 was prepared at N/P 10 (not shown), which had an average particle diameter of about 84 nm and a zeta potential of about 22 mV.

Disclosed are branched polyamines for delivery of biologically active materials including genes, proteins and/or drugs. The branched polyamines are preferably prepared by reacting one or more hydrophobic cyclic carbonate compounds with a branched polyethylenimine (bPEI) comprising about 45 to about 70 primary amine groups, a plurality of secondary amine groups, and a plurality of tertiary amine groups. For clarity, the branched polyethylenimine starting material for the carbamate forming reaction with the cyclic carbonate monomer is referred to in the following description as a non-modified branched polyethylenimine ("non-modified bPEI"). The product of the reaction is a carbamate functionalized bPEI polymer referred to as a modified branched polyethylenimine ("modified bPEI). The non-modified bPEI can have a number average molecular weight (Mn) of about 8000 to about 12000 and a weight average molecular weight (Mw) of about 8000 to about 30000. More specific branched polyamines are formed by treating bPEI-25 (referred to as "non-modified bPEI-25") with a cyclic carbonate compound. The resulting branched polyamines, which are carbamate functionalized bPEI-25 polymers, are referred to as "modified bPEI-25" polymers. It should be understood that branched amine-containing polymers other than branched polyethylenimines can potentially be used for the carbamate forming reaction (e.g., dendritic amine polymers having about 45 to about 70 primary amine groups, a plurality of secondary amine groups, and a plurality of tertiary amine groups).

The branched polyamines are capable of acting as carriers for genes in a process of gene transfection. As examples, the modified bPEI polymers can be more efficient gene transfection agents in HepG2 cells (cancerous human liver cells), SK-OV-3 cells (cancerous human ovarian cells), and/or mHSC (human mesenchymal stem cells) compared to the gene complex of the corresponding non-modified bPEI. The modified bPEI/gene complexes can also be less cytotoxic at N/P ratios 20 to 50 compared to the gene complex of the corresponding non-modified bPEI, which can be highly cytotoxic above N/P 20. Additionally, cells transfected with a complex prepared with a modified bPEI and luciferase reporter gene can express the luciferase gene at a level comparable to or greater than a luciferase complex of the corresponding non-modified bPEI.

The non-modified bPEI contains a plurality of divalent ethylene groups (*—CH$_2$CH$_2$—*), a plurality of backbone tertiary amines, a plurality of backbone secondary amines, and a plurality of backbone terminating primary amine groups. More specifically, the non-modified bPEI has about 185 to about 280 ethylene groups, about 45 to about 70 backbone tertiary amine groups, about 90 to about 140 backbone secondary amine groups, about 45 to about 70 backbone terminating primary amine groups, based on the range of Mn and an average ethylenimine subunit having a molecular weight of 43. The backbone end units of the non-modified bPEI contain the primary amine groups.

Thus, the non-modified bPEI has a structure consisting essentially of about 45 to about 70 primary ethylenimine repeat units of structure

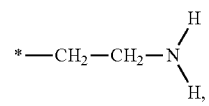

about 90 to about 140 secondary ethylenimine repeat units of structure:

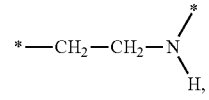

and
about 45 to about 70 tertiary ethylenimine repeat units of structure:

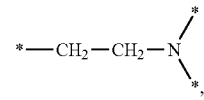

excluding any hydrosalt of the foregoing repeat units that may be present. Each starred bond in the above repeat units represents an attachment point to another repeat unit of the non-modified bPEI.

The non-modified bPEI is also represented herein by formula (1):

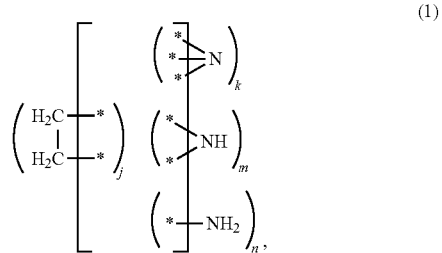

(1)

wherein j, k, m, and n represent moles of the respective independent functional groups of the non-modified bPEI structure, j has a value of about 185 to about 280, k has a value of about 45 to about 70, m has a value of about 90 to about 140, and n has a value of about 45 to about 70. It should be understood by the notation of formula (1) that each set of parentheses ( ) beginning inside the square brackets [ ] and ending outside the square brackets encloses an independent functional group of the non-modified bPEI, not a polymer chain. The starred bonds represent attachment points to starred bonds on the opposite side of the brackets. Thus each nitrogen on the right side of the square brackets is bonded to a carbon of an ethylene group on the left side of the square brackets.

As an example, the above-mentioned commercially available branched polyethylenimine, bPEI-25, has a weight average molecular weight (Mw) of 25000, a number average molecular weight (Mn) of about 10000, and contains an average of 58 backbone tertiary amine groups, 116 backbone secondary amine groups, 58 backbone terminating primary amine groups, and 233 ethylene groups (based on Mn and an average ethylenimine repeat unit molecular weight equal to 43). In this instance, j=233, k=58, m=116, and n=58. This material is also referred to herein as "non-modified bPEI-25."

As another example, the above-mentioned commercially available branched polyethylenimine, bPEI-2, has a weight average molecular weight (Mw) of 2000, a number average molecular weight (Mn) of about 1800, and contains an average of 10 backbone tertiary amine groups, 20 backbone secondary amine groups, 10 backbone terminating primary amine groups, and 35 ethylene groups (based on Mn and an average ethylenimine repeat unit molecular weight equal to 43). In this instance, j=35, k=10, m=20, and n=10. This material is referred to herein as bPEI-2 or as "non-modified bPEI-2."

The backbone terminating primary amine groups of the non-modified bPEI undergo a carbamate forming ring opening reaction with the cyclic carbonate compound, thereby forming a branched polyamine. The ring opening reaction preferably occurs with minimal polymerization or no polymerization of the cyclic carbonate compound.

The branched polyamines comprise about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of the formula (2):

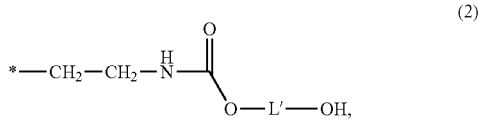

(2)

wherein the starred bond of formula (2) is linked to a backbone nitrogen of the branched polyamine, q/(n'+q)×100% equals about 9% to about 47%, (n'+q) is a number equal to about 45 to about 70, and L' is a divalent linking group comprising 3 to 30 carbons.

More specific branched polyamines have a structure comprising:
i) a positive number n' greater than 0 of backbone terminating primary ethylenimine repeat units of structure:

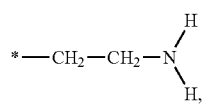

ii) about 90 to about 140 backbone secondary ethylenimine repeat units of structure:

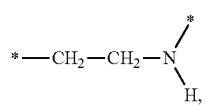

iii) about 45 to about 70 backbone tertiary ethylenimine repeat units of structure:

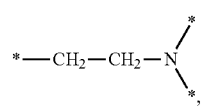

and
iv) a positive number q greater than 0 of backbone terminating carbamate end groups of formula (2):

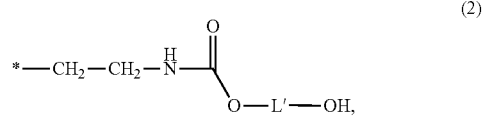

(2)

wherein each of the starred bonds in the above structures represents an attachment point to another repeat unit of the branched polyamine, q/(n'+q)×100% equals about 9% to about 47%, (n'+q) is a number equal to about 45 to about 70, and L' is a divalent linking group comprising 3 to 30 carbons. The starred bond of formula (2) is linked to a backbone nitrogen of the branched polyamine. In an embodiment, the branched polyamine consists essentially of the above-described primary ethylenimine repeat units, secondary ethylenimine repeat units, tertiary ethylenimine repeat units, and carbamate end groups. In another embodiment, the branched polyamine is a carbamate functionalized bPEI-25 (i.e., modified bPEI-25 polymer). In another embodiment, L' is a non-charged group. In another embodiment, the branched polyamine comprises no quaternary amine group.

The branched polyamines can also be represented by formula (3):

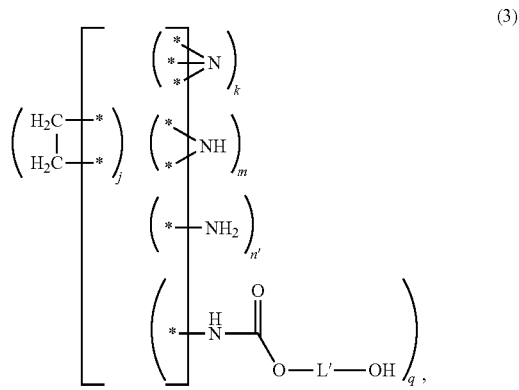

(3)

wherein j, k, m, n' and q represent moles greater than 0 of each of the independent functional groups enclosed in parentheses in formula (3), j has a value of about 185 to about 280, k has a value of about 45 to about 70, m has a value of about 90 to about 140, (n'+q) has a value of about 45 to about 70, and q/(n'+q)×100% has a value of about 9% to about 47%. The notation using the brackets and parentheses has the same meaning as described above for formula (1). L' is a divalent linking group comprising 3 to 30 carbons.

In a method of preparing a branched polyamine, the reaction mixture comprises the cyclic carbonate compound and a non-modified bPEI, and the cyclic carbonate compound is present in an amount less than 50 mol % based on total moles of primary amine groups of the non-modified bPEI. Thus, at least 50% of the primary amine groups of the non-modified bPEI remain in the branched polyamine. In an embodiment, q/(n'+q)×100% of formula (3) equals about 9% to about 25%. In an even more specific embodiment, q/(n'+q)×100% of formula (3) equals about 9% to about 12%.

Each backbone tertiary amine group, backbone secondary amine group and/or backbone terminating primary amine group of the branched polyamine can be present as a free base or as a hydrosalt (e.g., a positive charged protonated amine associated with a negative charged counterion such as, for example, hydroxide, chloride, acetate, and/or sulfonate).

Another more specific branched polyamine comprises about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of the formula (4):

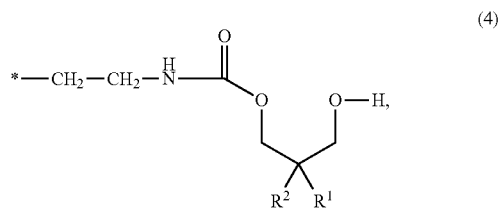

(4)

The starred bond of formula (4) is linked to a backbone nitrogen of the branched polyamine. $R^1$ is hydrogen, methyl, or ethyl. $R^2$ is hydrogen or a monovalent radical comprising 1 to 27 carbons. The value of (n'+q) is a number equal to about 45 to about 70, and q/(n'+q)×100% equals about 9% to about 47%.

Another more specific branched polyamine comprises:
i) a positive number n' greater than 0 of backbone terminating primary ethylenimine repeat units of structure:

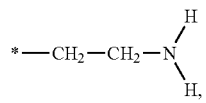

ii) about 90 to about 140 backbone secondary ethylenimine repeat units of structure:

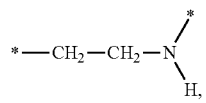

iii) about 45 to about 70 backbone tertiary ethylenimine repeat units of structure:

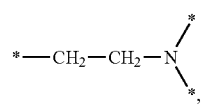

and
iv) a positive number q greater than 0 of backbone terminating carbamate end groups of formula (4):

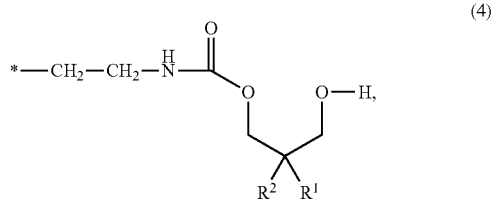

(4)

wherein each of the starred bonds is linked to another repeat unit of the branched polyamine, $R^1$ is hydrogen, methyl, or ethyl, and $R^2$ is hydrogen or a group comprising 1 to 27 carbons, (n'+q) has a value of about 45 to about 70, and q/(n'+q)×100% has a value of about 9% to about 47%. In an embodiment, the branched polyamine consists essentially of the primary ethylenimine repeat units, secondary ethylenimine repeat units, tertiary ethylenimine repeat units, and carbamate end groups. In another embodiment, the branched polyamine is a carbamate functionalized bPEI-25.

In an embodiment, $R^2$ of formula (4) is an ester *—C(=O)OR$^3$, wherein $R^3$ comprises 1 to 26 carbons.

$R^3$ can comprise a sugar moiety. Exemplary $R^3$ groups comprising sugar moieties include esters of mannose, galactose, and/or glucose.

$R^3$ can comprise a monovalent hydrocarbon radical comprising 1 to 26 carbons. Exemplary monovalent hydrocarbon radicals include methyl, ethyl, propyl, butyl, pentyl, hexyl, septyl, octyl, nonyl, decyl, undecyl and dodecyl groups. The monovalent hydrocarbon radical can be branched or straight chain.

Other $R^3$ groups include benzyl esters and esters bearing a urea group.

The branched polyamine can have a number average molecular weight (Mn) of about 8500 to about 15000. The branched polyamine can have a weight average molecular weight (Mw) of about 8500 to about 35000.

The carbamate group can optionally comprise one or more protecting groups. In these instances, the method of forming a branched polyamine can further comprise selectively removing the one or more protecting groups.

Exemplary cyclic carbonate monomers include the compounds of Table 1:

TABLE 1

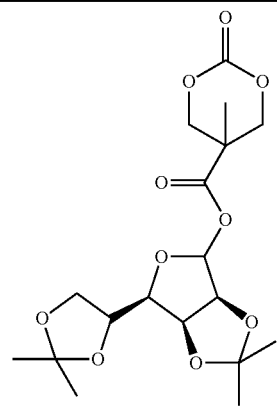

MTC-IPMAN

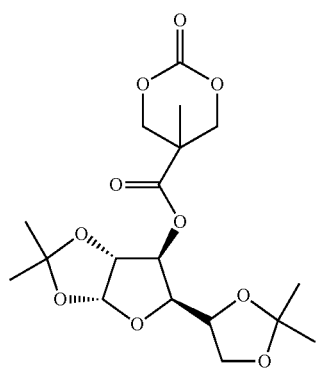

MTC-IPGLU

TABLE 1-continued
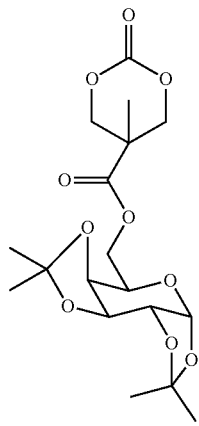
MTC-IPGAL
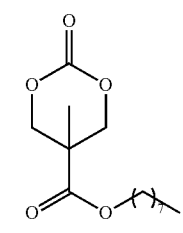
MTC-C8
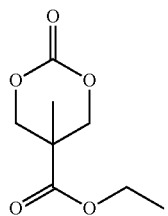
MTC-C2
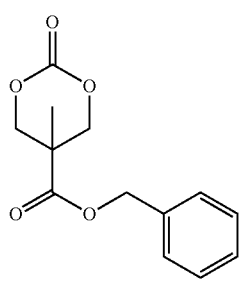
MTC-Bn
TABLE 1-continued
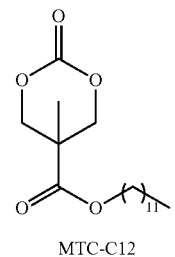
MTC-C12
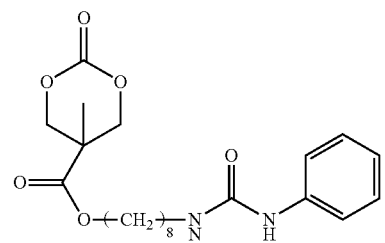
MTC-PUC8
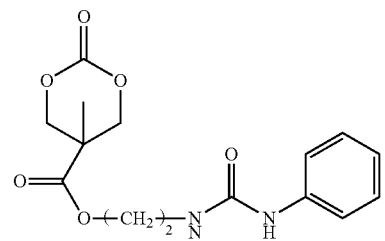
MTC-PUC2
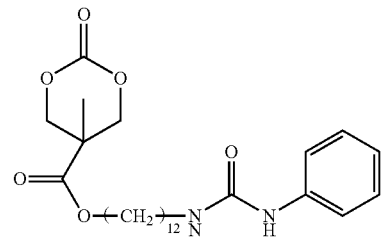
MTC-PUC12
Additional examples of cyclic carbonate monomers include the compounds of Table 2.
TABLE 2
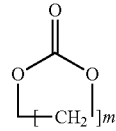
m = 1: Trimethylene carbonate (TMC)
m = 2: Tetramethylene carbonate (TEMC)
m = 3: Pentamethylene carbonate (PMC)

TABLE 2-continued
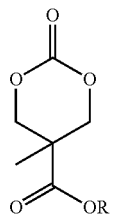
R = hydrogen (MTCOH)
R = methyl (MTCOMe)
R = t-butyl (MTCOtBu)
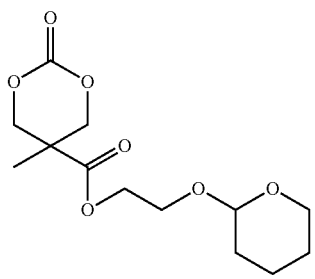 [SMILES: CC1(C(=O)OCCOC2CCCCO2)COC(=O)OC1]
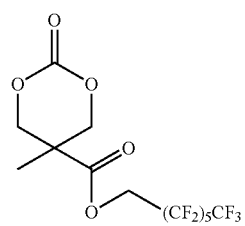
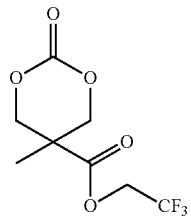 [SMILES: CC1(C(=O)OCC(F)(F)F)COC(=O)OC1]
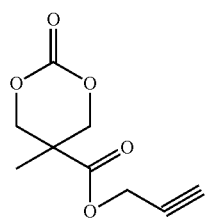
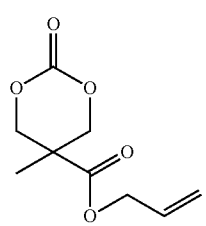
TABLE 2-continued
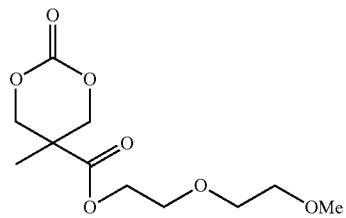 [SMILES: COCCOCCOC(=O)C1(C)COC(=O)OC1]
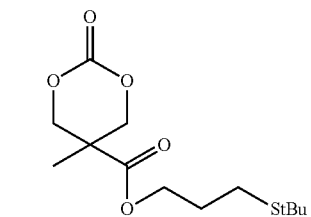
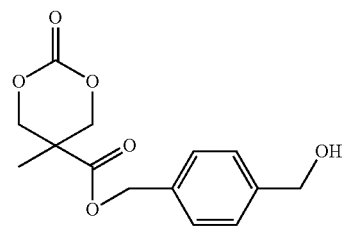 [SMILES: CC1(C(=O)OCc2ccc(CO)cc2)COC(=O)OC1]
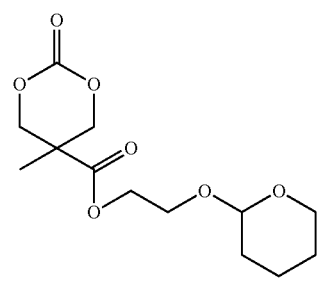 [SMILES: CC1(C(=O)OCCOC2CCCCO2)COC(=O)OC1]
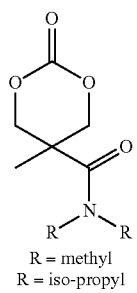
R = methyl
R = iso-propyl
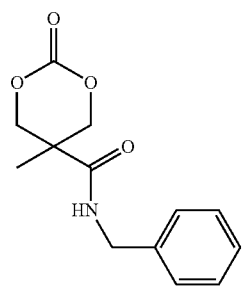 [SMILES: CC1(C(=O)NCc2ccccc2)COC(=O)OC1]

TABLE 2-continued

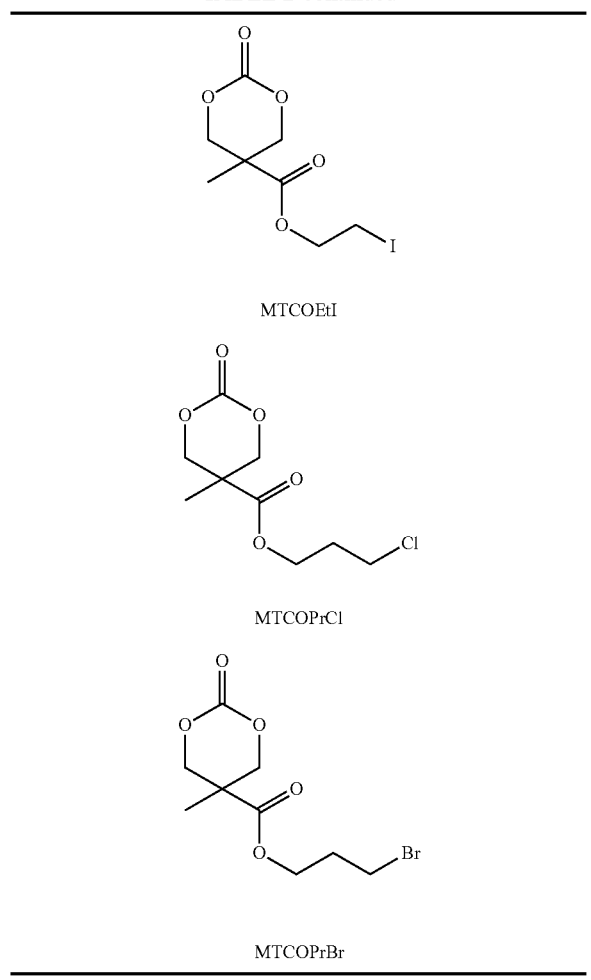

MTCOEtI

MTCOPrCl

MTCOPrBr

The cyclic carbonate monomers can be used singularly or in combination.

Still more specific branched polyamines have a structure according to formula (5):

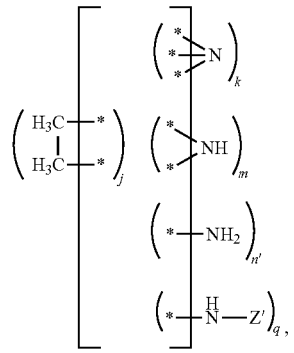

(5)

wherein j, k, m, n' and q represent molar amounts greater than 0, j has a value of about 35 to about 60, k has a value of about 8 to about 20, m has a value of about 15 to about 40, (n'+q) has a value of about 45 to about 70, (n'+q)/q×100% has a value of about 9% to about 47%, and each Z' is a moiety independently selected from the group consisting of

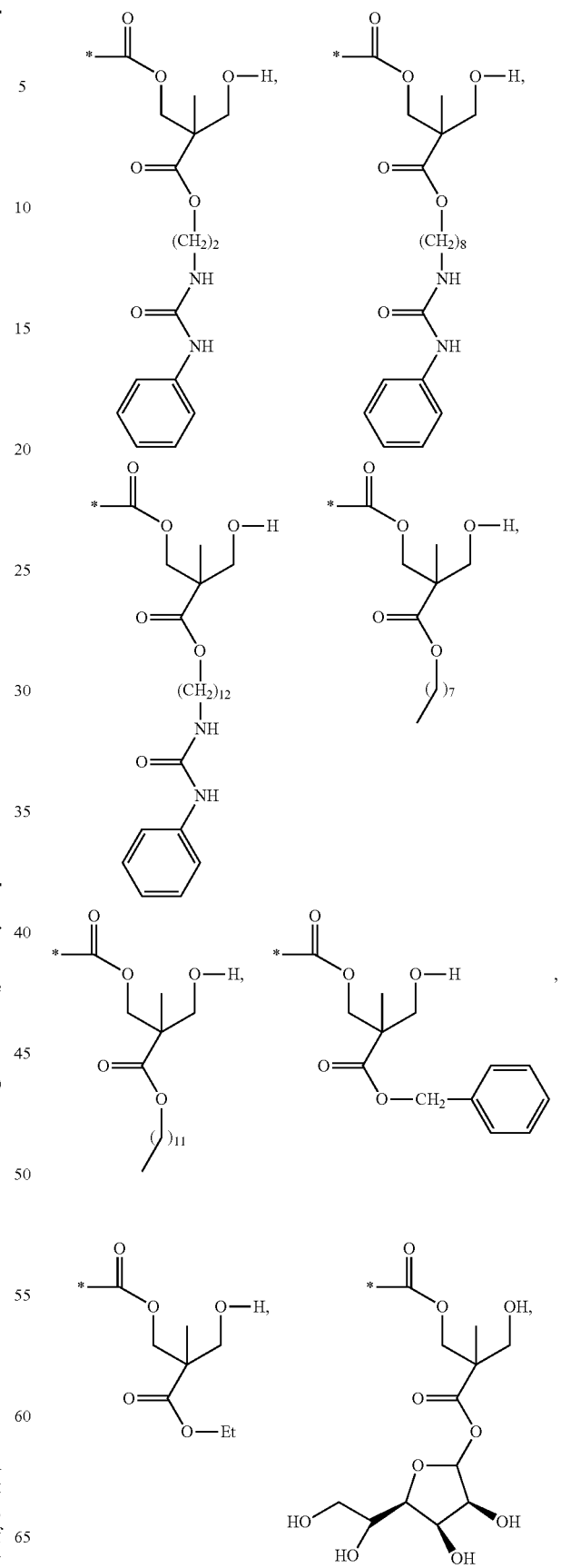

-continued

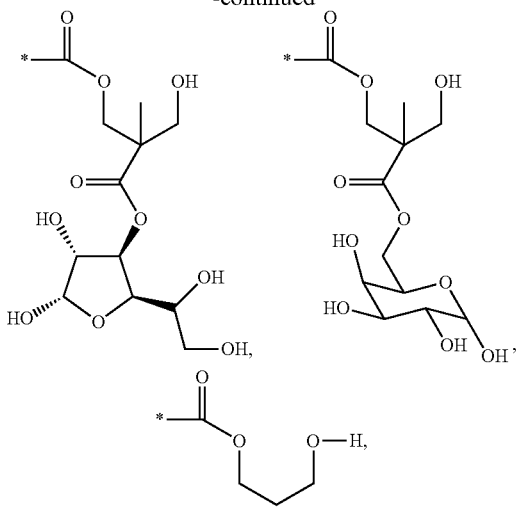

and combinations thereof.

Also disclosed is a complex comprising a gene and an above-described branched polyamine. Further disclosed is a method of treating a cell, comprising contacting the cell with the complex.

The following examples demonstrate a facile method of introducing multiple mannose, galactose and glucose molecules, and hydrophobic groups such as trimethylene carbonate, and esters bearing aliphatic hydrocarbon, benzyl, aromatic urea groups into a non-modified bPEI-25 (Mw 25 kDa, Mn 10 kDa), thereby forming branched polyamines (modified bPEI-25 polymers). The cyclic carbonate can be ring opened with or without organic catalyst (1,8-diazabicycloundec-7-ene, DBU). Without DBU, a carbamate with a primary alcohol can form. With DBU, a carbamate with a primary alcohol can also form when the primary amine groups are present in excess of the cyclic carbonate (e.g., using cyclic carbonate and non-modified bPEI-25 in a molar ratio of 25:1 and 8:1, respectively, because there are about 58 primary amine groups in each non-modified bPEI-25 macromolecule). However, at cyclic carbonate to non-modified bPEI-25 molar ratio of 75:1, a modified bPEI-25 comprising poly (carbonate) chains linked to the primary amine sites of the non-modified bPEI-25 is likely.

DNA binding, particle size, zeta potential, and gene expression properties of various modified bPEI-25/gene complexes are described. The gene transfection efficiency and cytotoxicity of the complexes in HepG2 (human liver carcinoma cell line) and SK-OV-3 (human ovarian carcinoma cell line) and human mesenchymal stem cells were investigated and compared with the non-modified bPEI-25 by using luciferase reporter gene and green fluorescent protein (GFP) reporter gene. To further demonstrate the ability of the mannose-modified bPEI-25 polymers to deliver siRNA, siRNA targeting Bcl-2, a protein postulated to block the release of cytochrome C after the initiation of apoptosis and often overexpressed in cancer cells, was used and delivered into human epithelial carcinoma HeLa cell line. Bcl-2 mRNA expression levels in the cells were measured using real-time reverse-transcription polymerase-chain reaction (RT-PCR) after treatment with mannose-modified bPEI-25/Bcl-2 siRNA. Viability of the HeLa cells was analyzed by MTT assay after incubation with the siRNA complexes.

EXAMPLES

Materials used in the following examples are listed in Table 3.

TABLE 3

| ABBREVIATION | DESCRIPTION | SUPPLIER |
|---|---|---|
| DBU | 1,8-Diazabicyclo[5,4,0]undec-7-ene | Aldrich |
| bPEI-25 | Branched Polyethylenimine, Mw = 25000, Mn = 10000, 58 primary amine groups, 116 secondary amine groups and 58 tertiary amine groups; also referred to as non-modified bPEI-25. | Aldrich |
| bPEI-2 | Branched Polyethylenimine, Mw = 2000, Mn = 1800, 10 primary amine groups, 20 secondary amine groups, and 10 tertiary amine groups; also referred to as non-modified bPEI-2. | Aldrich |
| MTT | 1-(4,5-Dimethylthiazol-2-yl)-3,5-Diphenylformazan | Aldrich |
| IPMAN | 2,3;5,6-Di-O-Isopropylidene-D-Mannofuranose | Aldrich |
| IPGAL | 1,2;3,4-Di-O-Isopropylidene-D-Galactopyranose | Aldrich |
| IPGLU | 1,2;5,6-Di-O-Isopropylidene-D-Glucofuranose | Aldrich |
| | 2-Amino-1-Ethanol | Aldrich |
| | 8-Amino-1-Octanol | Aldrich |
| | 12-Amino-1-Dodecanol | Aldrich |
| TMC | Trimethylene Carbonate | Aldrich |
| Bis-MPA | 2,2-Dimethylol-Propionic Acid | Aldrich |
| DBU | 1,8-Diazabicyclo[5,4,0]Undec-7-Ene | Aldrich |
| PFC | Bis-(Pentafluorophenyl) Carbonate | Aldrich |

Herein, Mn is the number average molecular weight, Mw is the weight average molecular weight, and MW is the molecular weight of one molecule.

1,8-Diazabicyclo[5,4,0]undec-7-ene (DBU) was stirred over $CaH_2$ and vacuum distilled before being transferred to a glove box. Branched polyethylenimines having a weight average molecular weight of 25 kDa (bPEI-25) and 1.8 kDa (bPEI-2), 1-(4,5-dimethylthiazol-2-yl)-3,5-diphenylformazan (MTT) for cytotoxicity assay, and other reagents for polymer synthesis were commercially available from Aldrich and used without any other purification unless otherwise noted. Bcl-2 targeted siRNA duplex (sequence: sense 5'-GUA CAU CCA UUA UAA GCU G (SEQ ID NO:1); antisense 5'-CAG CUU AUA AUG GAU GUA C (SEQ ID NO:2)), β-Actin targeted siRNA duplex, and scramble siRNA (negative control) was purchased from Dharmacon (U.S.A). Luciferase substrate and 5× lysis buffer was purchased from Promega (Singapore). GFP-reporter gene (encoding a red-shifted variant of wild-type GFP driven by the cytomegalovirus promoter) and luciferase-reporter gene (encoding the 6.4 kb firefly luciferase gene driven by the cytomegalovirus promoter) were obtained from Clontech (U.S.A.) and Carl Wheeler, Vical (U.S.A.) respectively. The BCA protein assay kit was from Pierce. HepG2 (liver), SK-OV-3 (ovarian) and HeLa (cervical) human cancer cell lines were purchased from ATCC (U.S.A.).

MTC-OH can be prepared by the method of R. C. Pratt, et al., Chemical Communications, 2008, 114-116.

Preparation of MTC-C6H5 (MW 326.2).

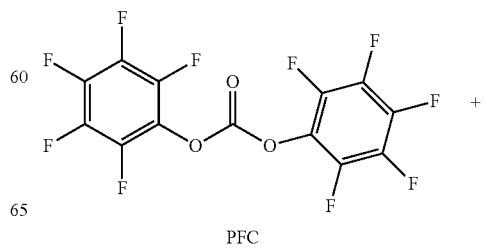

PFC +

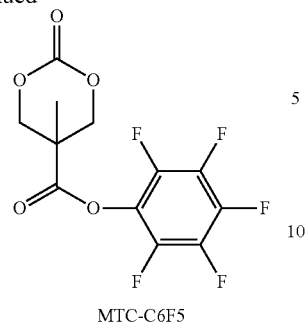

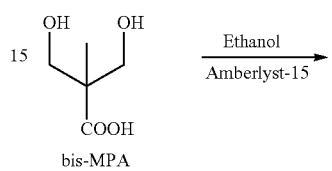

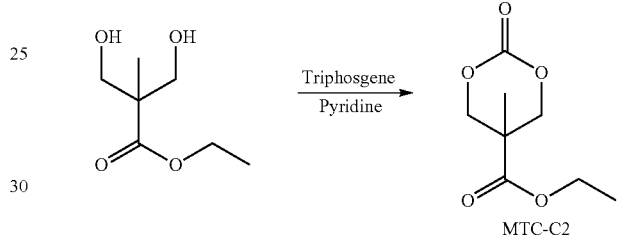

A 100 mL round bottom flask was charged with bis-MPA, (7), (5.00 g, 37 mmol, MW 134.1), bis-(pentafluorophenol) carbonate (PFC, 31.00 g, 78 mmol, MW 394.1), and CsF (2.5 g, 16.4 mmol) rinsed with 70 mls of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}$F NMR of pentafluorophenol and a single peak in the GCMS with a mass of 184. The filtrate was extracted with sodium bicarbonate, water and was dried with $MgSO_4$. The solvent was evaporated in vacuo and the product was recrystallized (ethyl acetate/hexane mixture) to give MTC-C6F5 as a white crystalline powder. The GCMS had a single peak with mass of 326 g/mol. The calculated molecular weight for $C_{12}H_7F_5O_5$ was consistent with the assigned structure. $^1$H-NMR (400 MHz in $CDCl_3$): delta 4.85 (d, J=10.8 Hz, 2H, $CH_aH_b$), 4.85 (d, J=10.8 Hz, 2H, $CH_aH_b$), 1.55 (s, 3H, $CCH_3$).

I. Synthesis Of Monomers

Example 1

Preparation of MTC-Cl (MW 178.6)

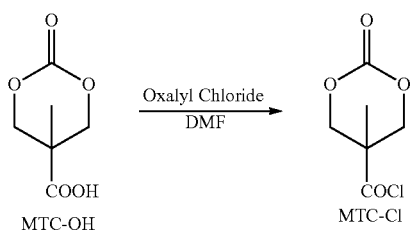

A solution of oxalyl chloride (2.48 mL, 19.0 mmol) in 50 mL of dry tetrahydrofuran (THF) was added dropwise into a solution of 5-methyl-5-carboxyl-1,3-dioxan-2-one (MTC-OH) (2.75 g, 17.2 mmol, MW 160.1) in 50 mL of dry THF, followed by adding a catalytic amount (3 drops) of anhydrous dimethylformamide (DMF) over 30 min under nitrogen atmosphere. The reaction solution was stirred for 1 hour with $N_2$ bubbled through to remove volatiles. After the reaction, the solvent was evaporated under vacuum yielding MTC-Cl, which was not further purified.

Example 2

Preparation of MTC-C2 (MW 188.2)

I) bis-MPA (22.1 g, 0.165 mol, MW 134.1) was added to ethanol (150 mL) with Amberlyst-15 (6.8 g), and refluxed overnight. The resins were then filtered out and the filtrate was evaporated. Dichloromethane (200 mL) was added to the resulting viscous liquid to filter the unreacted reagent and byproduct. After the solution was dried over MgSO4 and evaporated, ethyl 2,2-bis(methylol)propionate (MW 162.2) was obtained as a clear and colorless liquid (24.3 g, 91%). $^1$H NMR (400 MHz, CDCl3, 22° C.): delta 4.09 (q, 2H, —OCH2CH3), 3.74 (d, 2H, —CH2OH), 3.57 (d, 2H, —CH2OH), 1.18 (t, 3H, —OCH2CH3), 0.98 (s, 3H, —CH3).

II) A solution of triphosgene (11.7 g, 0.039 mol) in dichloromethane (150 mL) was added dropwise to a dichloromethane solution (150 mL) of ethyl 2,2-bis(methylol)propionate (12.6 g, 0.078 mol, MW 162.2) and pyridine (39 mL, 0.47 mol) over 30 min at −75° C. with dry ice/acetone under nitrogen atmosphere. The reaction mixture was kept stirring for another 2 hours under chilled conditions and then allowed to warm up to room temperature. The reaction was quenched by addition of saturated aqueous $NH_4Cl$ (75 mL), after which the organic layer was washed with 1 M aqueous HCl (3×100 mL), saturated aqueous $NaHCO_3$ (1×100 mL), dried over MgSO4, filtered and evaporated. The residue was recrystalized from ethyl acetate to give MTC-C2 (MW 188) as white crystals (8.0 g, 55%). $^1$H NMR (400 MHz, $CDCl_3$, 22° C.): delta 4.67 (d, 2H, —CH2OCOO), 4.25 (q, 2H, —OCH2CH3), 4.19 (d, 2H, —CH2OCOO), 1.30 (s, 3H, —CH3), 1.27 (t, 3H, —OCH2CH3).

Example 3

Preparation of MTC-C8 (MW 272.3)

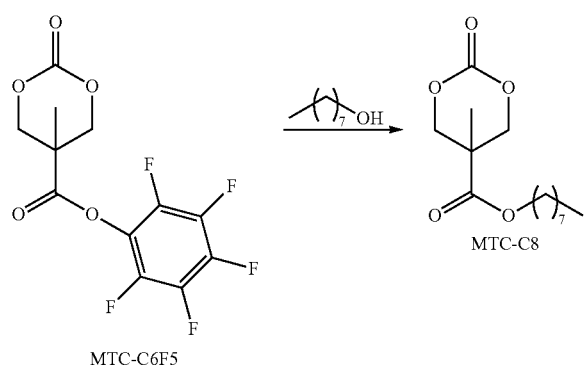

A flask was charged with MTC-C6F5 (5.5 g, 16.9 mmol, MW 326.2), octanol (2.0 g, 15.4 mmol), PROTON SPONGE (3.29 g, 15.4 mmol) and THF (8 mL). The reaction mixture was stirred for 12 hours and excess ammonium acetate was added. The reaction mixture was stirred for 3 additional hours and then added directly to a silica gel column. The product was isolated by column chromatography using hexane/ethyl acetate as the eluent to yield an oil. MTC-C$_8$. $^1$H NMR (400 MHz, CDCl3, 22° C.): delta 4.71 (d, 2H, —CH2OCOO), 4.23 (d, 2H, —CH2OCOO), 4.22 (t, 2H, —OCH2CH2), 1.68 (t, 2H, —OCH2CH2(CH2)5), 1.36 (s, 3H, —CH3), 1.31 (t, 10H, —CH2(CH2)5CH3), 0.90 (t, 3H, —(CH2)5CH3).

Example 4

MTC-C12 (MW 328.4) was Synthesized Using the General Procedure of Example 3, Replacing Ethanol with Dodecanol

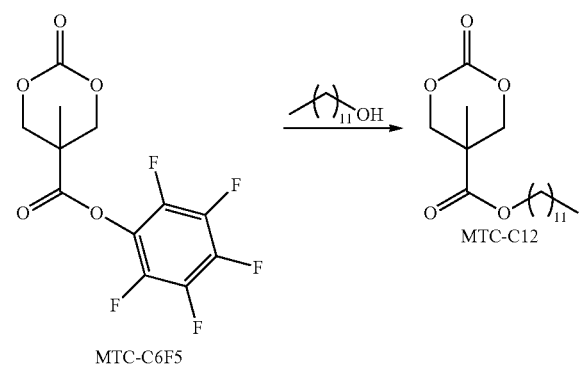

MTC-C12. $^1$H NMR (400 MHz, CDCl3, 22° C.): delta 4.69 (d, 2H, —CH2OCOO), 4.23 (d, 2H, —CH2OCOO), 4.21 (t, 2H, —OCH2CH2), 1.68 (t, 2H, —OCH2CH2(CH2)5), 1.35 (s, 3H, —CH3), 1.28 (t, 10H, —CH2(CH2)5CH3), 0.90 (t, 3H, —(CH2)5CH3).

Example 5

Synthesis MTC-Bn (MW 250.3)

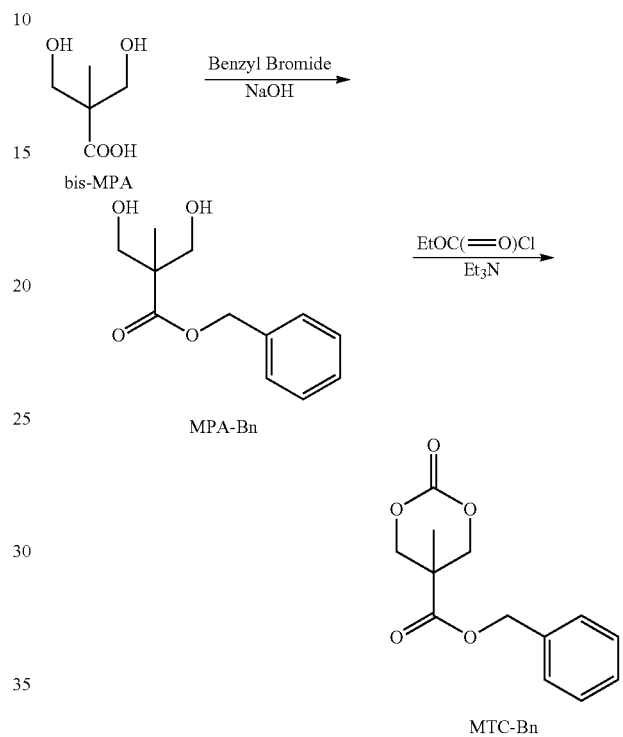

2,2-Bis(methylol)propanoic acid (bis-MPA) (20 g, 149.1 mmol, MW 134.1) and sodium hydroxide (5.96 g, 149.1 mmol) were combined in 100 mL DMSO and stirred overnight at 80° C. Benzyl Bromide (30.6 g, 178.9 mmol) was added dropwise. The solution cleared and the reaction was monitored by NMR. Once the reaction was complete, the solution was cooled to room temperature and water (500 mL) was added. The solution was extracted with diethyl ether several times and the diethyl ether solution was concentrated down to 250 mL. This solution was washed with water, sodium bicarbonate, and brine solutions, dried, and concentrated down to a solid. The solid was recrystallized from THF/hexanes to obtain white crystals of MPA-Bn (10.0 g, 30%). MPA-Bn (4.76 g, 21.2 mmol, MW 224.3) and triethylamine (5.4 g, 53.1) were then dissolved in dry THF (210 mL) and cooled to 0° C. Under nitrogen, ethyl chloroformate (5.1 g, 46.7 mmol) was added dropwise to the stirring solution. The solution was warmed to room temperature and reacted for 18 hours. The reaction solution was then concentrated down to a solid, and the solid was recrystallized twice out of diethyl ether to yield MTC-Bn as white crystals (3.86 g, 72.6%). $^1$H NMR (400 MHz, CDCl$_3$, 22° C.): delta 7.38 (m, 2H, C5H6), 5.24 (s, 2H, —OCH2C5H6) 4.72 (d, 2H, —CH2OCOO), 4.21 (d, 2H, —CH2OCOO), 4.21 (t, 2H, —OCH2C5H6), 1.36 (s, 3H, —CH3).

Cyclic carbonate monomers having protected sugar pendant groups include MTC-IPMAN, MTC-IPGAL and MTC-IPGLU.

Example 6

The Preparation of MTC-IPMAN (MW 402.2)

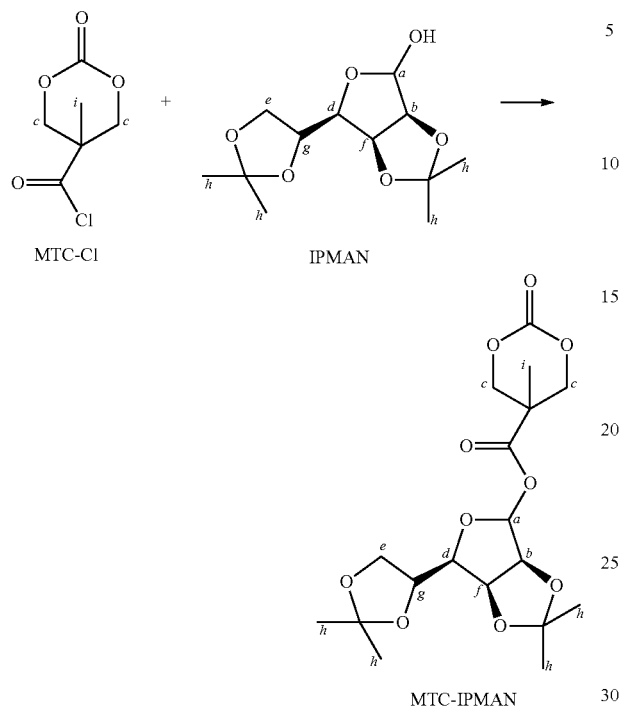

The preparation of MTC-IPMAN is representative. MTC-Cl was formed as described above and dissolved in 50 mL of dry dichloromethane (DCM). A mixture of 2,3;5,6-di-O-isopropylidene-D-mannofuranose (IPMAN) (4.13 g, 15.8 mmol, MW 260.3) and triethylamine (2.8 mL, 20.6 mmol) in 50 mL of dry dichloromethane (DCM) was added dropwise into the solution over 30 minutes at room temperature. Then, the reaction mixture was heated to 40° C. for 48 hours. After cooling the mixture to room temperature, the solution was concentrated and 100 mL THF was added to precipitate the triethylamine salt. After filtration of the salt and removal of the solvent, the resulting crude product was passed through a silica gel column by gradient eluting using ethyl acetate and hexane (20/80 to 50/50) to provide the product as sticky colorless oil that slowly solidified to a white solid (5.85 g, 85%). $^1$H-NMR (400 MHz, CDCl$_3$, 22° C.): delta 6.17 (s, 1H, H-a), 5.79 (dd, 1H, H-b), 4.83 (m, 1H, H-d), 4.66 (d, 2H, H-c), 4.41 (m, 1H, H-g), 4.22 (m, 2H, H-c), 4.03 (m, 2H, H-e+H-f), 3.73 (m, 1H, H-e), 1.33-1.50 (m, 15H, H-h+H-i).

Example 7

Preparation of MTC-IPGAL (MW 402.2)

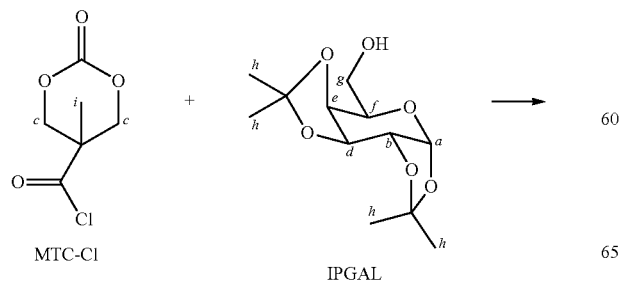

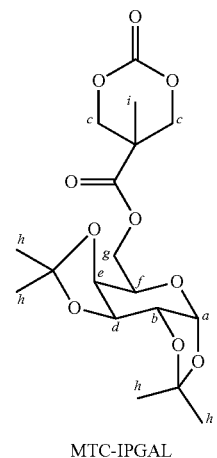

MTC-IPGAL was prepared using the procedure of Example 6 and 1,2;3,4-Di-O-isopropylidene-D-galactopyranose (IPGAL, MW 260.3). Yield 81%. $^1$H-NMR (400 MHz, CDCl$_3$, 22° C.): delta 5.54 (d, 1H, H-a), 4.70 (m, 2H, H-c), 4.62 (m, 1H, H-b), 4.41 (m, 1H, H-f), 4.33 (m, 2H, H-d and H-e), 4.26 (m, 3H, H-c and H-g), 4.03 (m, 1H, H-g), 1.32-1.49 (5 s, 15H, H-h+H-i).

Example 8

Preparation of MTC-IPGLU (MW 402.2)

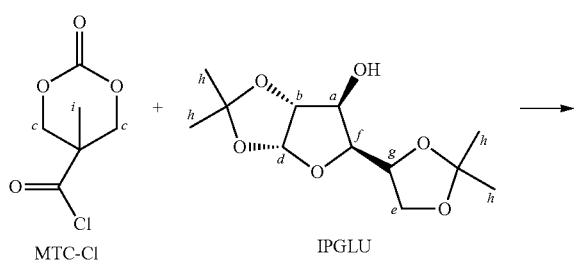

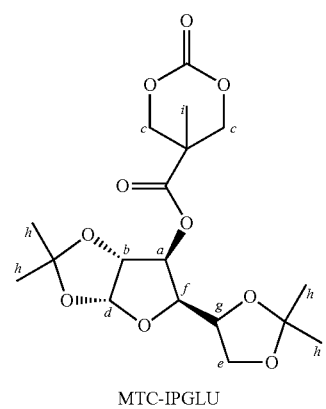

MTC-IPGLU was prepared using the procedure of Example 6 and 1,2;5,6-Di-O-isopropylidene-D-glucofuranose (IPGLU, MW 260.3). Yield 75%. $^1$H-NMR (400 MHz, CDCl$_3$, 22° C.): delta 5.90 (d, 1H, H-a), 5.39 (d, 1H, H-b), 4.69 (d, 2H, H-c), 4.46 (d, 1H, H-g), 4.18 (m, 2H, H-c), 4.06 (m, 2H, H-e and H-f), 4.00 (m, 1H, H-e), 1.30-1.52 (5 s, 15H, H-h+H-i).

Cyclic carbonates having a pendant phenylurea group were prepared according to Scheme 1.

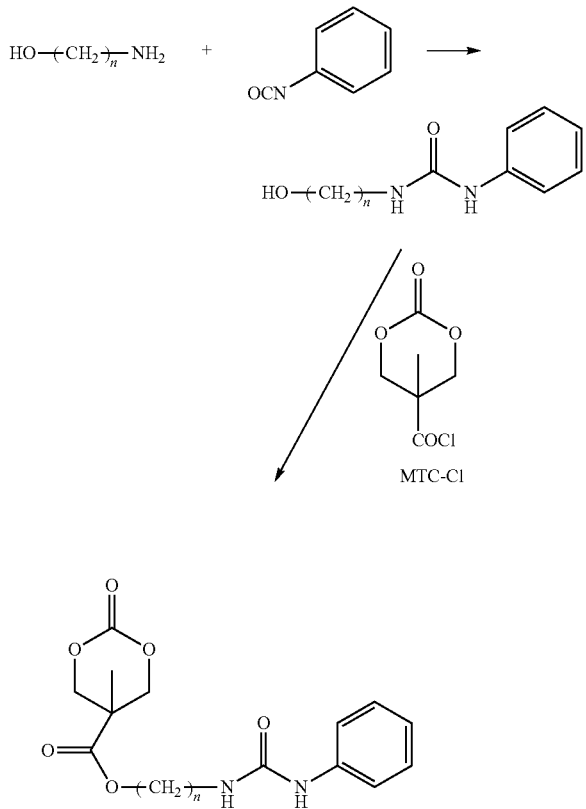

Scheme 1.

n = 2 MTC-PUC2
n = 8 MTC-PUC8
n = 12 MTC-PUC12

Example 9

Synthesis of MTC-PUC2 (MW 322.3)

1) Ethanolamine (5.0 g, 48.5 mmol, 1 eq) was placed in a dry 100 mL round bottom flask equipped with a stir bar, and dry THF (30 mL) was added. The resulting solution was chilled to 0° C. via an ice bath. Phenylisocyanate (5.19 g, 4.74 mL, 43.6 mmol, 0.9 equivalents) and 30 mL of dry THF was added dropwise to the ethanolamine/THF mixture through a dropping funnel over 30 min. The resulting mixture was left to warm to ambient temperature and allowed to stand under stirring for an additional 16 hours. Rotational evaporation was used to remove THF. The resulting crude product was recrystallized from ethyl acetate before being stirred vigorously for an additional 4 hours. The recrystallized solids were isolated by filtration and further washed with ethyl acetate and dried until a constant weight was reached, giving a yield of 7.0 g (~80%) intermediate phenylureaethanol (n=2 in Scheme 1). $^1$H-NMR (400 MHz, DMSO-d$_6$, 22° C.): delta 8.55 (s, 1H, —NHPh), 7.36 (d, 2H, PhH), 7.20 (t, 2H, PhH), 6.88 (t, 1H, PhH), 6.18 (t, 1H, —CH$_2$NHCO—), 4.76 (t, 1H, —OH), 3.43 (q, 2H, —CH$_2$OH), 3.15 (q, 2H, —CH$_2$NHCO—).

2) MTC-OH (4.3 g, 26.8 mmol) was converted to MTC-Cl by using oxalyl chloride as described above. The MTC-Cl was dissolved in 50 mL of dry methylene chloride and charged in an additional funnel. In a dry 500 mL round bottom flask equipped with a stir bar was charged phenylureaethanol (5.55 g, 25 mmol), pyridine (1.97 g, 2.02 mL, 25 mmol) and dry methylene chloride (150 mL). The additional funnel was attached under nitrogen and the flask cooled to 0° C. using an ice bath. The MTC-Cl solution was added dropwise during a period of 30 minutes and the resulting solution was stirred an additional 30 minutes. The ice bath was removed and the solution was allowed to warm up to ambient temperature and left under stirring for an additional 16 hours. The crude product was purified by column chromatography using silica gel. Methylene chloride was initially used as eluent before gradually increasing the polarity finishing with a final concentration of 5 vol % methanol. The product fractions were collected and the solvent was removed through rotational evaporation. The isolated product was dried under vacuum until a constant weight was reached yielding 8.0 g (about 80%) of an off-white/yellowish oil which crystallized upon standing. $^1$H-NMR (400 MHz, DMSO-d$_6$, 22° C.): delta 8.59 (s, 1H, —NHPh), 7.38 (d, 2H, PhH), 7.21 (t, 2H, PhH), 6.89 (t, 1H, PhH), 6.26 (t, 1H, —CH$_2$NHCO—), 4.57 (d, 2H, —COOCH$_2$CH$_2$—), 4.35 (d, 2H, —CH$_2$OCOO—), 4.16, (t, 2H, —CH$_2$OCOO—), 3.35 (q, 2H, —CH$_2$NHCO—), 1.20 (s, 3H, —CH$_3$).

Example 10

MTC-PUC8 (MW 406.5) was prepared using the procedure of Example 9 and 8-amino-1-octanol. Yield, 86%, $^1$H-NMR (400 MHz, DMSO-d$_6$, 22° C.): delta 8.37 (s, 1H, —NHPh), 7.38 (d, 2H, PhH), 7.21 (t, 2H, PhH), 6.86 (t, 1H, PhH), 6.10 (t, 1H, —CH$_2$NHCO—), 4.57 (d, 2H, —COOCH$_2$CH$_2$—), 4.39 (d, 2H, —CH$_2$OCOO—), 4.17, (t, 2H, —CH$_2$OCOO—), 3.06 (q, 2H, —CH$_2$NHCO—), 1.26-1.40 (2 s, 15H, —(CH$_2$)$_6$— and —CH$_3$).

Example 11

MTC-PUC12 (MW 462.6) was prepared using the procedure of Example 9 and 12-amino-1-dodecanol. Yield, 65%, $^1$H-NMR (400 MHz, DMSO-d$_6$, 22° C.): delta 8.37 (s, 1H, —NHPh), 7.34 (d, 2H, PhH), 7.17 (t, 2H, PhH), 6.83 (t, 1H, PhH), 6.09 (t, 1H, —CH$_2$NHCO—), 4.51 (d, 2H, —COOCH$_2$CH$_2$—), 4.33 (d, 2H, —CH$_2$OCOO—), 4.09, (t, 2H, —CH$_2$OCOO—), 3.02 (q, 2H, —CH$_2$NHCO—), 1.28-1.56 (m, 23H, —(CH$_2$)$_{10}$— and —CH$_3$).

II. bPEI-25 Modifications
MTC-IPGAL Modified bPEI-25
Mannose-modified bPEI-25 was formed according to Scheme 2.
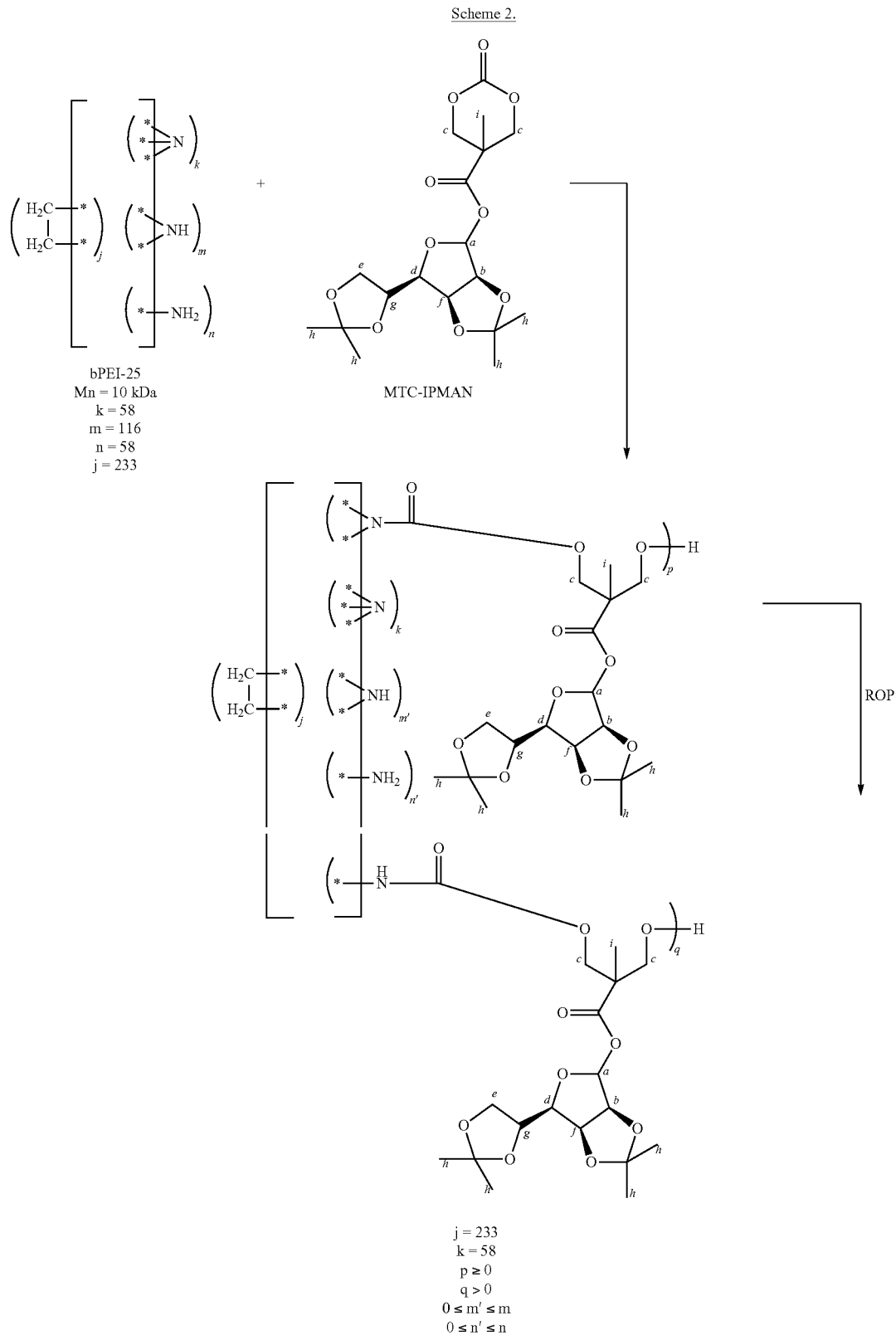

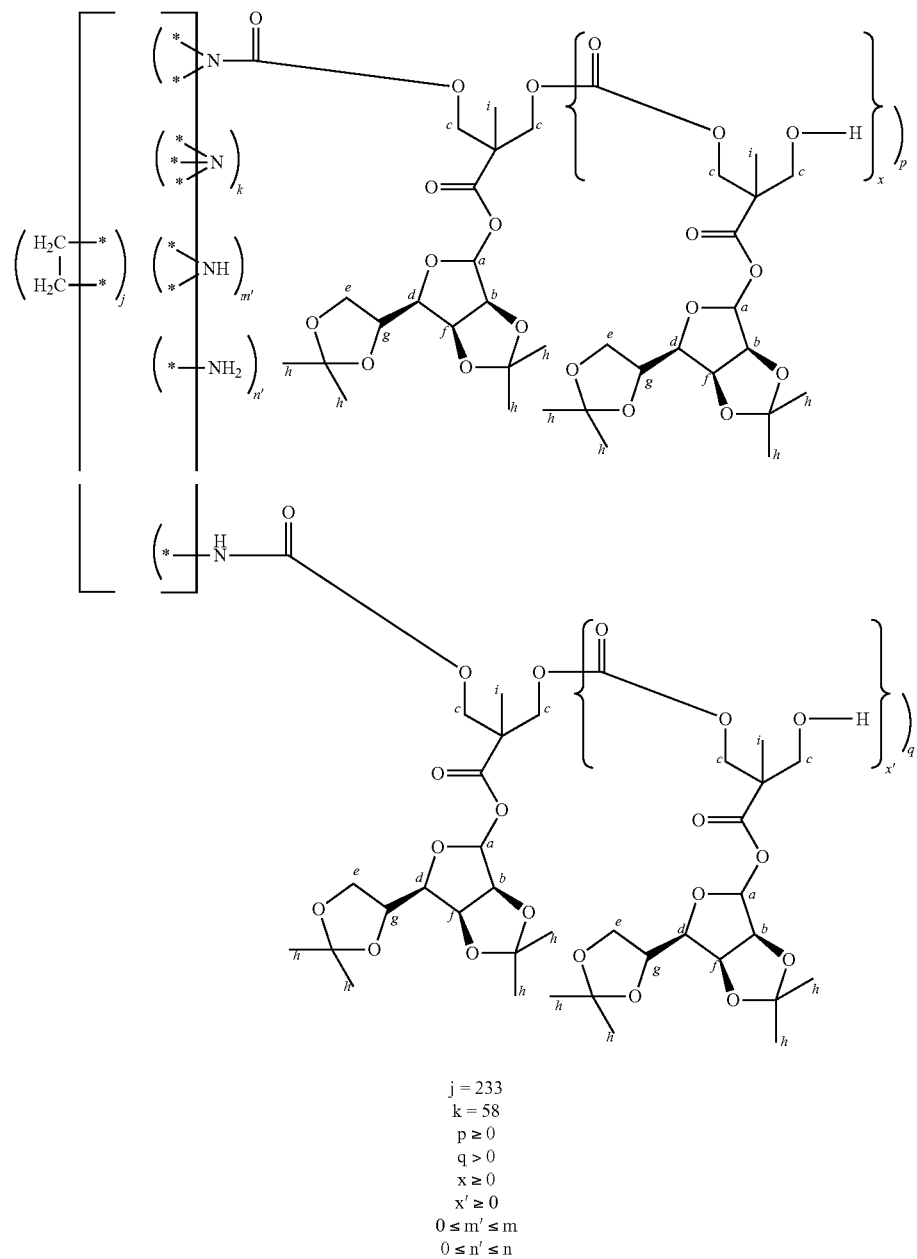

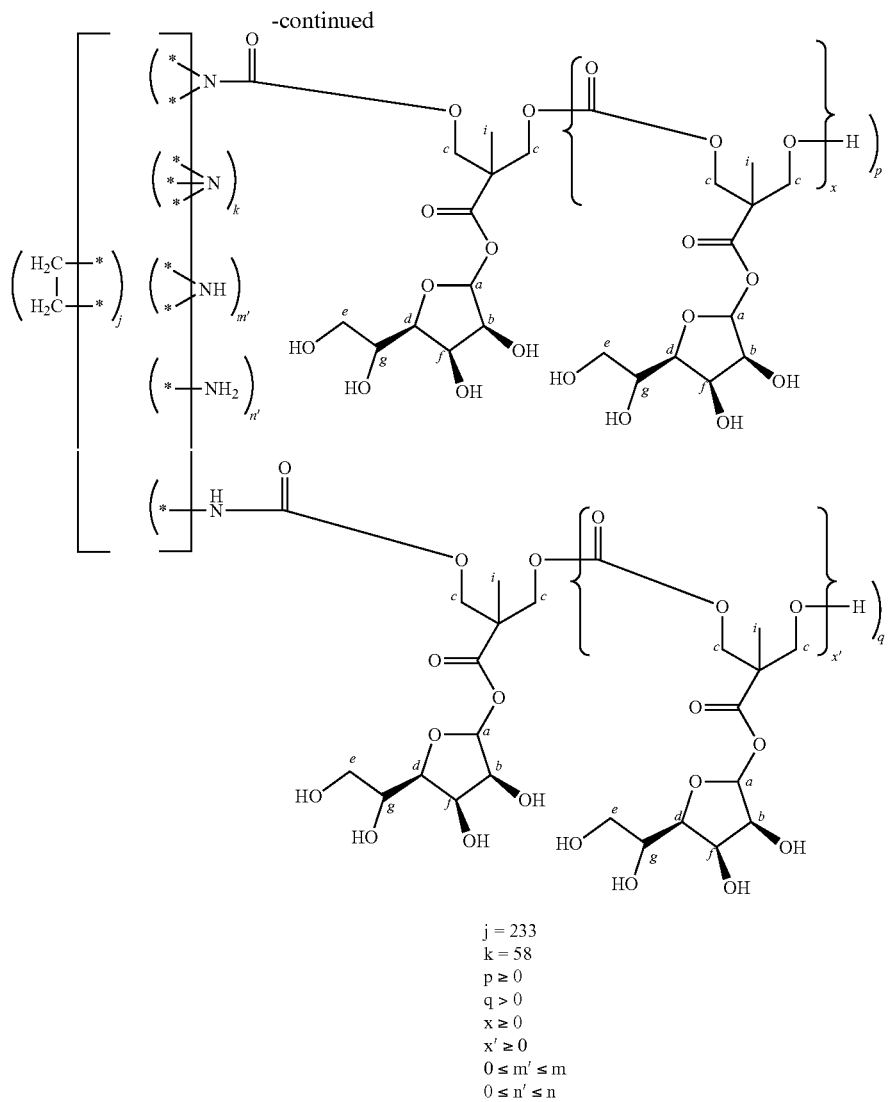

j = 233
k = 58
p ≥ 0
q > 0
x ≥ 0
x' ≥ 0
0 ≤ m' ≤ m
0 ≤ n' ≤ n

In the above structures, a set of curly braces encloses a polymer chain, and the subscript (e.g. x, x') represents the number of repeat units in the chain. The quantity n'+q equals the average total molar quantity of primary amine groups per macromolecule of the non-modified bPEI-25. The quantity m'+p equals the average total molar quantity of secondary amine groups per macromolecule of the non-modified bPEI-25.

Example 12

Synthesis of polymer A, mannose-modified bPEI-25. The procedure for ring-opening of MTC-IPMAN with bPEI-25 to form polymer A is given as a representative example. In a glove box, MTC-IPMAN (0.25 g, 0.625 mmol, MW=402.15 g) was added to the solution of bPEI-25 (0.25 g, 0.025 mmol based on 1 mole=10,000 g=Mn) in 2 mL of DCM, followed by adding 1,8-diazabicyclo[5,4,0]undec-7-ene (DBU, 4.7 microliters, 0.031 mmol). The bPEI-25:MTC-IPMAN feed mass ratio was 1:1, the molar ratio was 1:25. The reaction solution was stirred for 1 hour. 10 mL of methanol and 10 mL of 1 M HCl (aq.) were added. The resulting reaction mixture was heated at reflux for 2 hours before cooling to room temperature. Finally, the above mixture was purified by ultrafiltration in a Vivaspin 20 concentrator (molecular weight cutoff (MWCO)=5 k, Sartorius AG, Goettingen, Germany), washed 3 times with de-ionized (DI) water, and freeze-dried (0.36 g, 80%). $^1$H-NMR (400 MHz, D$_2$O, 22° C.): delta 4.08 (s, 40H, H-d and H-e), 2.70-3.65 (br, m, 992H, H-e, H-f, H-g and H of branched polyethylenimine), 1.06 (s, 61H, H-i).

bPEI-25 has an average of 58 primary amine groups, 116 secondary amine groups, 58 tertiary amine groups, and 233 ethylene groups per mole based on 1 mole=10000 g, thus 0.025 mmol bPEI-25 contains 1.45 mmol primary amine and 1.45 mmol secondary amine potentially capable of reacting with the cyclic carbonate monomer. However, the primary amine sites of bPEI-25 are more reactive and are present in excess relative to MTC-IPMAN. Under the above reaction conditions, only the primary amine groups of bPE-25 react with MTC-IPMAN, and no ring opening polymerization of MTC-IPMAN is observed (x=0 and x'=0 in the above structure of Scheme 2 for polymer A). The reaction results in modification of about 43% of the bPEI-25 primary amine groups, each with a single ring opened subunit of MTC-IPMAN. Theoretical values of the subscripts in the final structure of Scheme 2 for polymer A are x=0, x'=0, p=0, m'=116, q=25, n'=33, k=58, and j=233. Actual values found by NMR were x=0, x'=0, p=0, m'=116, q=20, n'=38, k=58, and j=233.

Examples 13 and 14

Using the procedure of Example 12, polymers B and C were synthesized using bPEI-25:MTC-IPMAN molar feed ratios of 1:8 and 1:75, respectively. The bPEI-25:mannose molar ratio found by NMR for Polymer B was 1:7. Thus, for polymer B, x=0, x'=0, p=0, m'=116, q=7, n'=51, k=58, and j=233 in the final structure of Scheme 2. In the case of polymer C, excess MTC-IPMAN was used relative to available primary amine sites. The excess MTC-IPMAN can react with the secondary amine sites or undergo ring opening polymerization initiated by the alcohol-containing first ring opened subunit of the modified primary amine sites. The bPEI-25:mannose molar ratio found by NMR for Polymer C was 1:67. Thus, for polymer C, x≥0, x≥0, p≥0, m'≤116, q=58, n'=0, k=58, and j=233 in the final structure of Scheme 2.

Examples 15 and 16

Synthesis of mannose-modified bPEI-25 in the absence of DBU. Using the procedure of Example 12, Polymers F and G were synthesized without DBU using a molar feed ratio bPEI-25:MTC-IPMAN of 1:25 for 18 hours and 1 hour, respectively, before acidification. In each case, available primary amine sites exceeded the available MTC-IPMAN. The bPEI-25:mannose molar ratio found by NMR for Polymer F was 1:23. For polymer F, x=0, x'=0, p=0, m'=116, q=23, n'=35, k=58, and j=233 in the final structure of Scheme 2. The bPEI-25:mannose molar ratio found by NMR for Polymer G was also 1:23. For polymer G, x=0, x'=0, p=0, m'=116, q=23, n'=35, k=58, and j=233 in the final structure of Scheme 2.

Examples 17, 18 and 19

Using the procedure of Example 12, Polymers L, M and N were prepared using a molar feed ratio bPEI-25:MTC-IPMAN of 1:58, 1:120, and 1:400, respectively, and a mass feed ratio of 1:2.3, 1:5, and 1:16, respectively, for 1 hour with DBU before acidification. The bPEI-25:mannose molar ratio found by NMR for Polymer L was 1:53. For polymer L, x=0, x'=0, p=0, m'=116, q=53, n'=5, k=58, and j=233 in the final structure of Scheme 2. In the case of polymer M the MTC-IPMAN was in excess of available primary amine sites. The excess MTC-IPMAN can react with the secondary amine sites or undergo ring opening polymerization initiated by the alcohol-containing first ring opened subunit of the modified primary amine sites. The bPEI-25:mannose molar ratio found by NMR for Polymer M was 1:120. For polymer M, x≥0, x'≥0, p≥0, m'≤116, q=58, n'=0, k=58, and j=233 in the final structure of Scheme 2. In the case of polymer N the MTC-IPMAN was present in excess of available primary amine sites and available secondary amine sites. The excess MTC-IPMAN can react with the secondary amine sites or undergo ring opening polymerization initiated by the alcohol-containing first ring opened subunit of the modified primary amine sites. The bPEI-25:mannose molar ratio of polymer N was not determined due to the propensity of the polymer to self-assemble in $D_2O$, Subscript values in the final structure of Scheme 2 for polymer N are estimated to be x≥0, x'≥0, p≥0, m'≤116, q=58, n'=0, k=58, and j>1.

Examples 20 and 21

Synthesis of mannose-modified bPEI-25 in the absence of DBU. Using the procedure of Example 12, polymers S and T were synthesized without DBU using a molar feed ratio bPEI-25:MTC-IPMAN of 1:12.5 and 1:6, respectively, and mass feed ratio of 2:1 and 4:1, respectively, for 1 hour before acidification. The BPEI-25:MTC-IPMAN molar ratio found by NMR for polymer S was 1:12.2. For polymer S, x=0, x'=0, p=0, m'=116, q=12.2, n'=45.8, k=58, and j=233 in the final structure of Scheme 2. The bPEI-25:mannose molar ratio found by NMR for Polymer T was 1:5.5. For polymer T, x=0, x'=0, p=0, m'=116, q=5.5, n'=52.5, k=58, and j=233 in the final structure of Scheme 2.

MTC-IPGAL Modified bPEI-25

Glucose-modified bPEI-25 was formed according to Scheme 3.

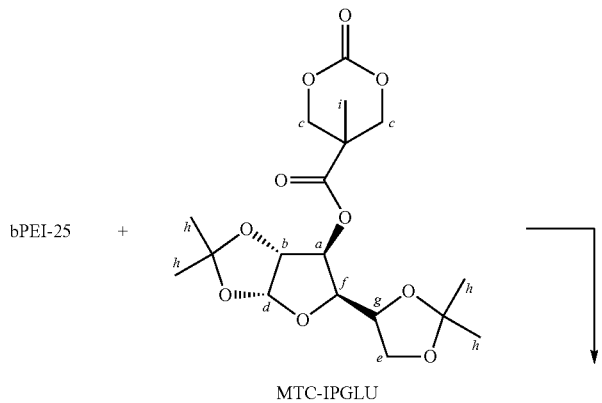

MTC-IPGLU

-continued j = 233
k = 58
p ≥ 0
q > 0
x ≥ 0
x' ≥ 0
0 ≤ m' ≤ m
0 ≤ n' ≤ n

↓ MeOH/HCl

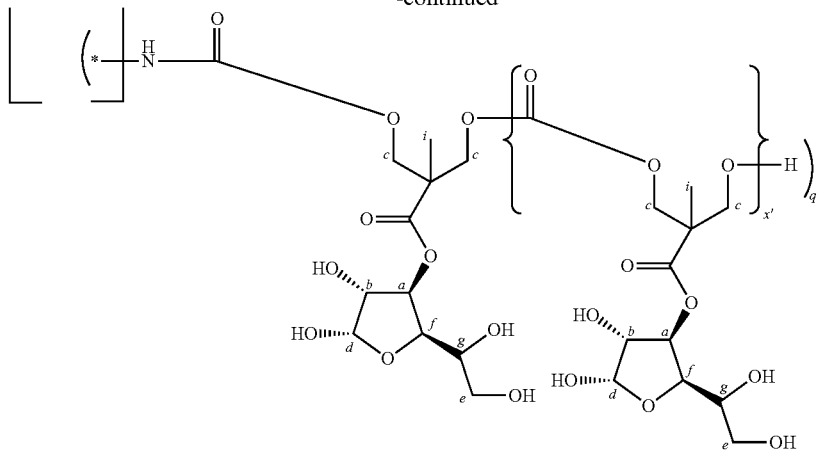

j = 233
k = 58
p ≥ 0
q > 0
x ≥ 0
x' ≥ 0
0 ≤ m' ≤ m
0 ≤ n' ≤ n

Example 22

The preparation of polymer H. The reaction of MTC-IP-GLU (MW 402.15) with bPEI-25 (1 mole=10000 g) followed the general procedure of Example 12 without DBU using a bPEI-25:MTC-IPGLU molar feed ratio of 1:25, and mass feed ratio of 1:1. The reaction time was 1 hour before acidification and purification by ultrafiltration to give polymer H. The bPEI-25:glucose molar ratio found by NMR for polymer H was 1:23. For polymer H, x=0, x'=0, p=0, m'=116, q=23, n'=35, k=58, and j=233 in the final structure of Scheme 3.

MTC-IPGAL Modified bPEI-25

Galactose-modified bPEI-25 was formed according to Scheme 4.

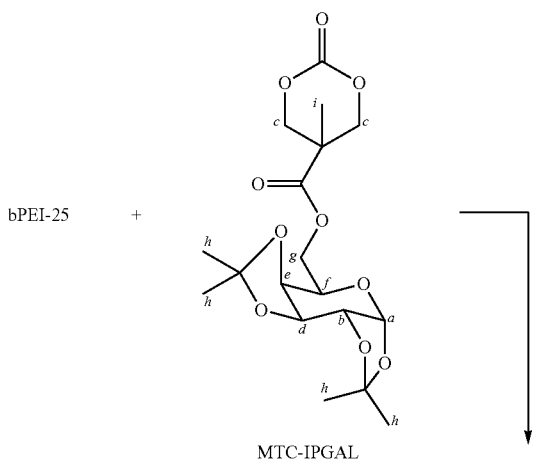

Scheme 4.

bPEI-25 +

MTC-IPGAL

-continued
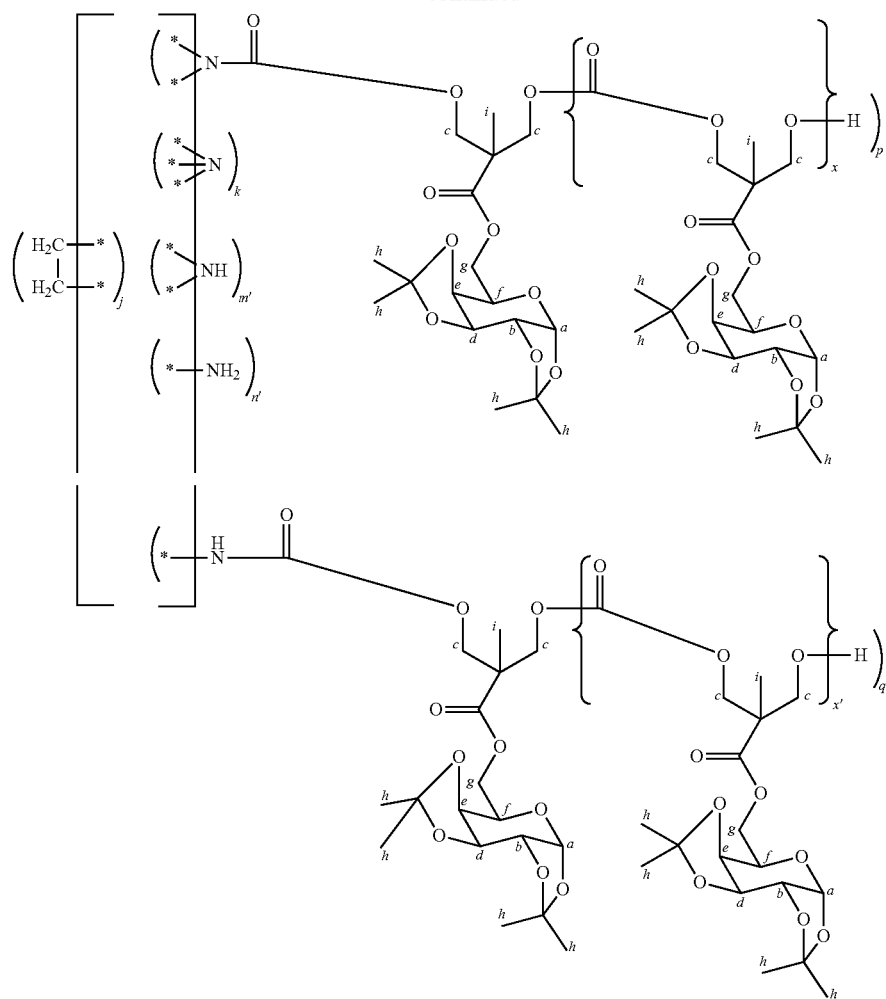
j = 233
k = 58
p ≥ 0
q > 0
x ≥ 0
x' ≥ 0
0 ≤ m' ≤ m
0 ≤ n' ≤ n
↓ MeOH/HCl
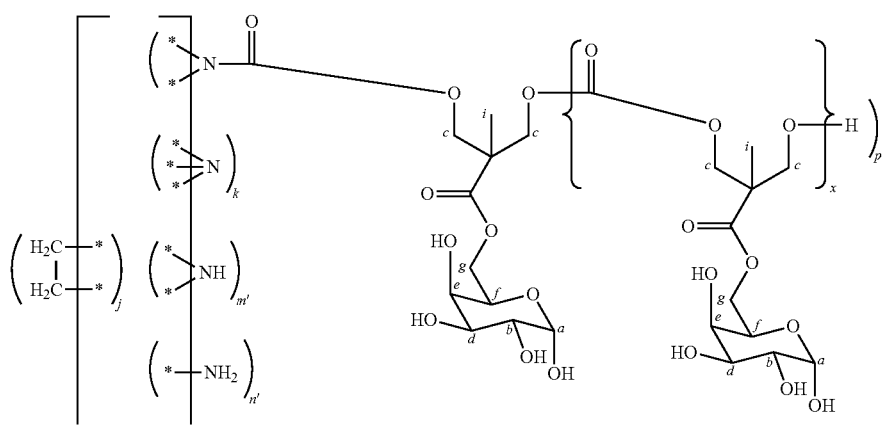

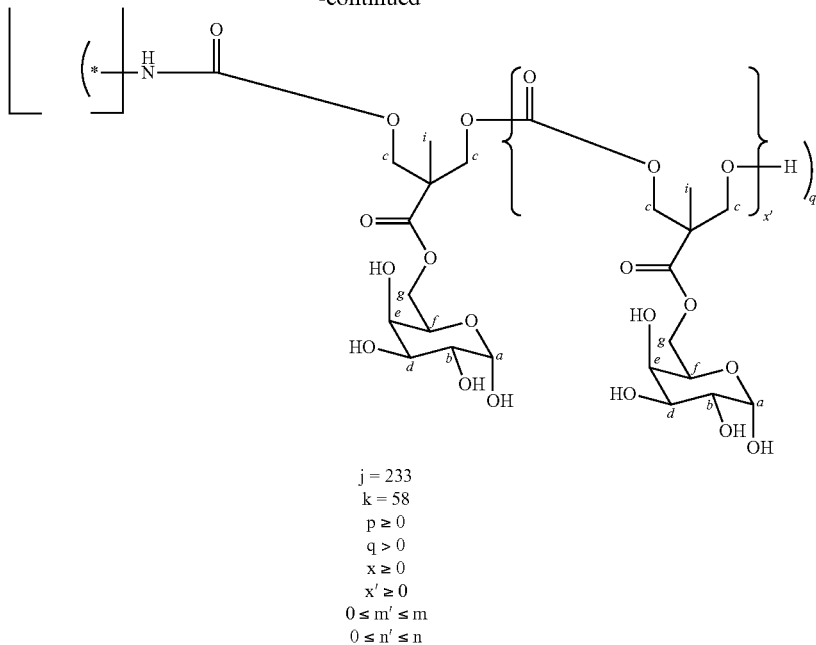

j = 233
k = 58
p ≥ 0
q > 0
x ≥ 0
x' ≥ 0
0 ≤ m' ≤ m
0 ≤ n' ≤ n

Examples 23

The preparation of polymer I. The reaction of MTC-IPGAL (MW 402.15) with bPEI-25 (1 mole=10000 g) followed the general procedure of Example 12 using a bPEI-25:MTC-IPGAL molar feed ratio of 1:25 and a mass feed ratio of 1:1 without DBU. The reaction time was 1 hour before acidification and purification by ultrafiltration to give polymer I. The bPEI-25:galactose molar ratio found by NMR for polymer I was 1:24. For polymer I, x=0, x'=0, p=0, m'=116, q=24, n'=34, k=58, and j=233 in the final structure of Scheme 4.

Example 24

Polymer R was synthesized according to Example 23 using a bPEI-25:MTC-IPGAL molar feed ratio of 1:12.5 and a mass feed ratio of 2:1. The bPEI-25:galactose molar ratio found by NMR for polymer R was 1:12. For polymer R, x=0, x'=0, p=0, m'=116, q=12, n'=46, k=58, and j=233 in the final structure of Scheme 4.

Example 25

Polymer U was synthesized according to Example 23 using a bPEI-25:MTC-IPGAL molar feed ratio of 1:6 and a mass feed ratio of 4:1. The BPEI-25:galactose molar ratio found by NMR for polymer U was 1:5.6. For polymer U, x=0, x'=0, p=0, m'=116, q=5.6, n'=52.4, k=58, and j=233 in the final structure of Scheme 4.

TMC Modified bPEI-25

TMC modified bPEI-25 polymers were prepared according to Scheme 5.

Scheme 5.

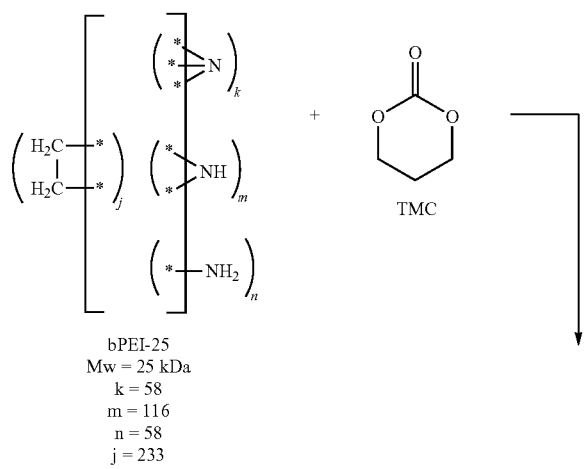

bPEI-25
Mw = 25 kDa
k = 58
m = 116
n = 58
j = 233

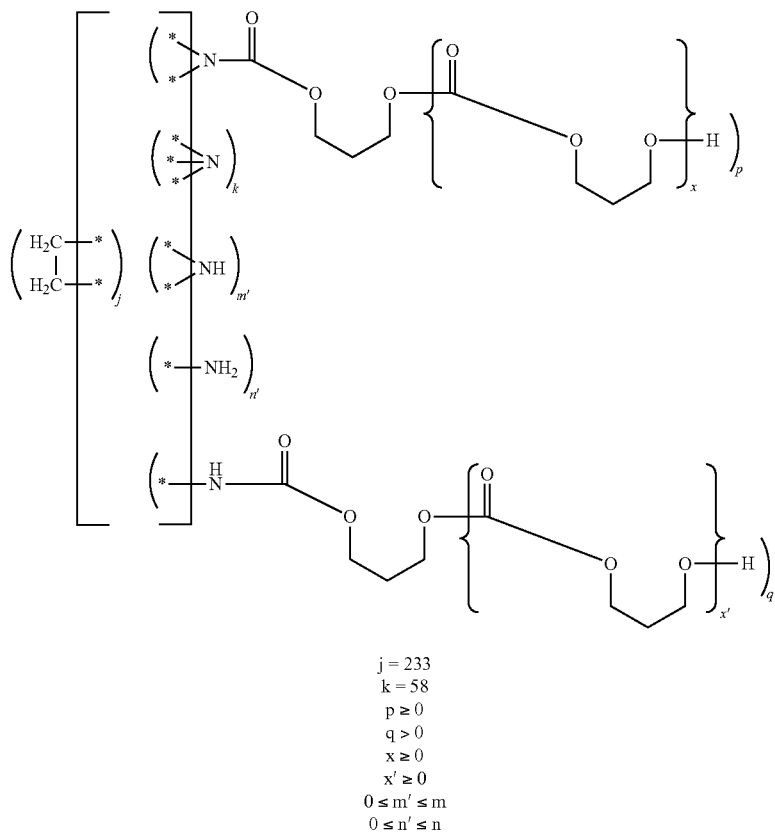

j = 233
k = 58
p ≥ 0
q > 0
x ≥ 0
x' ≥ 0
0 ≤ m' ≤ m
0 ≤ n' ≤ n

Example 26

Preparation of polymer J. The reaction of TMC (MW 102.1) with bPEI-25 (1 mole=10000 g=Mn) followed the general procedure of Example 12 using a bPEI-25:TMC molar feed ratio of 1:100 and a mass feed ratio of 1:1 without DBU. The reaction time was 1 hour. The bPEI-25: ring opened TMC molar ratio found by NMR for Polymer J was 1:109. For polymer J, x≥0, x'≥0, p≥0, m'≤116, q=58, n'=0, k=58, and j=233 in the final structure of Scheme 5.

Example 27

Polymer K was synthesized according to Example 26 using a bPEI-25:TMC molar feed ratio of 1:25 and a mass feed ratio of 4:1. The bPEI-25: ring opened TMC molar ratio found by NMR for Polymer K was 1:27. For polymer K, x=0, x'=0, p=0, m'=116, q=25, n'=33, k=58, and j=233 in the final structure of Scheme 5.

Example 28

Polymer P was synthesized according to Example 26 using a bPEI-25:TMC molar feed ratio of 1:8 and a mass feed ratio of 12:1. The bPEI-25: ring opened TMC molar ratio found by NMR for Polymer P was 1:7. For polymer P, x=0, x'=0, p=0, m'=116, q=8, n'=50, k=58, and j=233 in the final structure of Scheme 5.

Example 29

Polymer V was synthesized according to Example 26 using a bPEI-25:TMC molar feed ratio of 1:1 and a mass feed ratio of 100:1. The bPEI-25: ring opened TMC molar ratio found by NMR for Polymer V was 1:1. For polymer V, x=0, x'=0, p=0, m'=116, q=1, n'=57, k=58, and j=233 in the final structure of Scheme 5.

MTC-C2 Modified bPEI-25
Example 30
Polymer O, an MTC-C2 modified bPEI-25, was prepared according to Scheme 6.
Scheme 6.
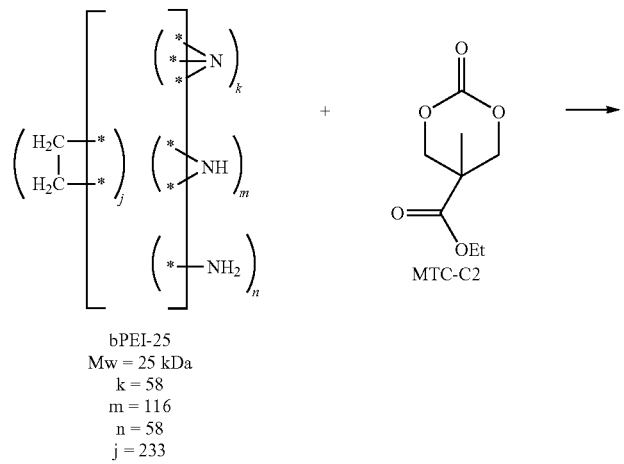
bPEI-25
Mw = 25 kDa
k = 58
m = 116
n = 58
j = 233
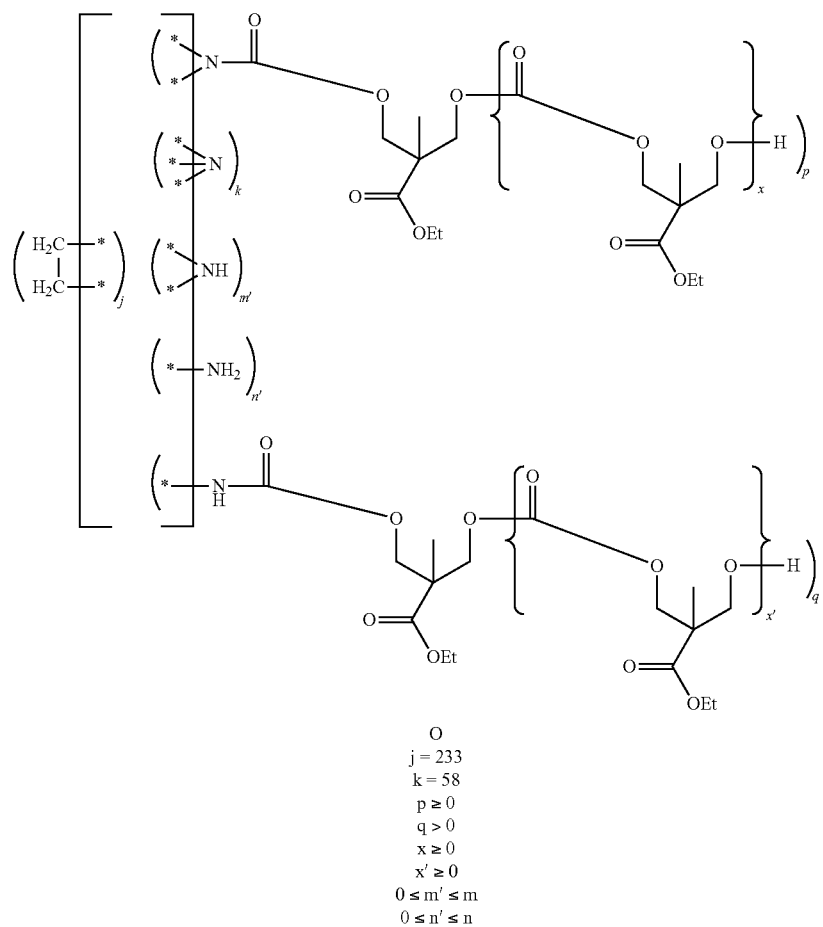
O
j = 233
k = 58
p ≥ 0
q > 0
x ≥ 0
x' ≥ 0
0 ≤ m' ≤ m
0 ≤ n' ≤ n Polymer O was synthesized according to Example 12 using hydrophobic monomer MTC-C2. The bPEI-25:MTC-C2 molar feed ratio was 1:25 and a mass feed ratio of 2:1. The BPEI-25: ring opened MTC-C2 molar ratio found by NMR in the product polymer O was 1:27. For polymer O, x=0, x'=0, p=0, m'=116, q=25, n'=33, k=58, and j=233 in Scheme 6.

MTC-Bn Modified bPEI-25

Example 31

Polymer P43, an MTC-Bn modified bPEI-25, was prepared according to Scheme 7 using the procedure of Example 12.

The bPEI-25:MTC-Bn molar feed ratio was 1:25 and the mass feed ratio was 1.6:1. The reaction time was 1 hour before purification by precipitation in ether. The BPEI-25:carbamate molar ratio found by NMR in the product polymer P43 was 1:29. For polymer P43, m=116, q=29, n'=29, k=58, and j=233 in Scheme 7.

Example 32 (Comparative)

Polymer P48 was prepared according to Example 31 using a bPEI-25:MTC-Bn molar feed ratio of 1:3 (based on 1 mole bPEI-25=10000 g, and MTC-Bn MW 250.3) and a mass feed ratio was 13.3:1. The reaction time was 1 hour before purification by precipitation in ether. The BPEI-25:carbamate molar ratio found by NMR in the product polymer P48 was 1:3. For polymer P48, m=116, q=3, n'=55, k=58, and j=233 in Scheme 7.

MTC-PUC2 Modified bPEI-25

Example 33

Polymer P44, an MTC-PUC2 modified bPEI-25, was prepared according to Scheme 8.

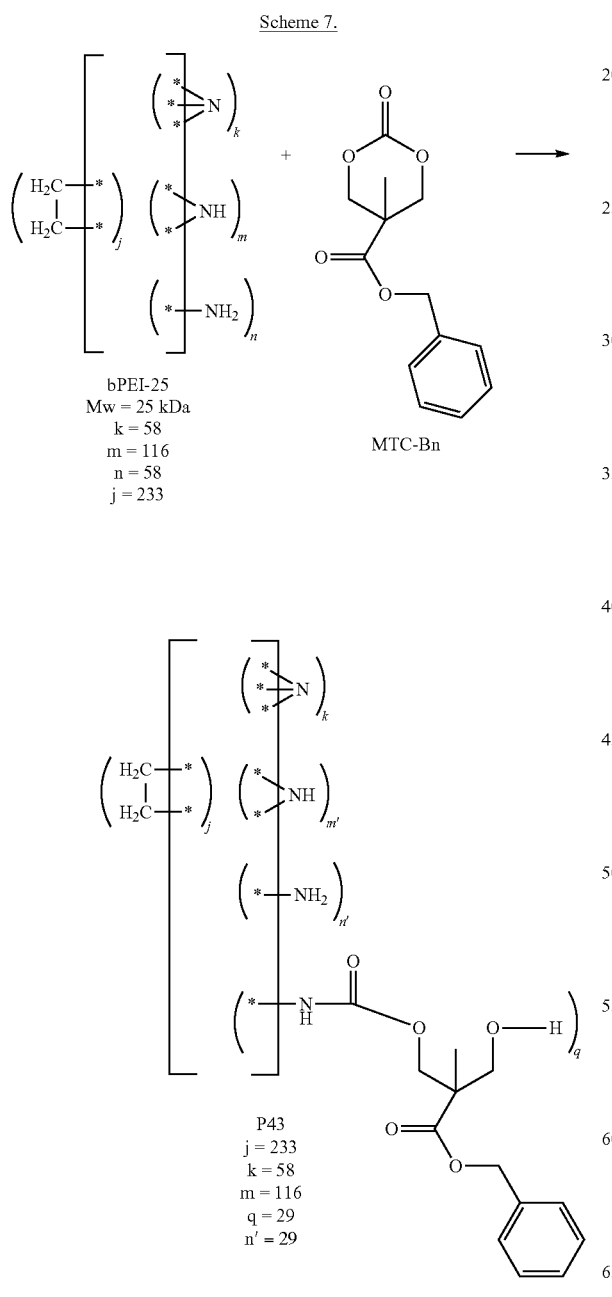

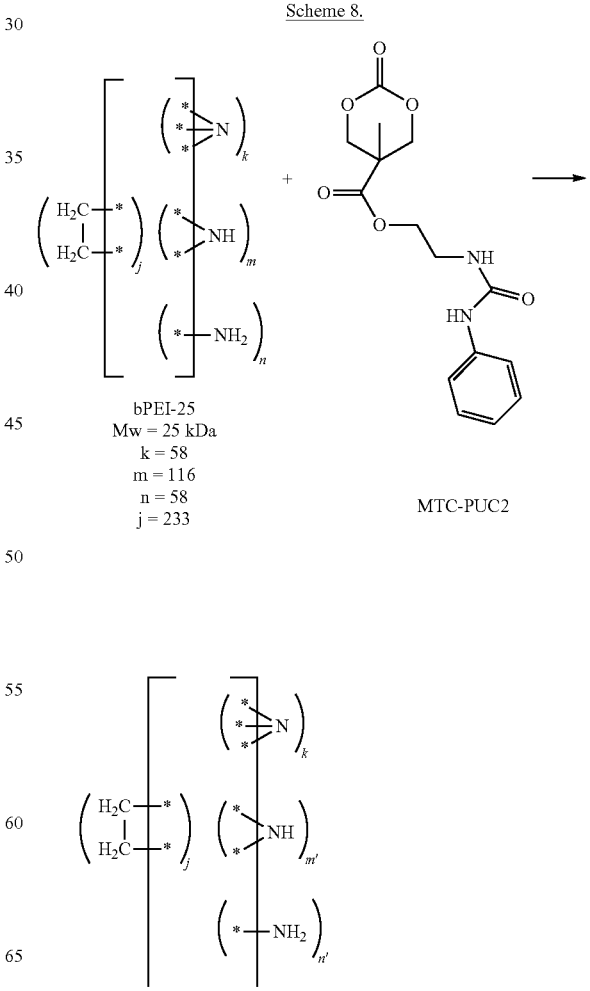

-continued

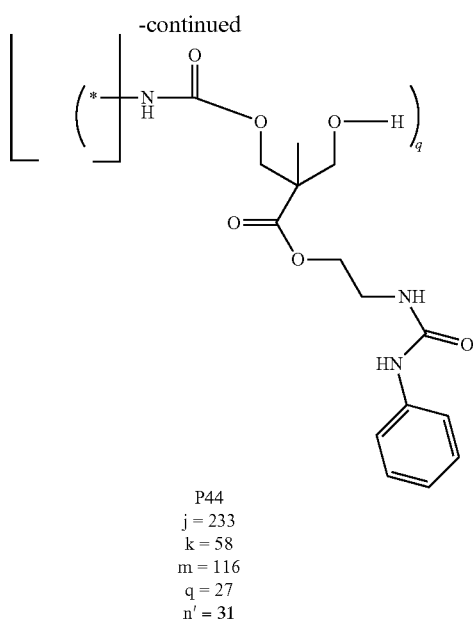

P44
j = 233
k = 58
m = 116
q = 27
n' = 31

Polymer P44 was synthesized according to Example 12 using hydrophobic monomer MTC-PUC2. The bPEI-25:MTC-PUC2 molar feed ratio was 1:25 and the mass feed ratio was 1.2:1. The reaction time was 1 hour before purification by precipitation in ether. The BPEI-25: carbamate molar ratio found by NMR in the product polymer P44 was 1:27. For polymer P44, m=116, q=27, n'=31, k=58, and j=233 in Scheme 8.

Example 34 (Comparative)

Polymer P49, an MTC-PUC2 modified bPEI-25, was prepared according to Example 33 using a bPEI-25:MTC-PUC2 molar feed ratio of 1:3 and a mass feed ratio was 10.4:1. The reaction time was 1 hour before purification by precipitation in ether. The BPEI-25: carbamate molar ratio found by NMR in the product polymer P49 was 1:3.4. For polymer P49, m=116, q=3.4, n'=54.6, k=58, and j=233 in Scheme 8.

Cholesteryl Modified bPEI-25

Cholesteryl bearing cyclic carbonate monomer Chol-MTC was synthesized from commercially available cholesteryl chloroformate (Chol-Cl) according to Scheme 9.

Scheme 9.

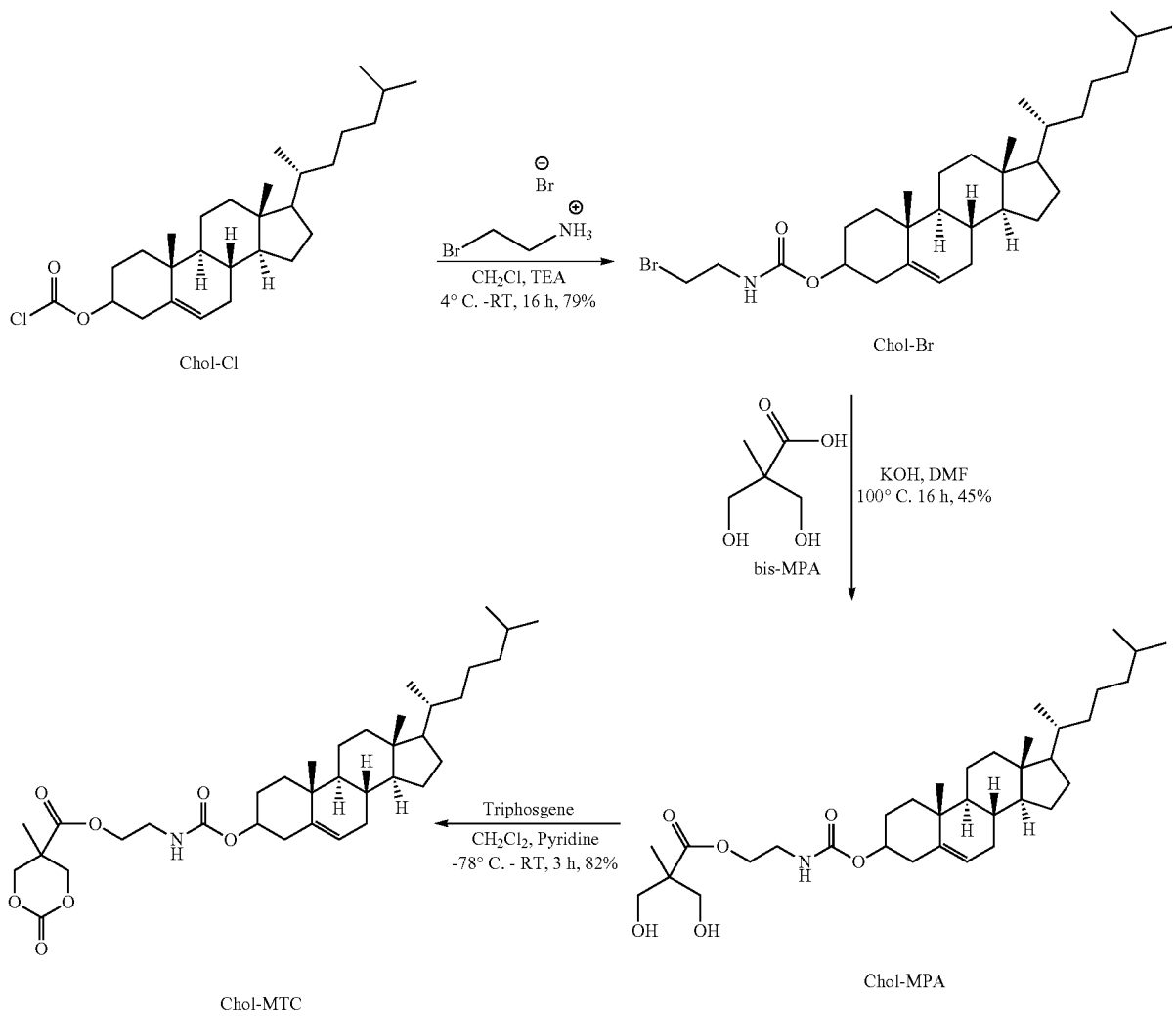

The preparation involves three steps: 1) reaction of the choloroformate Chol-Cl with 2-bromoethyl amine hydrobromide in dichloromethane with triethylamine (TEA) to form carbamate Chol-Br; 2) base-catalyzed reaction of Chol-Br with the acid diol bis-MPA in dimethylformamide (DMF)/ KOH to form the diol ester Chol-MPA, and 3) triphosgene-mediated cyclization of Chol-MPa to form the cyclic carbonate monomer Chol-MTC, with overall yield of about 26%. Detailed procedures of each of the three steps are provided below. $^1$H and $^{13}$C NMR were used to confirm the structures of the intermediates and the cyclic carbonate monomer.

Preparation of Chol-Br. In a 500 mL round bottom flask, equipped with a magnetic stir bar, cholesterol chloroformate (25.0 g, 55.7 mmol, 1.0 equiv.) and 2-bromoethylamine hydrobromide (12.9 g, 63.0 mmol, 1.1 equiv.) were suspended in dichloromethane (200 mL) and the suspension was chilled in an ice-bath. To this suspension, a solution of triethylamine (TEA) (18.0 mL, 13.06 g, 129.1 mmol, 2.3 equiv.) in dichloromethane (100 mL) was added dropwise over 1 hour. The reaction mixture was maintained in the bath for an additional hour and was allowed to warm to room temperature. The reaction was then allowed to proceed for another 14 h, after which dichloromethane was removed under vacuo and the resultant solids were suspended in a 1:1 mixture of ethyl acetate and hexanes (300 mL). The organic layer was washed 2 times with a mixture of saturated brine (100 mL) and de-ionized water (50 mL), and one time with saturated brine (100 mL). The organic layer was dried over sodium sulfate and the solvents were removed under vacuuo to yield a pale yellow solid (29.1 g, 97.4%). As the crude product was determined to have satisfactory purity by $^1$H NMR, no further purification was conducted. $^1$H NMR (400 MHz, CDCl3, delta, ppm): 5.38 (CH═C in cholesterol), 5.03 (NHCOO of side-chain), 4.50 (CH—OCONH of cholesterol), 3.58 (BrCH$_2$CH$_2$NH), 2.45-0.6 (rest of the protons from cholesterol).

Synthesis of Chol-MPA. In a 500 mL round bottom flask with magnetic stir bar, a mixture of KOH (85%, 2.0 g, 30.3 mmol, 1.1 equiv.), bis-MPA (4.20 g, 31.3 mmol, 1.1 equiv.) and dimethylformamide (DMF) (200 mL) were heated to 100° C. for 1.5 hours. A homogenous solution was formed, and Chol-Br (15.0 g, 28.0 mmol, 1.0 equiv.) was added to the hot solution. Stirring was continued with heating for 16 hours and most of the DMF was removed under reduced pressure, to result in an oily semisolid, which was then dissolved in 2:1 ethyl acetate:hexanes mixture (300 mL). The organic solution was washed with saturated brine (100 mL) and de-ionized water (100 mL) mixture. The resultant aqueous layer was extracted with ethyl acetate (3×100 mL) to recover Chol-MPA lost during the washing process. The combined organic layers were washed with saturated brine (80 mL) and de-ionized water (20 mL) mixture. The combined organic layer was dried with Na$_2$SO$_4$ and the solvent removed in vacuuo to result in crude product as a pale white waxy solid (16.5 g). The crude product was purified by flash column chromatography using silica as the packing material and a gradient of hexanes to ethyl acetate as the eluent to result in the final product Chol-MPA as a waxy white solid (10.7 g, 64.8%). $^1$H NMR (400 MHz, CDCl$_3$, delta, ppm): 5.35 (CH═C in cholesterol and NHCOO of side-chain), 4.47 (CH—OCONH of cholesterol), 4.26 (CH$_2$CH$_2$NHCOO), 3.88 and 3.72 (CH$_2$OH) 3.45 (CH$_2$CH$_2$NHCOO), 3.34 (OH), 2.50-0.60 (rest of the protons from cholesterol and CH$_3$ from bis-MPA).

Preparation of Chol-MTC. In a 500 mL round bottom flask with magnetic stir bar, Chol-MPA (10.1 g, 17.1 mmol, 1.0 equiv.) was dissolved in anhydrous dichloromethane (150 mL). Pyridine (8.2 mL, 8.0 g, 101.5 mmol, 5.9 equiv.) was added and the solution was cooled in a dry ice-acetone bath (−78° C.). To this cooled reaction mixture, triphosgene (2.69 g, 9.06 mmol, 1.9 equivalents based on functional equivalents of triphosgene) solution (dissolved in 50 mL dichloromethane) was added dropwise over 1 hour. After 1 hour, from −78° C., the reaction mixture was allowed to warm up to room temperature, and after 2 hours, the reaction was quenched by adding saturated aqueous ammonium chloride solution (50 mL). The organic layer was washed twice with a mixture of 1.0 N HCl (20 mL) and saturated brine (80 mL), followed by a mixture of saturated brine (50 mL) and saturated NaHCO$_3$ (50 mL), dried using Na$_2$SO$_4$. Removal of solvent in vacuo resulted in crude product as a slightly yellowish solid. The crude product was further purified by flash column chromatography using silica as the packing material and a gradient of chloroform to chloroform:ethyl acetate (4:1) mixtures as the eluent, to result in the final product Chol-MTC as a waxy white solid (6.8 g, 65%). $^1$H NMR (400 MHz, CDCl3, delta, ppm): 5.35 (CH═C in cholesterol), 4.95 (NH-COO), 4.86 and 4.27 (CH$_2$OCOOCH$_2$), 4.47 (CH—OCONH of cholesterol), 4.27 (CH$_2$CH$_2$NHCOO), 3.45 (CH$_2$CH$_2$NHCOO), 2.40-0.60 (rest of the protons from cholesterol and CH$_3$ in the cyclic carbonate monomer).

Example 35

The preparation of polymer P45. Chol-MTC modified bPEI-25 polymer, P45, was prepared according to Scheme 10.

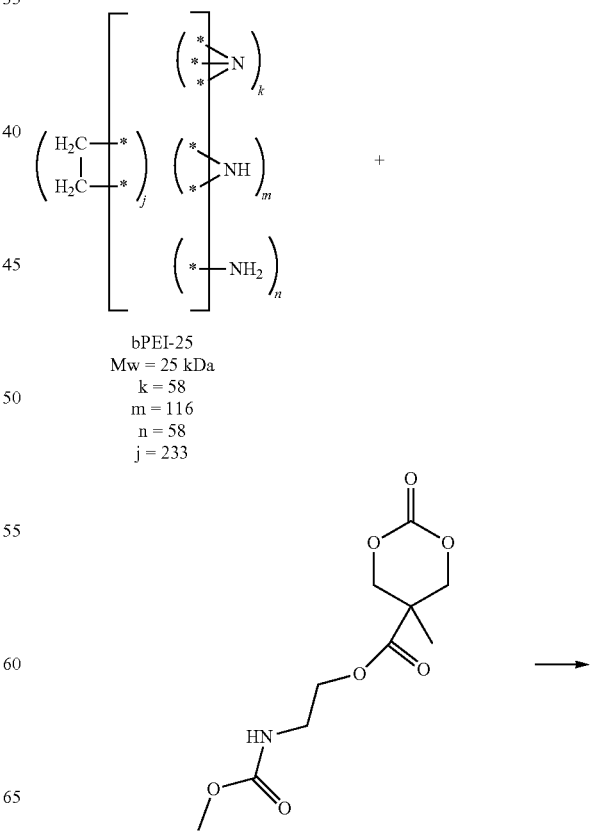

Scheme 10.

bPEI-25
Mw = 25 kDa
k = 58
m = 116
n = 58
j = 233

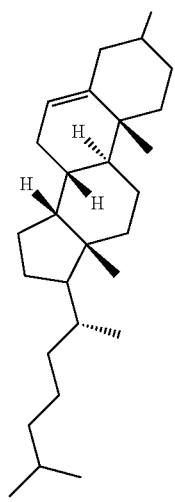

Chol-MTC

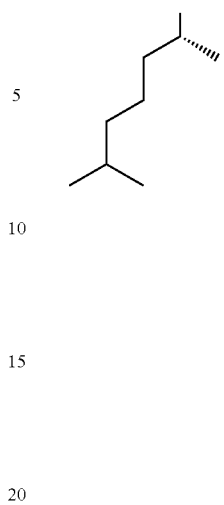

P45
j = 233
k = 58
m = 116
q = 2.9
n' = 55.1

In this example, the aim q value was 3, the aim n' value was 55 because more than three cholesteryl-containing side chain groups lead to insolubility of the final polymer. The bPEI-25: Chol-MTC molar feed ratio was 1:3 (based on 1 mole bPEI-25=10000 g, and Chol-MTC MW 615.9) and the mass feed ratio was 5.41:1. The reaction time was 1 hour before purification by precipitation in ether. The bPEI-25: carbamate molar ratio found by NMR for polymer P45 was 1:2.91. For polymer P45, m=116, q=2.9, n'=55.1, k=58, and j=233.

Example 36 (Comparative)

The preparation of polymer P46. Cholesteryl chloroformate modified bPEI-25 polymer, P46, was prepared according to Scheme 11.

Scheme 11.

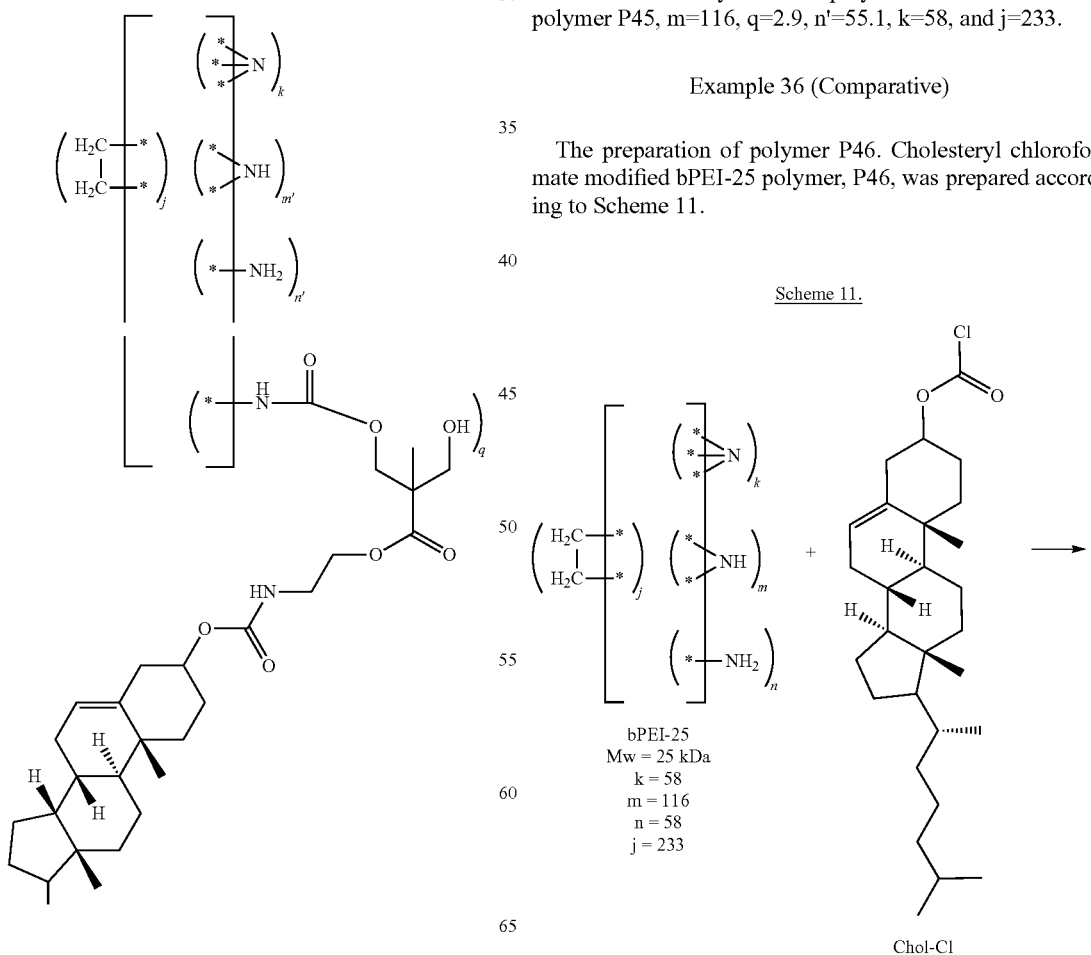

Scheme 12.

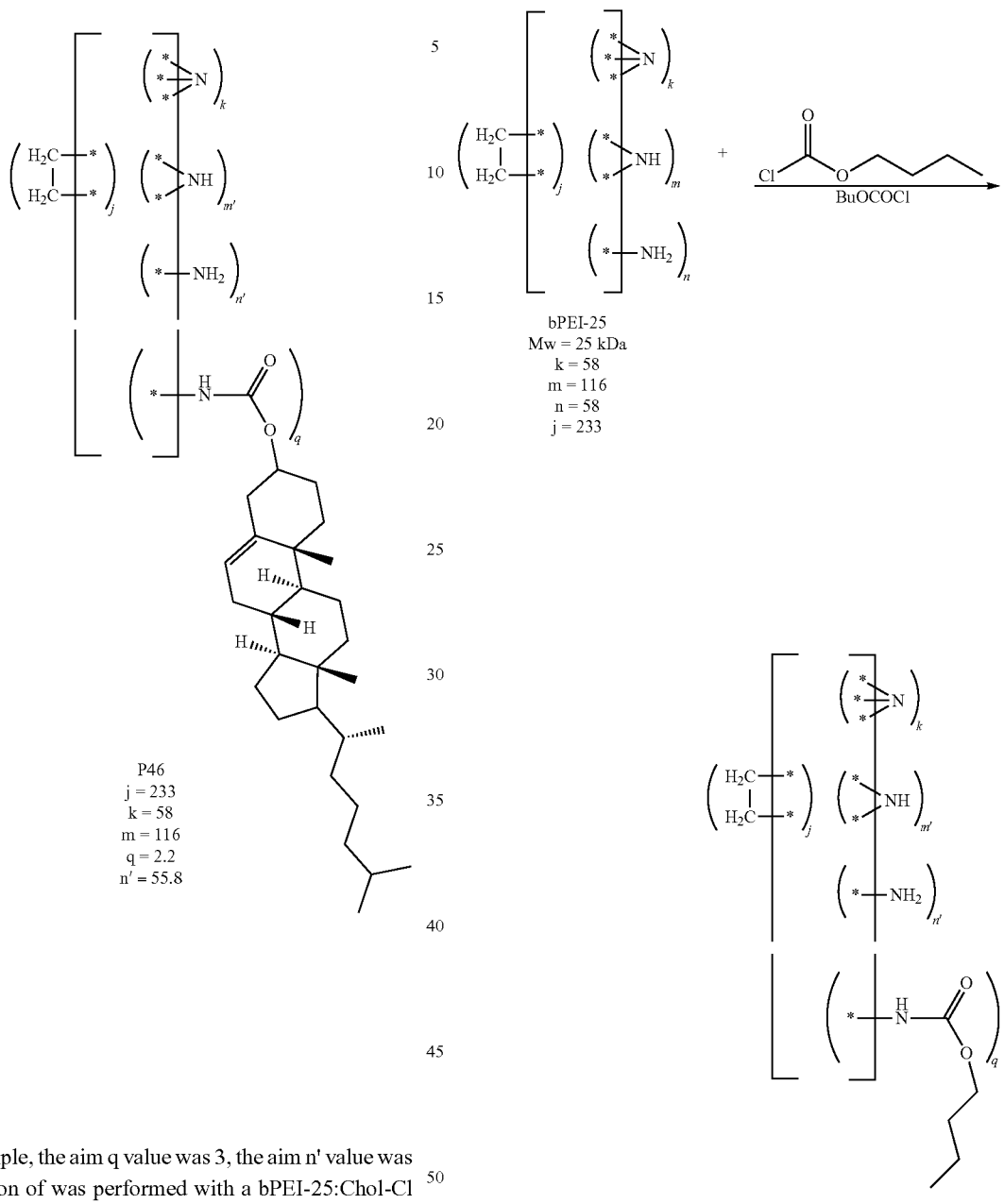

P46
j = 233
k = 58
m = 116
q = 2.2
n' = 55.8

In this example, the aim q value was 3, the aim n' value was 55. The reaction of was performed with a bPEI-25:Chol-Cl molar feed ratio was 1:3.2 (based on 1 mole bPEI-25=10000 g, and Chol-Cl MW 449.11), and the mass feed ratio was 7:1. The reaction time was 2 hours before purification by precipitation in ether. The bPEI-25: carbamate molar ratio found by NMR for polymer P46 was 1:2.2. For polymer P46 m=116, q=2.2, n'=55.8, k=58, and j=233.

Butyl Chloroformate Modified bPEI-25.

Example 37 (Comparative)

The preparation of polymer P47. Butyl chloroformate (BuOCOCl) modified bPEI-25 polymer, P47, was prepared according to Scheme 12.

In this example, the aim q value was 25, the aim n' value was 33. The bPEI-25:BuOCOCl molar feed ratio was 1:25.2 (based on 1 mole bPEI-25=10000 g, and BuOCOCl MW 136.57), and the mass feed ratio was 2.9:1. The reaction time was 2 hours before purification by precipitation in ether. The bPEI-25: carbamate molar ratio found by NMR for polymer P47 was 1:24.4. For polymer P47, m=116, q=24.4, n'=33.6, k=58, and j=233.

Table 4 summarizes the preparations of the polymers.

TABLE 4

| Ex. | Modified bPEI Name | Cyclic Monomer | Cyclic Monomer MW | Mass Feed Ratio (bPEI-2: Cyclic Monomer) | Molar Feed Ratio (bPEI: Cyclic Monomer) | Mol % Cyclic Monomer[a] | Used DBU? | Nitrogen Analysis (%) |
|---|---|---|---|---|---|---|---|---|
| 12 | A | MTC-IPMAN | 402.15 | 1:1 | 1:25 | 43.1 | Yes | 16.3 |
| 13 | B | MTC-IPMAN | 402.15 | 3:1 | 1:8 | 13.7 | Yes | 24.4 |
| 14 | C | MTC-IPMAN | 402.15 | 1:3 | 1:75 | 129.3 | Yes | 8.14 |
| 15 | F | MTC-IPMAN | 402.15 | 1:1 | 1:25 | 43.1 | No | 16.3 |
| 16 | G | MTC-IPMAN | 402.15 | 1:1 | 1:25 | 43.1 | No | 16.3 |
| 17 | L | MTC-IPMAN | 402.15 | 1:2.3 | 1:58 | 100.0 | Yes | 12.03 |
| 18 | M | MTC-IPMAN | 402.15 | 1:5 | 1:120 | 206.9 | Yes | 5.6 |
| 19 | N | MTC-IPMAN | 402.15 | 1:16 | 1:400 | 689.7 | Yes | 1.9 |
| 20 | S | MTC-IPMAN | 402.15 | 2:1 | 1:12.5 | 21.6 | No | 21.7 |
| 21 | T | MTC-IPMAN | 402.15 | 4:1 | 1:6 | 10.3 | No | 26.2 |
| 22 | H | MTC-IPGLU | 402.15 | 1:1 | 1:25 | 43.1 | No | 16.3 |
| 23 | I | MTC-IPGAL | 402.15 | 1:1 | 1:25 | 43.1 | No | 16.3 |
| 24 | R | MTC-IPGAL | 402.15 | 2:1 | 1:12.5 | 21.6 | No | 21.7 |
| 25 | U | MTC-IPGAL | 402.15 | 4:1 | 1:6 | 10.3 | No | 26.2 |
| 26 | J | TMC | 102.1 | 1:1 | 1:100 | 172.4 | No | 32.2 |
| 27 | K | TMC | 102.1 | 14:1 | 1:25 | 43.1 | No | 30.0 |
| 28 | P | TMC | 102.1 | 12:1 | 1:8 | 13.7 | No | 25.92 |
| 29 | V | TMC | 102.1 | 100:1 | 1:1 | 1.7 | No | 16.3 |
| 30 | O | MTC-C2 | 188 | 2:1 | 1:25 | 43.1 | No | 22.12 |
| 31 | P43 | MTC-Bn | 250.25 | 1.6:1 | 1:25 | 43.1 | No | 20.00 |
| 32 | P48 | MTC-Bn | 250.25 | 13.3:1 | 1:3 | 5.2 | No | 31.0 |
| 33 | P44 | MTC-PUC2 | 322 | 1.2:1 | 1:25 | 43.1 | No | 18.04 |
| 34 | P49 | MTC-PUC2 | 322 | 10.4:1 | 1:3 | 5.2 | No | 30.4 |
| 35 | P45 | Chol-MTC | 615.9 | 5.4:1 | 1:3 | 5.2 | No | 28.1 |
| 36 (comp) | P46 | Chol-Cl | 449.1 | 7:1 | 1:3.2 | 5.5 | No | 29.3 |
| 37 (comp) | P47 | BuOCOCl | 136.6 | 2.9:1 | 1:25.2 | 43.4 | No | 24.8 |

[a] moles cyclic monomer/moles primary amine groups ×100%.

Table 5 summarizes the NMR analysis of the modified bPEI-25 polymers.

TABLE 5

| Ex. | Modified bPEI Name | Cyclic Carbonate | Mole Ratio Found (NMR) bPEI: Carbamate Groups[a] | % of bPEI Primary Amine Groups Modified (NMR)[b] | # of bPEI Primary Amine Groups Modified Per Mole bPEI[a,c] |
|---|---|---|---|---|---|
| 12 | A | MTC-IPMAN | 1:20 | 34.5 | 20 |
| 13 | B | MTC-IPMAN | 1:7 | 12.1 | 7 |
| 14 | C | MTC-IPMAN | 1:67[a] | 115.5[b] | 67[c] |
| 15 | F | MTC-IPMAN | 1:23 | 39.7 | 23 |
| 16 | G | MTC-IPMAN | 1:23 | 39.7 | 23 |
| 17 | L | MTC-IPMAN | 1:53 | 91.4[b] | 53 |
| 18 | M | MTC-IPMAN | 1:120[a] | 206.9[b] | 120[c] |
| 19 | N | MTC-IPMAN | NA | NA | NA |
| 20 | S | MTC-IPMAN | 1:12.2 | 21.0 | 12.2 |
| 21 | T | MTC-IPMAN | 1:5.5 | 9.5 | 5.5 |
| 22 | H | MTC-IPGLU | 1:23 | 39.7 | 23 |
| 23 | I | MTC-IPGAL | 1:24 | 41.4 | 24 |
| 24 | R | MTC-IPGAL | 1:12 | 20.7 | 12 |
| 25 | U | MTC-IPGAL | 1:6 | 10.3 | 6 |
| 26 | J | TMC | 1:109[a] | 187.9[b] | 109[c] |
| 27 | K | TMC | 1:27 | 46.6 | 27 |
| 28 | P | TMC | 1:7 | 12.1 | 7 |
| 29 | V | TMC | 1:1 | 1.7 | 1 |
| 30 | O | MTC-C2 | 1:27 | 46.6 | 27 |
| 31 | P43 | MTC-Bn | 1:29 | 46.6 | 29 |
| 32 | P48 | MTC-Bn | 1:3.1 | 5.3 | 3.1 |
| 33 | P44 | MTC-PUC2 | 1:27 | 46.6 | 27 |
| 34 | P49 | MTC-PUC2 | 1:3.4 | 5.9 | 3.4 |
| 35 | P45 | Chol-MTC | 1:2.9 | 5 | 2.9 |
| 36 (comp) | P46 | Chol-Cl | 1:2.2 | 3.8 | 2.2 |
| 37 (comp) | P47 | BuOCOCl | 1:24.4 | 42.1 | 24.4 |

[a] based on 1 mole bPEI-25 = 10000 g, containing 58 primary amine groups per mole.
[b] A value greater than 100% indicates reaction at all active primary amine sites, and reaction of secondary amine groups and/or ring opening polymerization of the cyclic carbonate monomer.
[c] A number greater than 58 indicates reaction at all active primary amine sites, and reaction of secondary amine groups and/or ring opening polymerization of the cyclic carbonate monomer.

III. Complexes with Biologically Active Materials

Cell Cultures.

HepG2, HeLa and SK-OV-3 cells were cultured in Minimum Essential Medium Eagle (MEM, Invitrogen, Singapore, for HepG2) and RPMI 1640 medium (Invitrogen, Singapore, for HeLa and SK-OV-3). Both media were supplemented with 10% fetal bovine serum (FBS, Invitrogen, Singapore), streptomycin at 100 microgram/mL, penicillin at 100 U/mL, L-glutamine at 2 mM, and 1 mM sodium pyruvate (Sigma-Aldrich, Singapore). MEM was further supplemented with 1 mM non-essential amino acids (Sigma-Aldrich, Singapore). Cells were cultured at 37° C., under an atmosphere of 5% $CO_2$ and 95% humidified air. All cell lines were split using Trypsin/EDTA medium when 90% confluence was reached.

Formation of Polymer/siRNA and Polymer/DNA Complexes.

bPEI-25 and bPEI-2 were dissolved in DNase/RNase-free water and HPLC water respectively to make aqueous solutions of the polymer. To form the complexes, an equal volume solution of siRNA or DNA was dripped into the polymer solution to achieve the intended N/P ratios (molar ratio of nitrogen content in the polymer to the phosphorus content of the nucleic acids) under gentle vortexing for about 10 seconds. The mixture was equilibrated at room temperature for 30 minutes to allow for complete electrostatic interaction between the polymer and the siRNA or DNA molecules, before being used for subsequent studies.

Particle Size and Zeta Potential Analysis of Polymer/DNA and Polymer/siRNA Complexes.

The particle sizes and zeta potentials of the post-equilibrated polymer/DNA complexes were measured by dynamic light scattering (Brookhaven Instrument Corp., Holtsville, N.Y., U.S.A.) using a He—Ne laser beam at 658 nm, with a scattering angle of 90° and Zetasizer (Malvern Instrument Ltd., Worcestershire, UK) respectively. Particle size and zeta potential measurements were repeated for 3 runs per sample and reported as the mean±standard deviation of 3 readings.

Table 6 lists the hydrodynamic radius of some of the modified bPEI-25 polymers/GFP reporter gene complexes at two N/P ratios.

Figure 2:
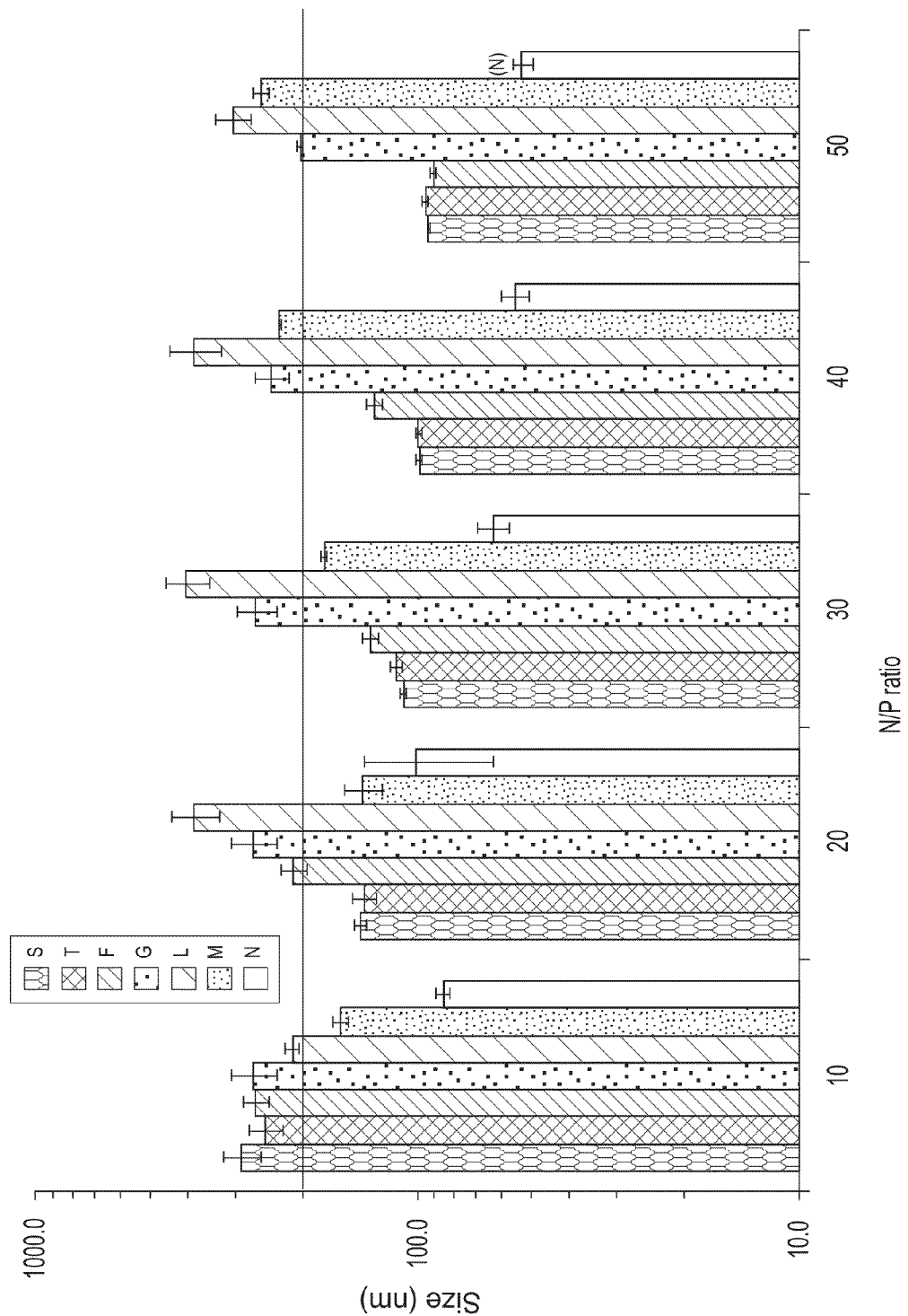
FIG. 2 is a bar graph showing particle sizes of luciferase reporter gene complexes of carbamate functionalized bPEI-25 polymers S, T, F, G, L, M, and N prepared at N/P 10 to 50.
Figure 3:
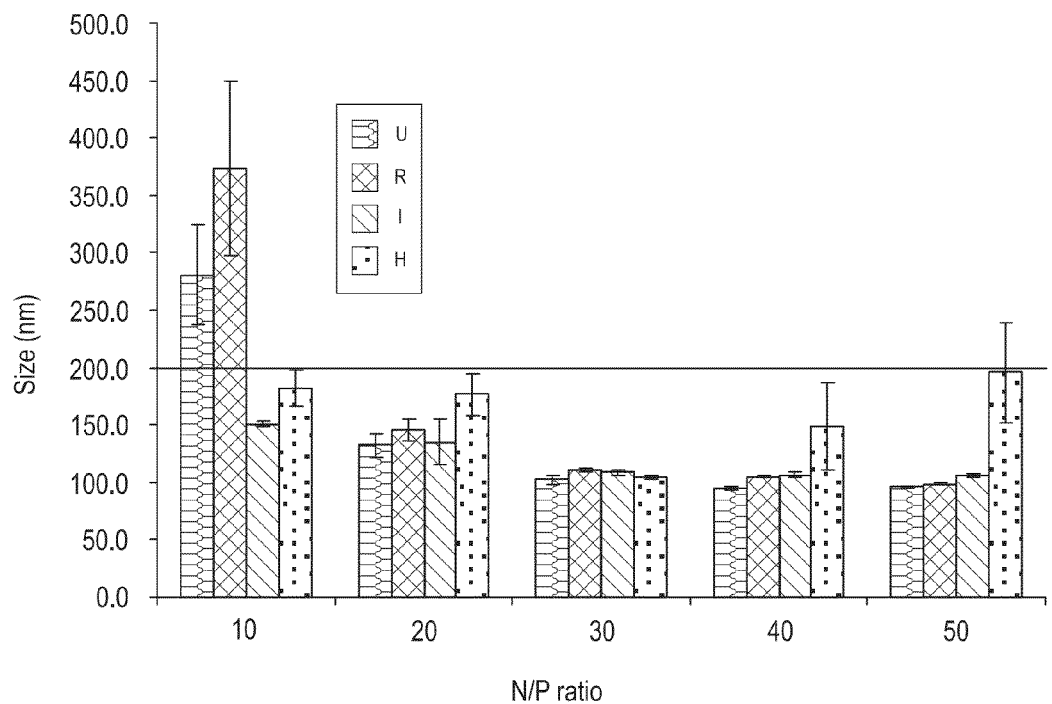
FIG. 3 is a bar graph showing particle sizes of luciferase reporter gene complexes of carbamate functionalized bPEI-25 polymers U, R, I, and H prepared at N/P 10 to 50.
Figure 4:
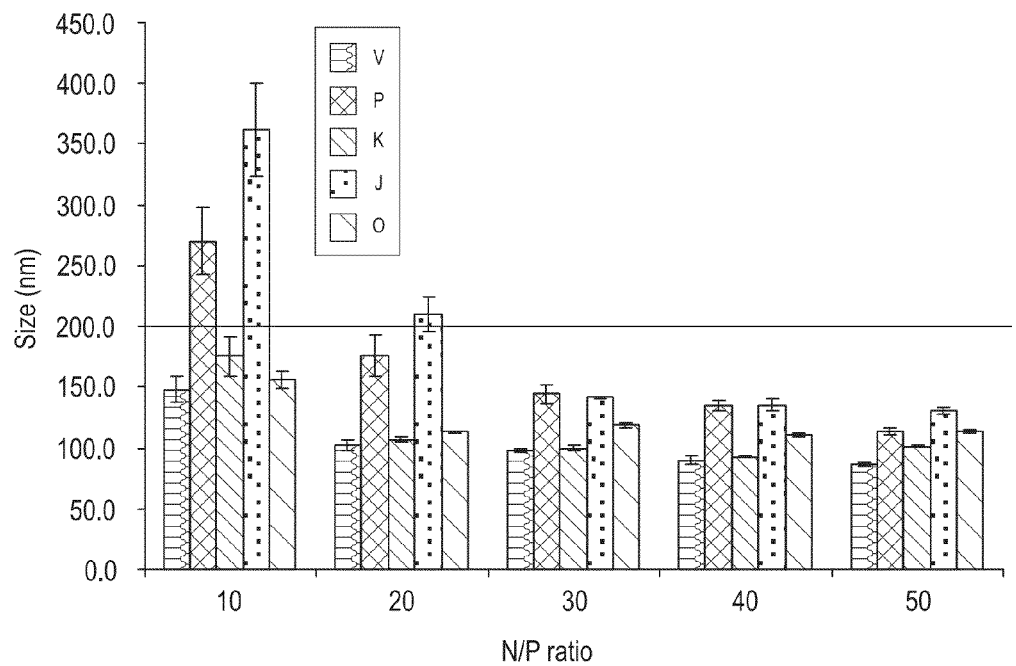
FIG. 4 is a bar graph showing particle sizes of luciferase reporter gene complexes of carbamate functionalized bPEI-25 polymers V, P, K, J and O prepared at N/P 10 to 50.

FIGS. 1 to 4, the size of the DNA complexes using GFP reporter gene (FIG. 1) and luciferase reporter gene (FIGS. 2 to 4) generally decreased with increasing N/P ratio, indicating that stronger electrostatic interaction between the polymer and DNA enabled the formation of more compact complexes between the cationic polymer and anionic DNA. This effect was more prominent in polymers A, B, F, U, R, P and J. GFP gene complexes of polymers A and B decreased from over 400 nm and 1000 nm at N/P 5, respectively, to 119 nm and 103 nm at N/P 30. Luciferase gene complexes of polymers F, U, R, P and J fell from over 250 nm, 280 nm, 370 nm, 270 nm and 260 nm at N/P 10, respectively, to 91 nm, 96 nm, 99 nm, 113 nm, and 131 nm at N/P 50, respectively. The particle size of polymer G/luciferase gene complex decreased from 269 nm at N/P 10 to 202 nm at N/P 50, within the desired nano-size range. For polymers S, T, U and V, which had the lowest percent of primary amine groups modified with cyclic carbonate monomer, more compact luciferase gene complexes were observed compared to other polymers in FIGS. 2 to 4. Polymer V produced the smallest luciferase gene complex (87 nm). Polymers C and L did not form a gene complex as effectively as other polymers, producing large particles even at high N/P ratios (FIG. 1 and FIG. 2). Narrow particle size distributions were obtained with gene complexes of A, B, S, T, F, G, L, U, R, I, H, V, P, J, K, and O, which had polydispersities of 0.178, 0.200, 0.168, 0.104, 0.129, 0.078, 0.150,

TABLE 6

| Ex. | Polymer Name | Cyclic Carbonate Monomer | % Primary Amine Groups Modified (NMR)[a] | DNA | Hydrodynamic Radius, $R_h$, of DNA complex (nm) | | | |
|---|---|---|---|---|---|---|---|---|
| | | | | | N/P 5 | N/P 10 | N/P 30 | N/P 50 |
| 12 | A | MTC-IPMAN | 34.5 | GFP | 415 | 226 | 119 | |
| 13 | B | MTC-IPMAN | 12.1 | GFP | 1392 | 185 | 103 | |
| 14 | C | MTC-IPMAN | 115.5[b] | GFP | 3044 | 678 | 500 | |
| 15 | F | MTC-IPMAN | 39.7 | Luciferase | | 183 | 113 | 99 |
| 16 | G | MTC-IPMAN | 39.7 | Luciferase | | 255 | 219 | 169 |
| 17 | L | MTC-IPMAN | 91.4[b] | Luciferase | | 212 | 402 | 304 |
| 18 | M | MTC-IPMAN | 206.9[b] | Luciferase | | 159 | 175 | 257 |
| 19 | N | MTC-IPMAN | NA | Luciferase | | 85 | 63 | 53 |
| 20 | S | MTC-IPMAN | 21.0 | Luciferase | | 288 | 109 | 93 |
| 21 | T | MTC-IPMAN | 9.5 | Luciferase | | 250 | 114 | 95 |
| 22 | H | MTC-IPGLU | 39.7 | Luciferase | | 182 | 105 | 196 |
| 23 | I | MTC-IPGAL | 41.4 | Luciferase | | 151 | 109 | 106 |
| 24 | R | MTC-IPGAL | 20.7 | Luciferase | | 373 | 111 | 99 |
| 25 | U | MTC-IPGAL | 10.3 | Luciferase | | 281 | 102 | 96 |
| 26 | J | TMC | 187.9[b] | Luciferase | | 362 | 142 | 131 |
| 27 | K | TMC | 46.6 | Luciferase | | 176 | 100 | 101 |
| 28 | P | TMC | 12.1 | Luciferase | | 270 | 144 | 113 |
| 29 | V | TMC | 1.7 | Luciferase | | 148 | 98 | 87 |
| 30 | O | MTC-C2 | 46.6 | Luciferase | | 156 | 119 | 114 |
| 31 | P43 | MTC-Bn | 46.6 | Luciferase | | 241 | 99 | 94 |
| 32 | P48 | MTC-Bn | 5.3 | Luciferase | | | | |
| 33 | P44 | MTC-PUC2 | 46.6 | Luciferase | | 287 | 101 | 98 |
| 34 | P49 | MTC-PUC2 | 5.9 | Luciferase | | | | |
| 35 | P45 | Chol-MTC | 5 | Luciferase | | | | |
| 36 (comp) | P46 | Chol-Cl | 3.8 | Luciferase | | 126.8 | 115.2 | 115 |
| 37 (comp) | P47 | BuOCOCl | 42.1 | Luciferase | | 112.4 | 99.9 | 101 |

[b]A percentage greater than 100 indicates reaction of all active primary amine sites, and reaction of secondary amine groups and/or ring opening polymerization of the cyclic carbonate monomer.

Polymeric nanoparticles, typically in the size range of 20 nm to 200 nm, are sufficiently large to avoid premature elimination via glomerular filtration in the kidneys, but are small enough to enter blood vessels and to capitalize on the enhanced permeation and retention (EPR) effect for passive accumulation in the target tumor tissues. As can be seen from 0.130, 0.120, 0.207, 0.209, 0.149, 0.075, 0.104, 0.097 and 0.123, respectively. Polydispersities of gene complexes of M and N were large, greater than 0.4 and 0.7, respectively. For comparison, a luciferase reporter gene complex of non-modified bPEI-25 at N/P 10 had a particle size of 84 nm (not shown).

Figure 5:
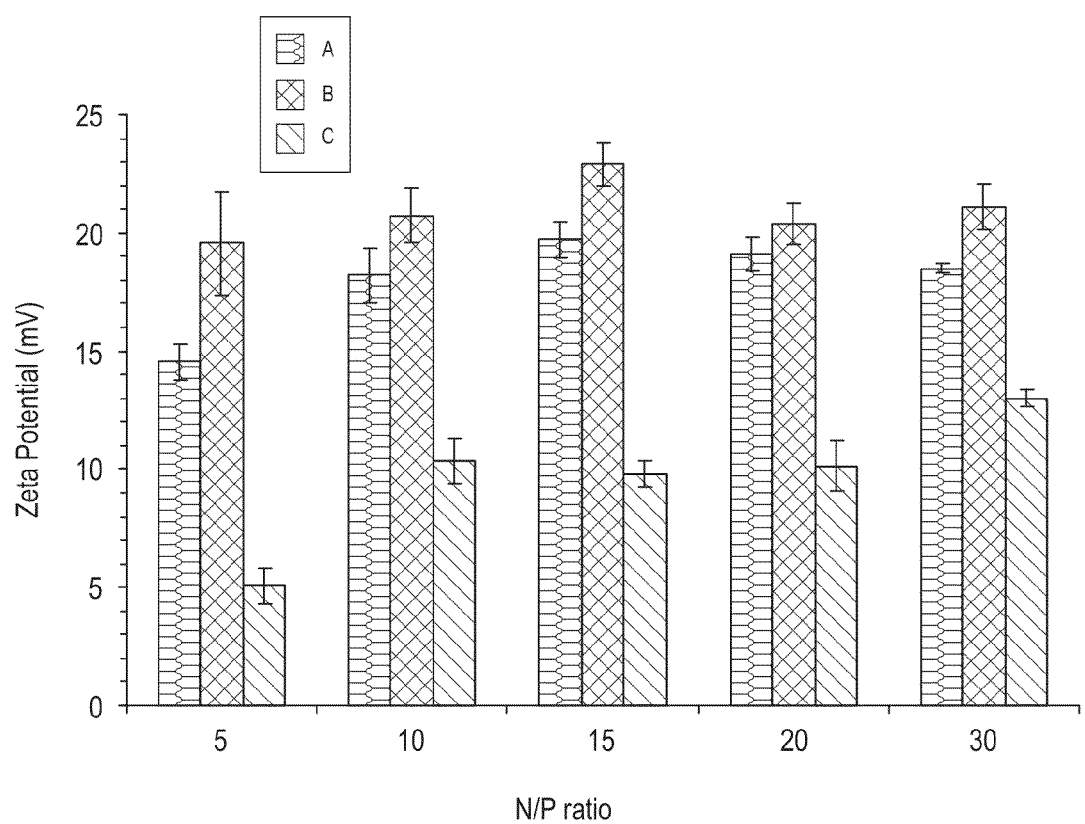
FIG. 5 is a bar graph showing the corresponding zeta-potentials at N/P 10 to 30 of the GFP reporter gene complexes of FIG. 1. A control bPEI-25/gene complex prepared at N/P 10 (not shown) had a particle size at about 84 nm and a zeta potential of about 22 mV.
Figure 6:
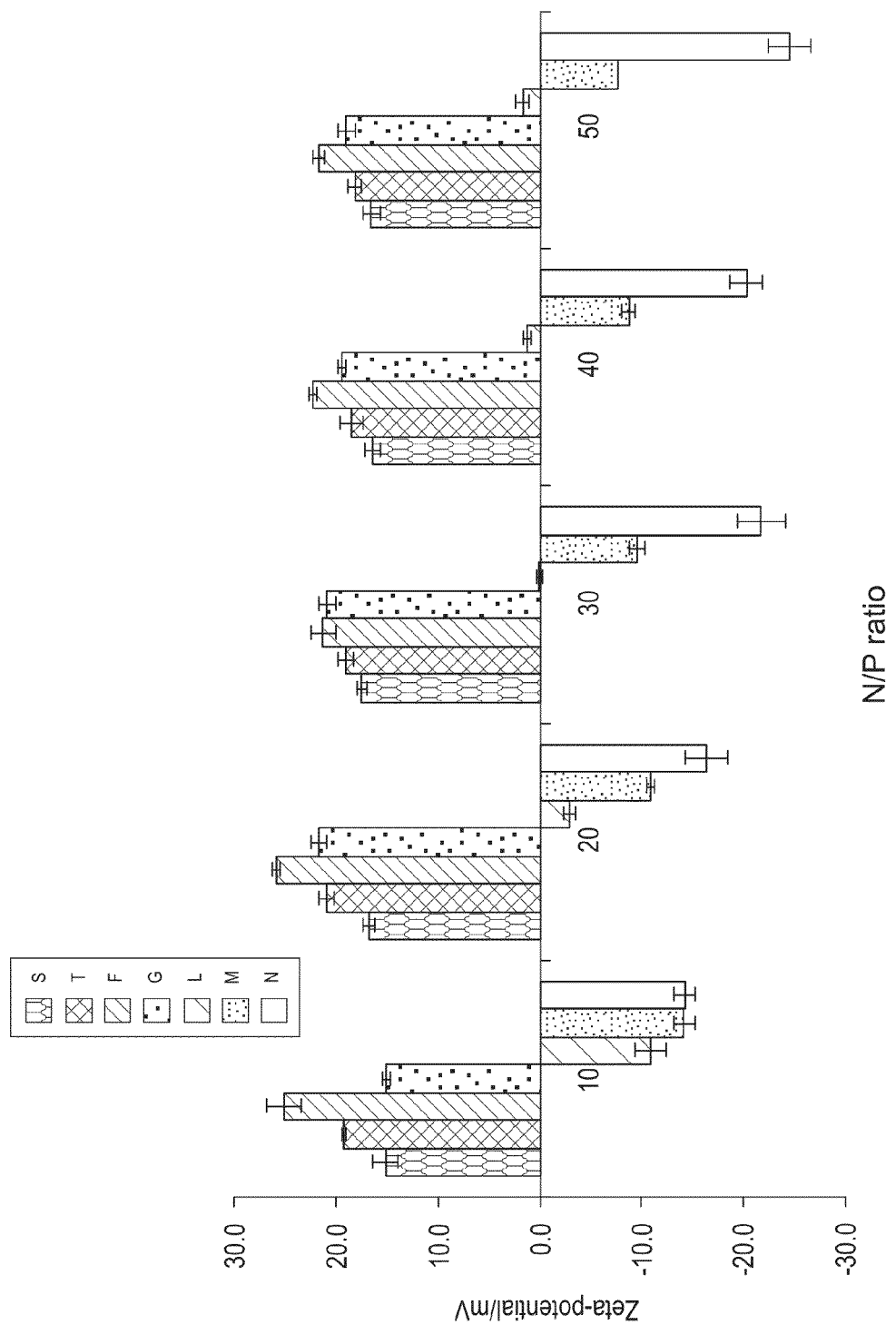
FIGS. 6-8 are bar graphs showing the zeta-potentials at N/P 10 to 50 of the carbamate functionalized bPEI-25/gene complexes of FIGS. 2 to 4, respectively.

The net positive charge of the gene complex affects the interaction of the complex with the negative charged phospholipid surface of the cell membrane, and therefore also affects gene transfection efficiency. FIG. 5 shows the zeta potentials of GFP reporter gene complexes of A, B, and C. FIG. 6 shows the zeta potential of luciferase reporter gene complexes of S, T, F, G, L, M, and N. The GFP gene complexes of A, B, S, T, F and G had cationic surface charge densities at N/P 10 to N/P 50 that were comparable in value to the GFP gene complex of non-modified bPEI-25. The luciferase gene complexes of S, T, F and G had cationic surface charge densities that were comparable or slightly lower in value compared to the non-modified bPEI-25/luciferase gene complex. Thus, the zeta potentials of the gene complexes of A, B, S, T, F, and G were in a range of 15 mV to about 26 mV, whereas the corresponding gene complex of bPEI-25 prepared at N/P 10 had a zeta potential of about 22 mV (bPEI-25/GFP) or 26 mV (bPEI-25/luciferase) (not shown).

The gene complexes of C (GFP), L (luciferase), M (luciferase) and N (luciferase) had a significantly lower cationic charge density on the surface at the same N/P ratios (FIGS. 5 and 6). The zeta potentials were 5 mV to 13 mV for C, −11 mV to 2 mV for L, −14 mV to −8 mV for M, and −25 mV to −14 mV for N complexes. Without being bound by theory, the gene complexes of polymers C, L, M, and N are believed to be less effective transfection agents due to their large particle size and low zeta potential.

Figure 7:
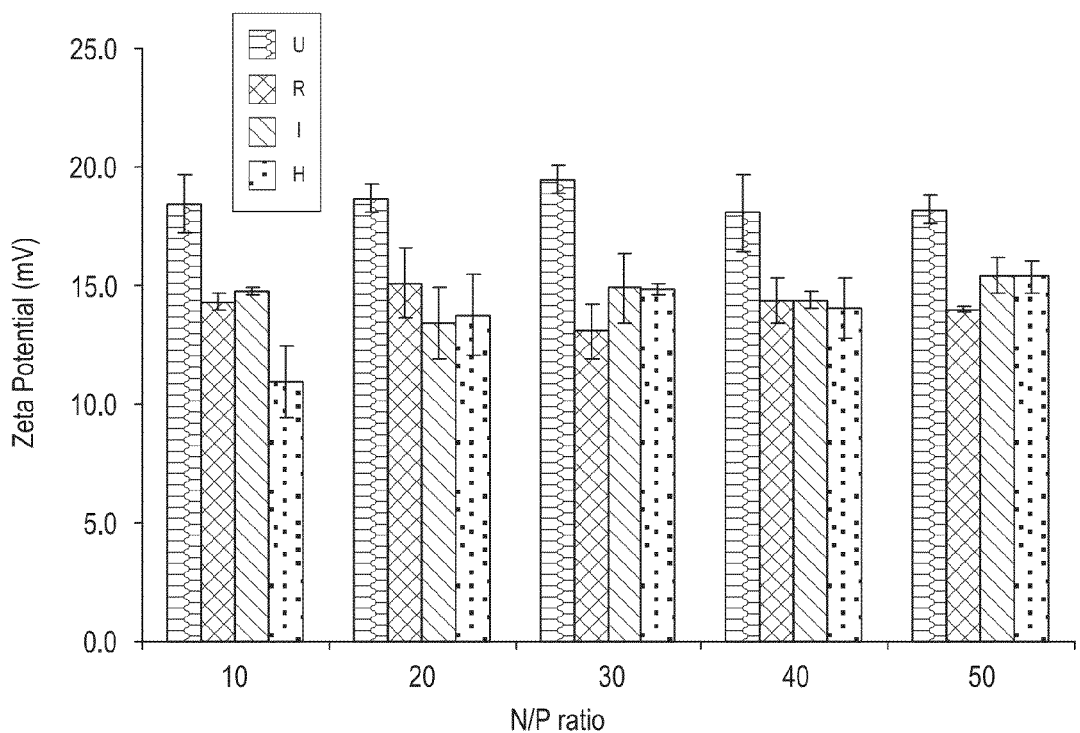
Figure 8:
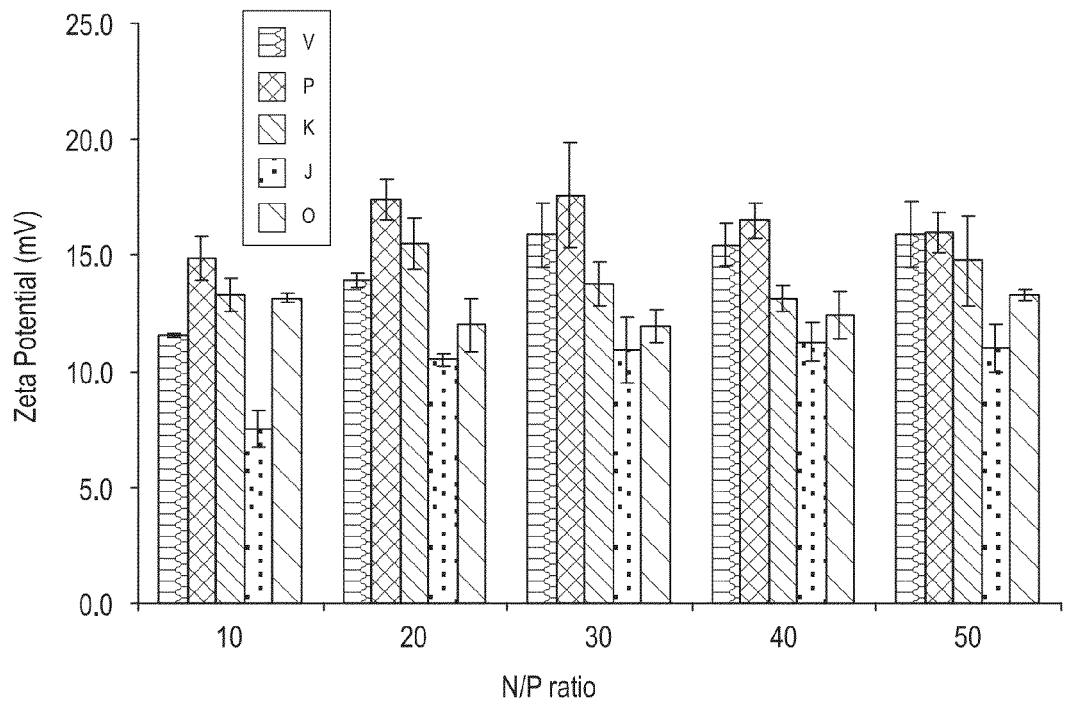

The zeta potentials of luciferase reporter gene complexes of I, R, U (galactose modified bPEI-25) and H (glucose modified bPEI-25) were between 7 and 20 mV at all N/P ratios (FIG. 7). These values are slightly lower than that obtained for the luciferase complex of non-modified bPEI-25/at N/P ratio of 10 (not shown). Similarly, the zeta potentials of luciferase reporter gene complexes of V, P, K, J, and O were between 7 and 20 mV at all N/P ratios (FIG. 8).

Gel Retardation Assay.

Various formulations of polymer/DNA complexes were prepared as described above with N/P ratios ranging from 1 to 30. Post equilibration, the DNA complexes were electroporated on 1% agarose gel. The agarose gel was stained with 5 microliters of 10 mg/mL ethidium bromide per 50 mL of agarose solution. The gel was run in 0.5×TBE buffer at 80 V for 50 min, and then analyzed under a UV illuminator (Chemi Genius, Evolve, Singapore) to reveal the relative position of the complexed DNA to the naked DNA plasmid.

Figure 9:
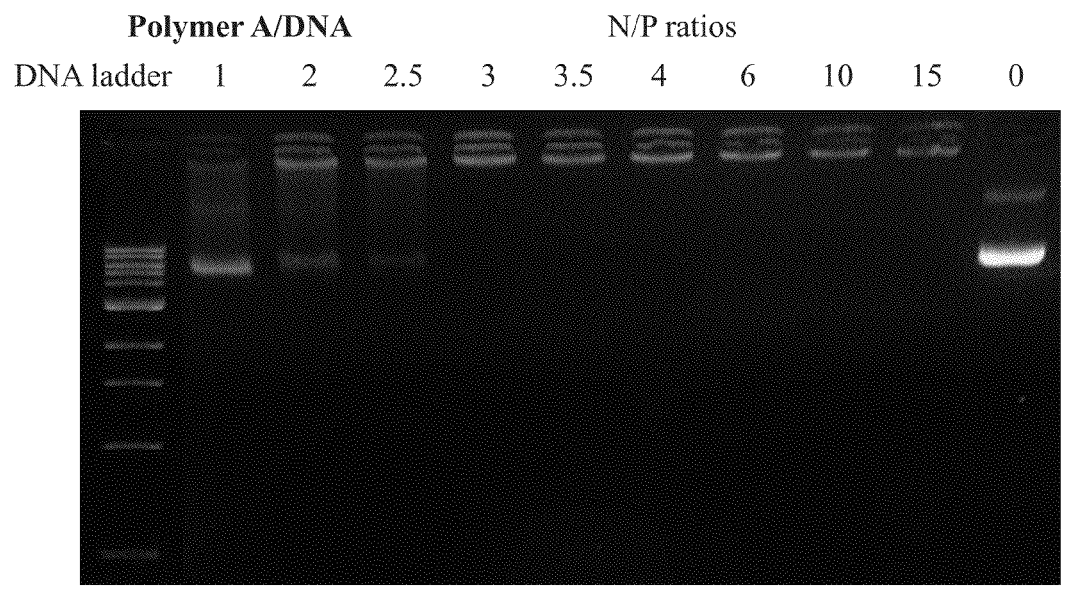
FIGS. 9-27 are photographs of a DNA ladders obtained for luciferase reporter gene complexes of carbamate functionalized bPEI-25 polymers A, B, C, F, G, S, T, L, M, N, U, R, I, H, V, P, K, J, and O, respectively.
Figure 10:
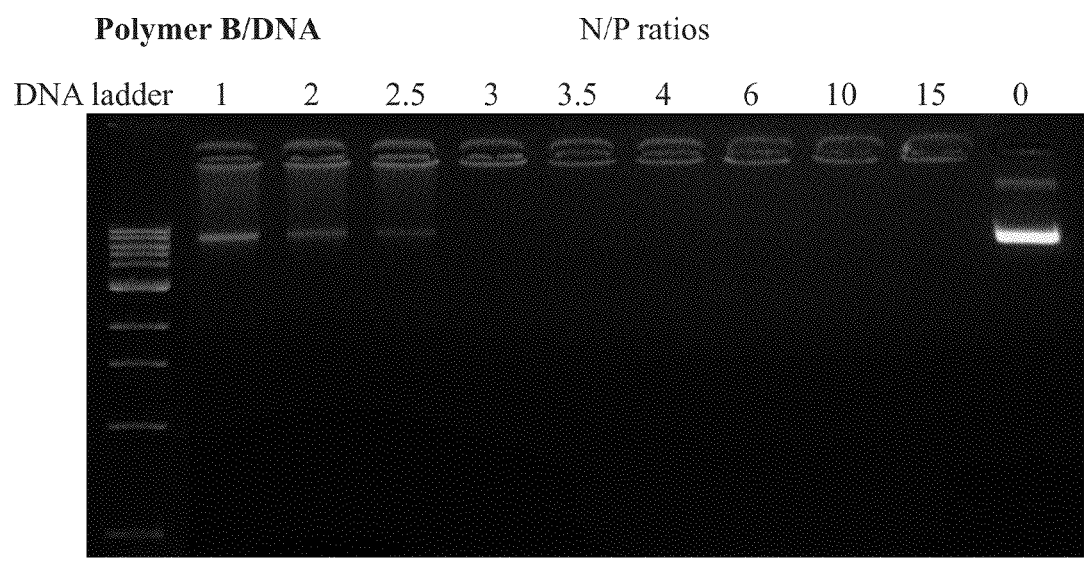
Figure 11:
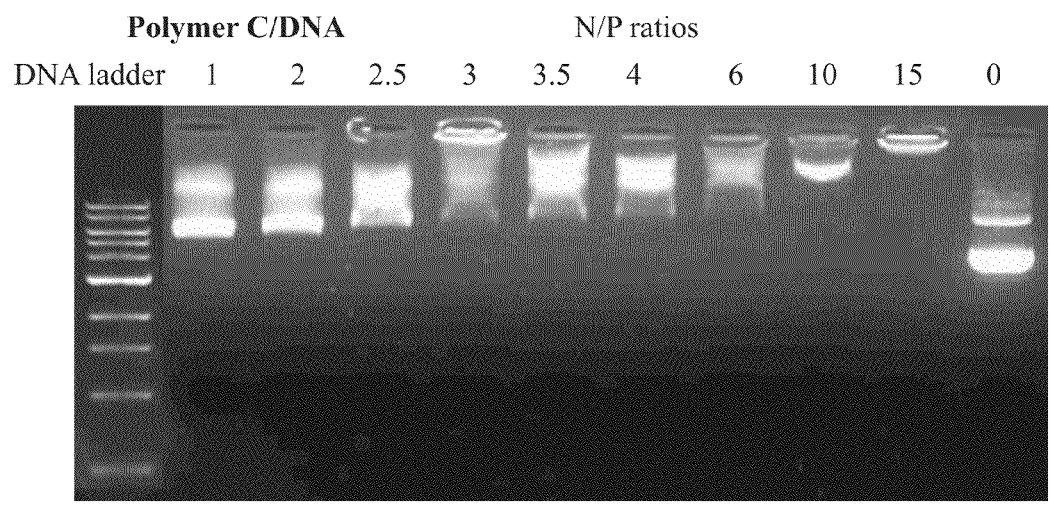
Figure 12:
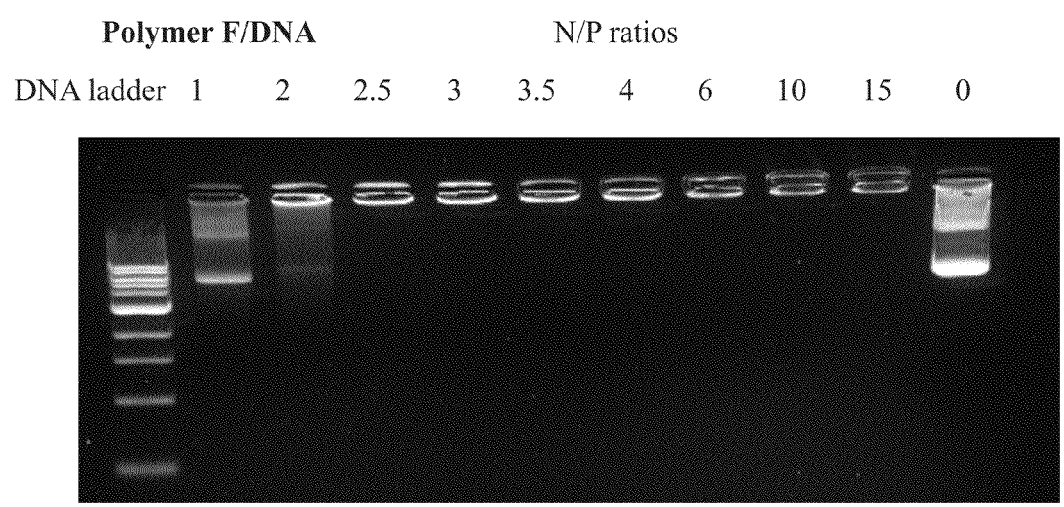
Figure 13:
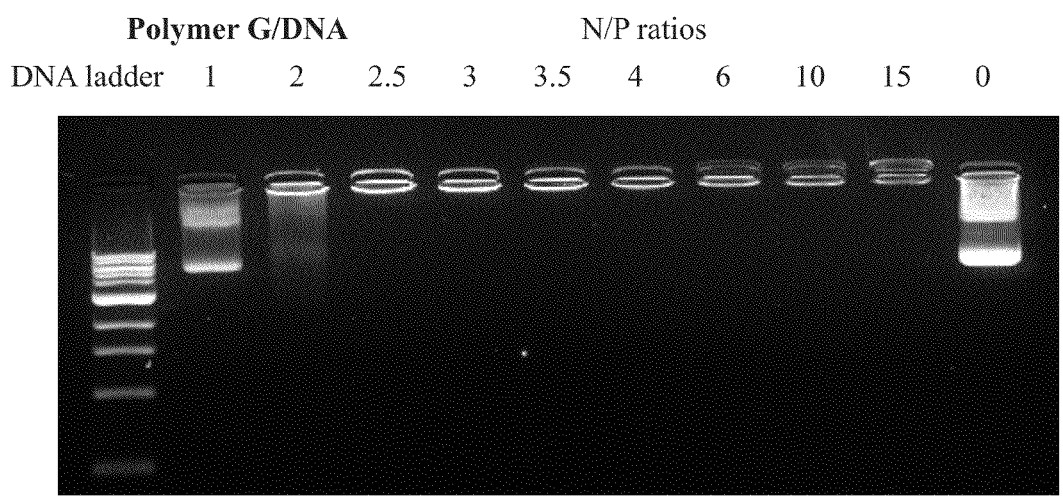
Figure 14:
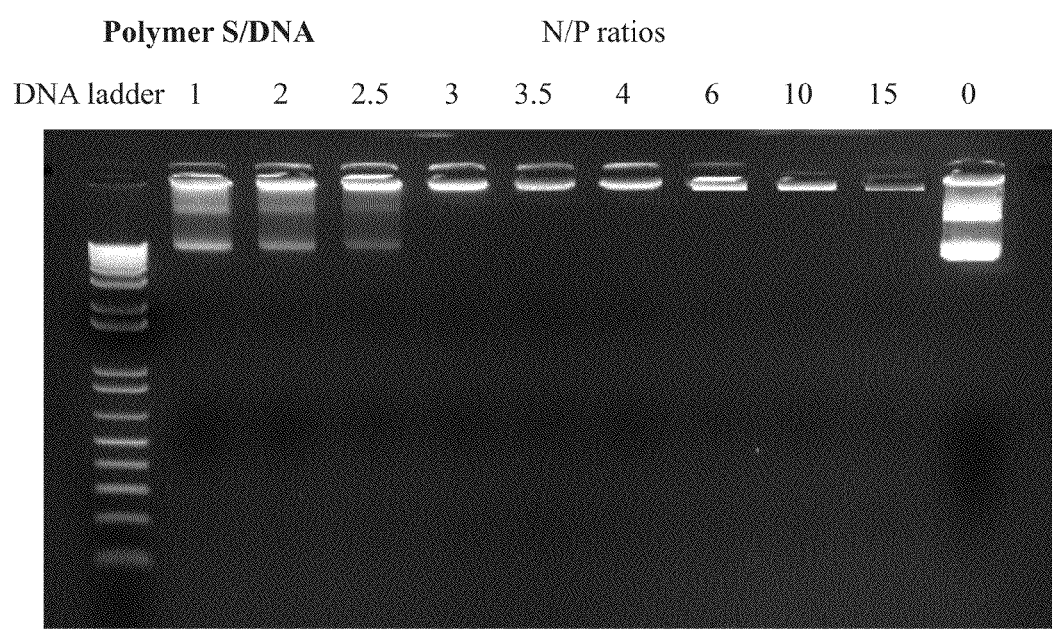
Figure 15:
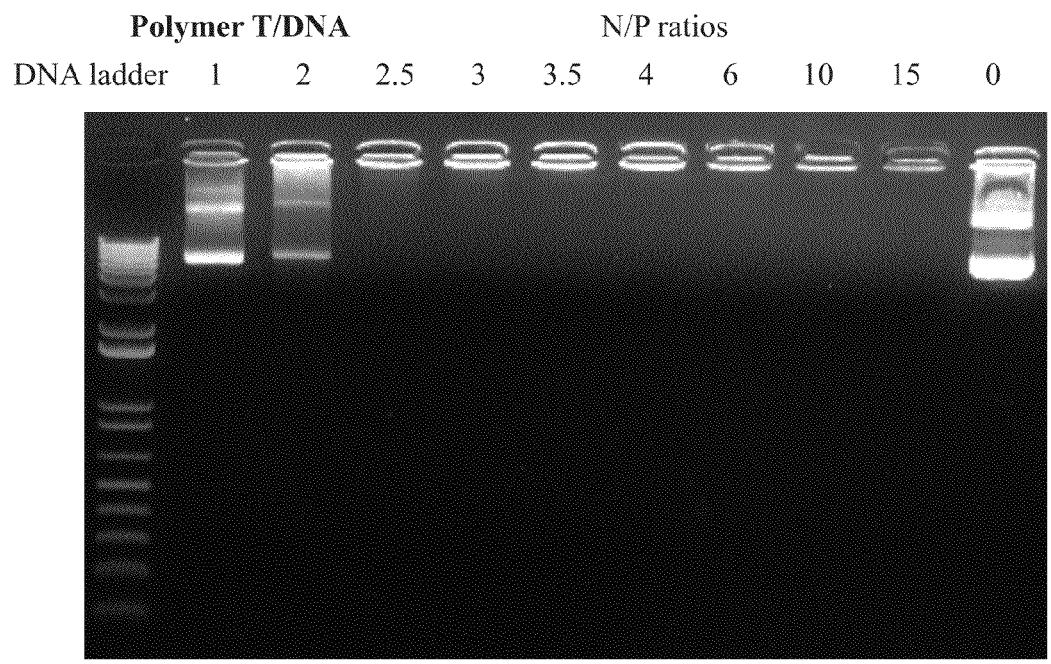
Figure 16:
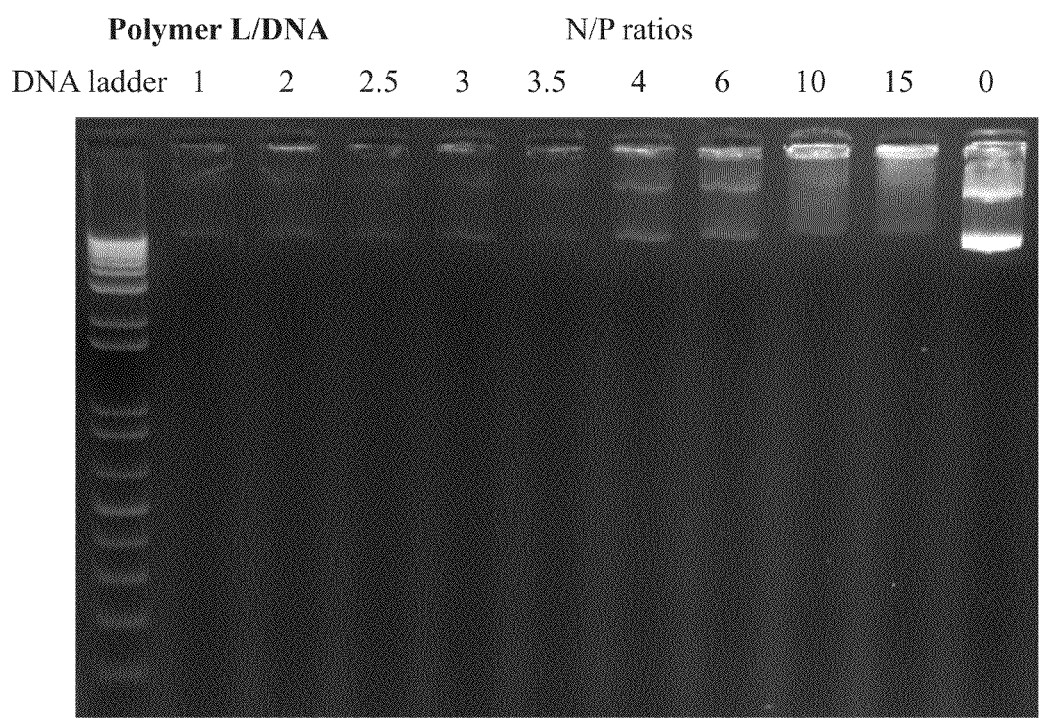
Figure 17:
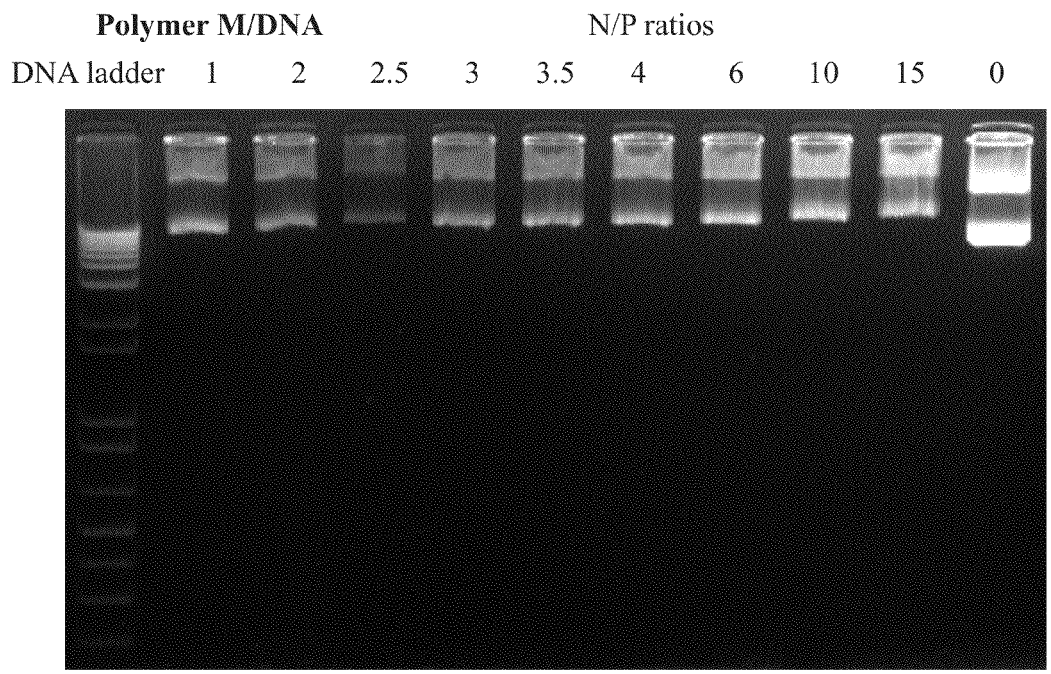
Figure 18:
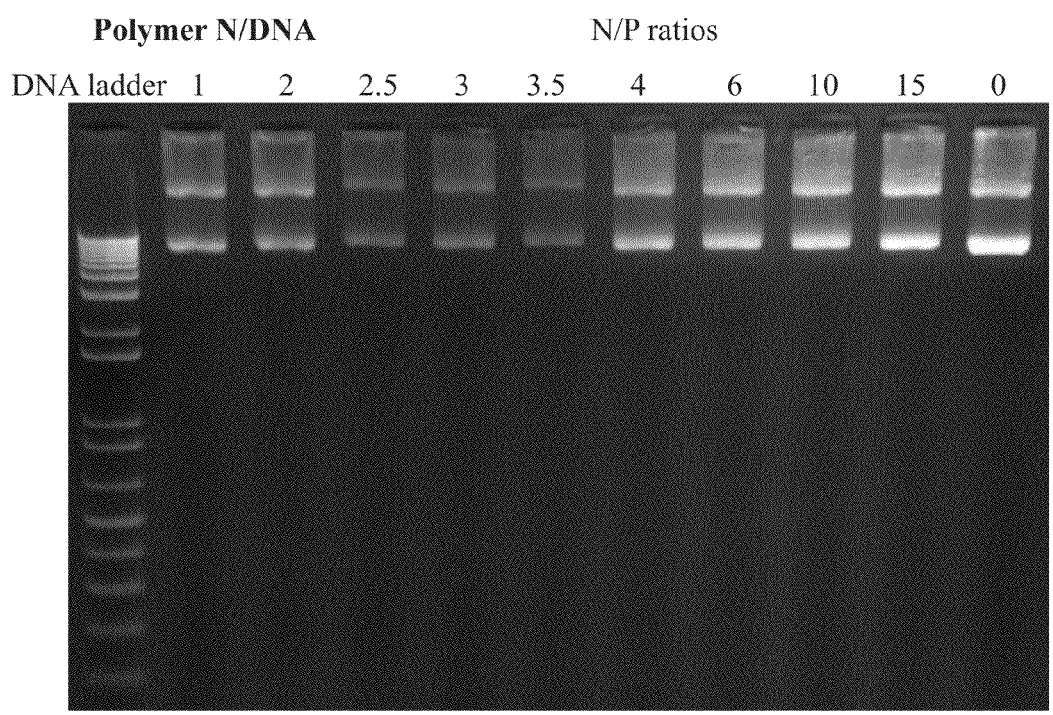
Figure 19:
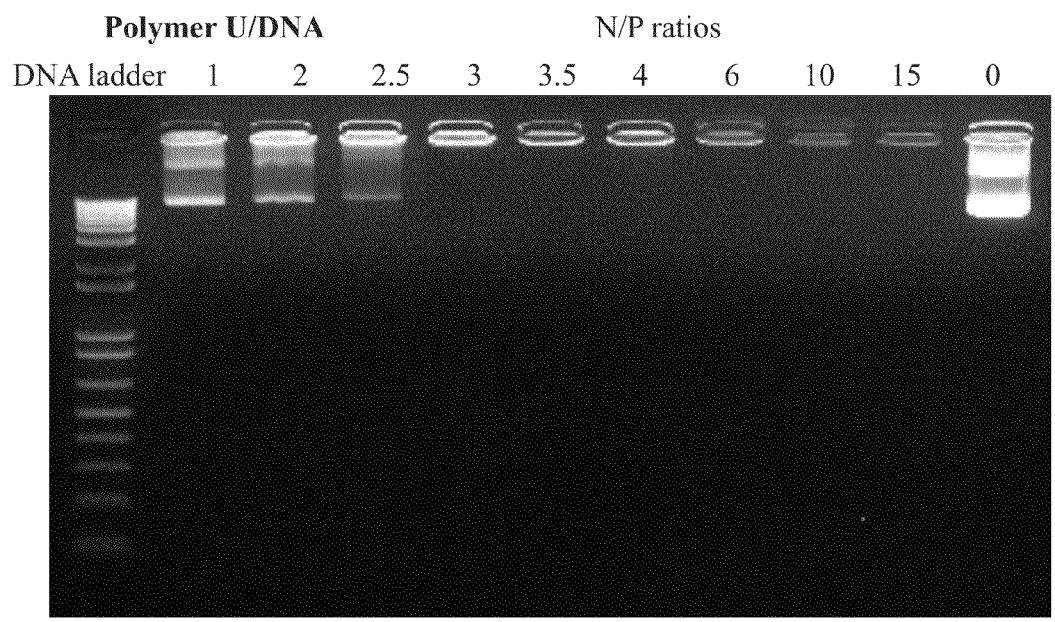
Figure 20:
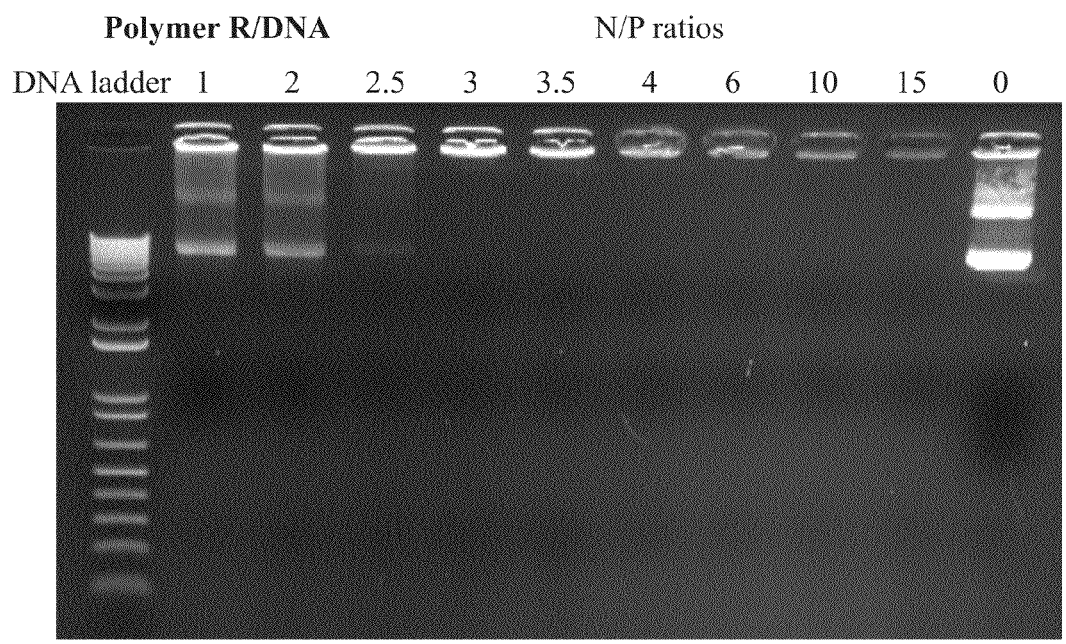
Figure 21:
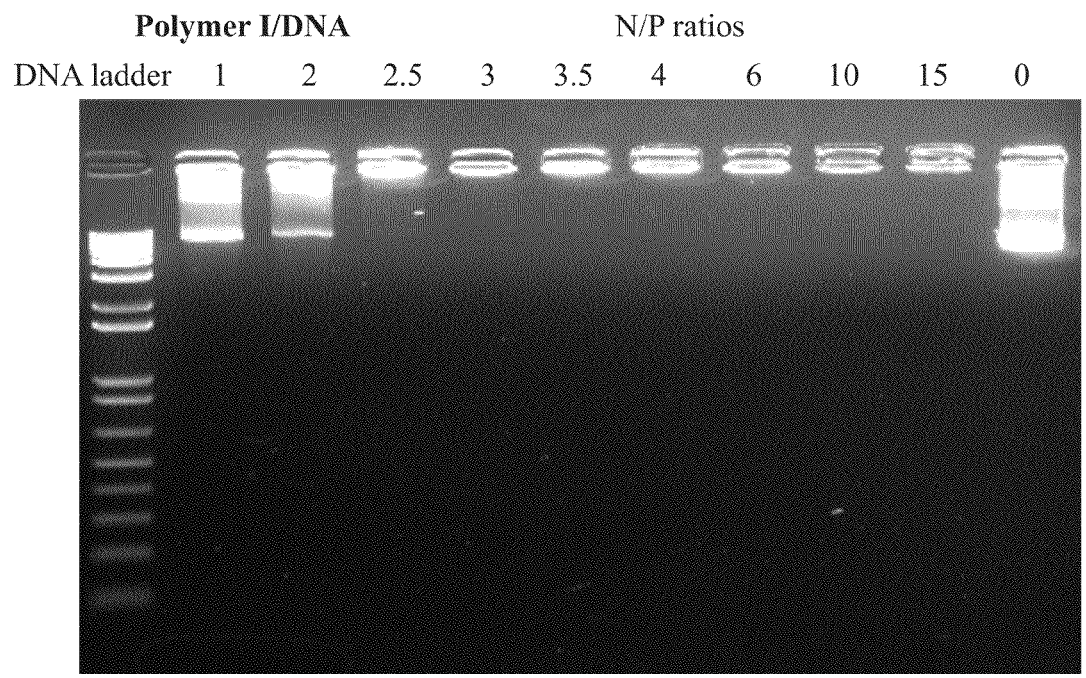
Figure 22:
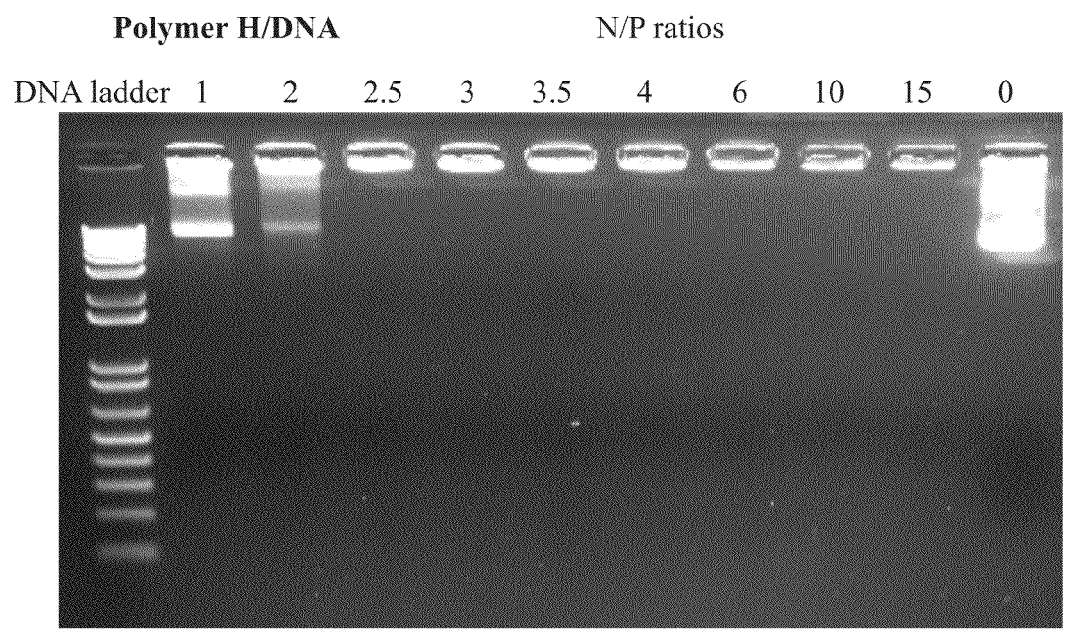
Figure 23:
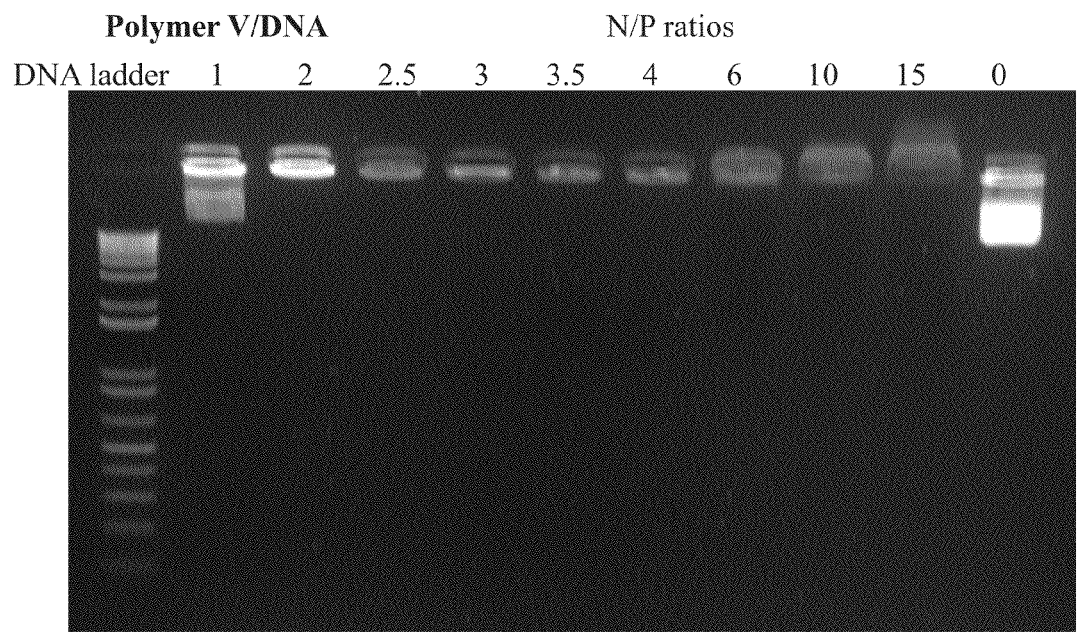
Figure 24:
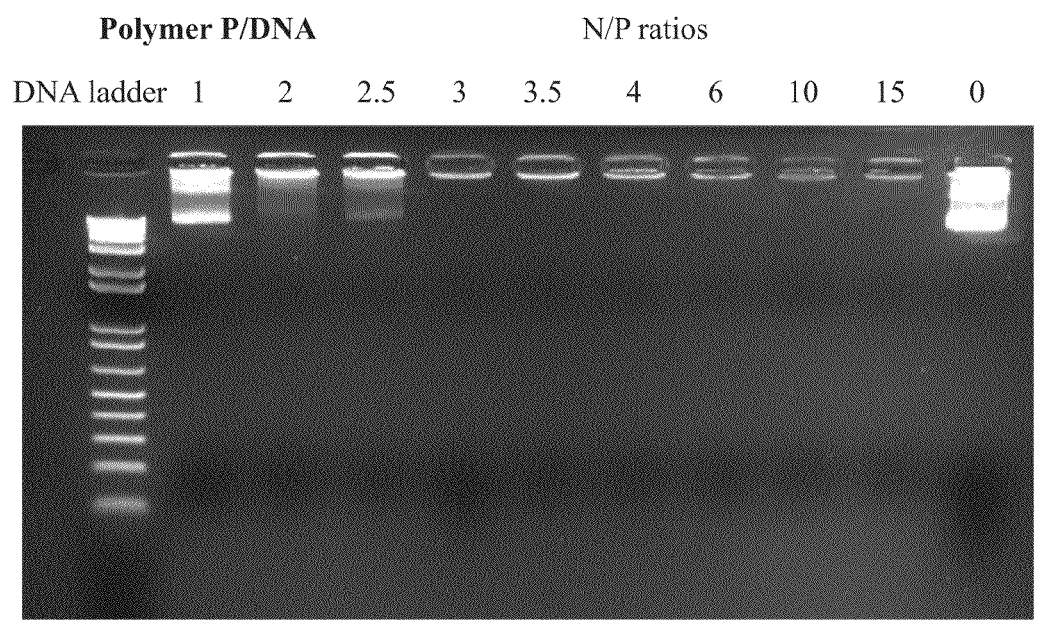
Figure 25:
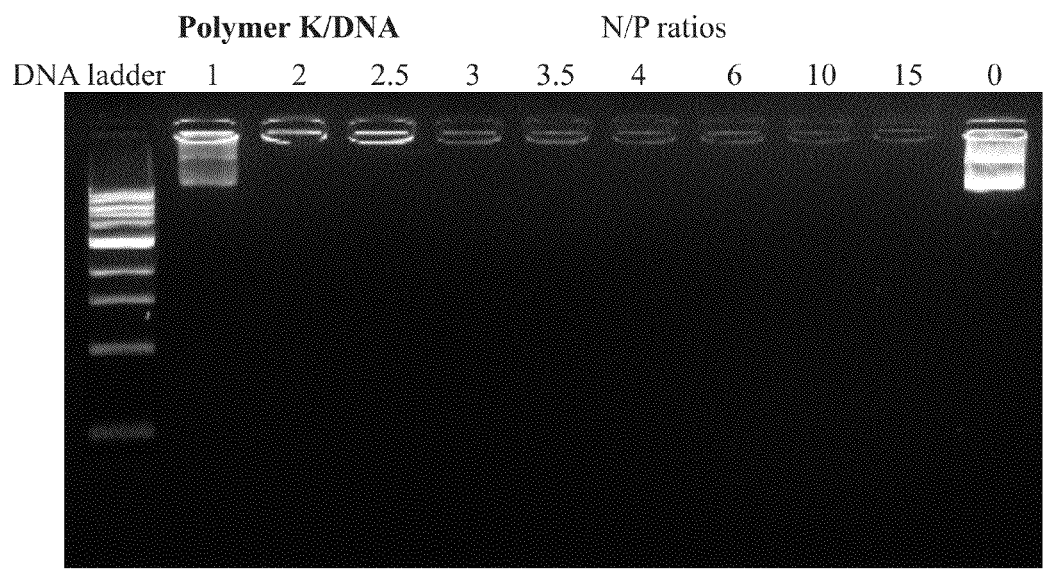
Figure 26:
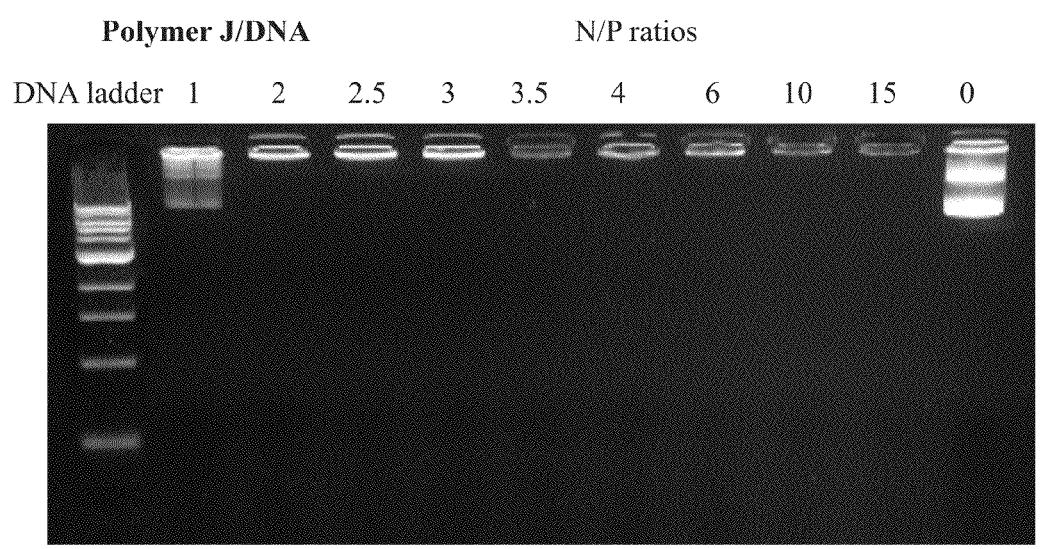
Figure 27:
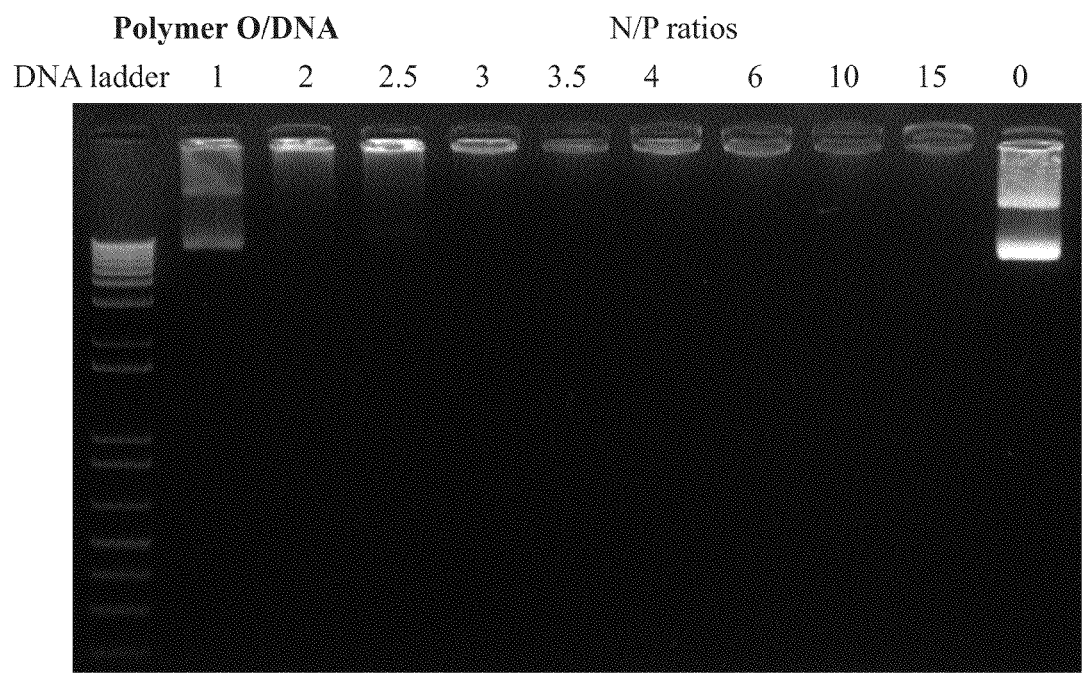

FIGS. 9 to 27 are photographs of DNA ladders of luciferase reporter gene complexes of various modified polymers: A (FIG. 9), B (FIG. 10), F (FIG. 12), G (FIG. 13), S (FIG. 14), T (FIG. 15), U (FIG. 19), R (FIG. 20), I (FIG. 21), H (FIG. 22), V (FIG. 23), P (FIG. 24), K (FIG. 25), J (FIG. 26), and O (FIG. 27) were able to effectively bind to and condense DNA, completely retarding DNA mobility in the complexes at or below N/P 3. By comparison, C (FIG. 11), L (FIG. 16), M (FIG. 17) and N (FIG. 18) had poor DNA binding ability, and complete DNA binding was observed only at N/P 15 for C. Even at N/P 30, polymers L, M and N could not bind to and condense DNA effectively (more amine groups were consumed for carbonate-mannose attachment).

Figure 28:
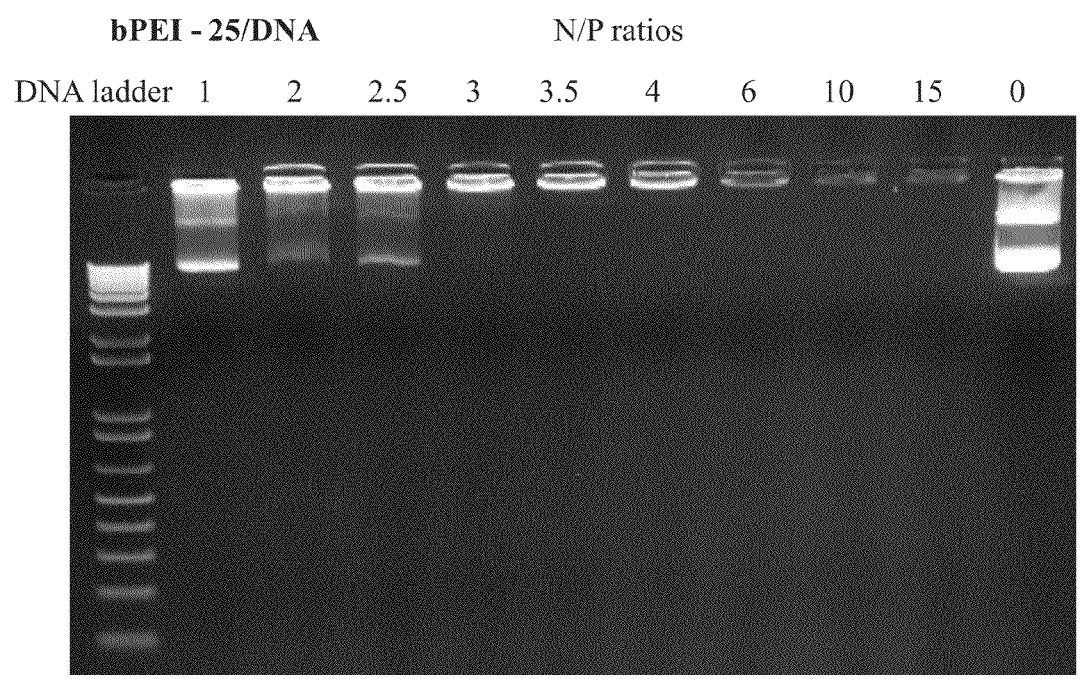
FIG. 28 is a photograph of a DNA ladder obtained for a luciferase reporter gene complex of bPEI-25.
Figure 29:
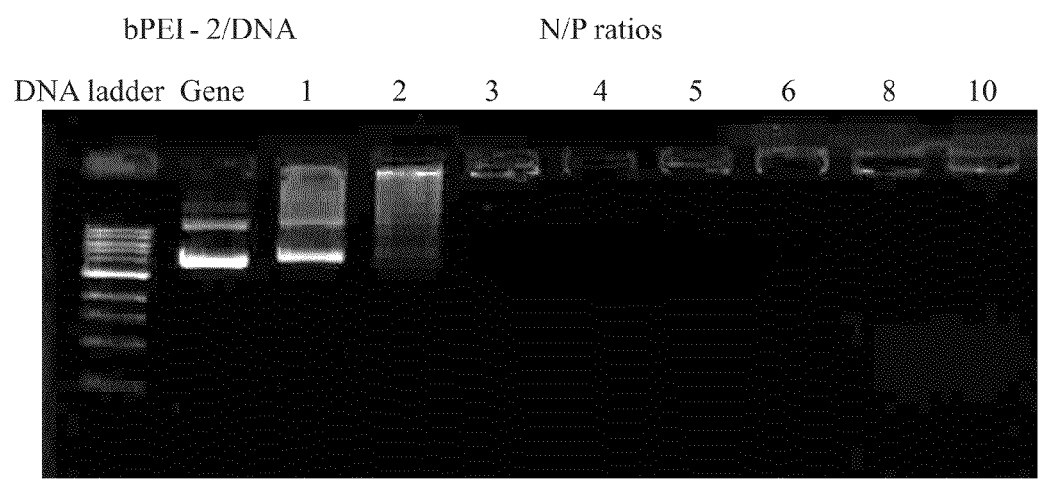
FIG. 29 is a photograph of a DNA ladder obtained for a luciferase reporter gene complex of bPEI-2 (Mw 2000, Mn 1800).

FIG. 28 is a photograph of a DNA ladder for non-modified bPEI-25/luciferase complex. FIG. 29 is a photograph of a DNA ladder for non-modified bPEI-2/luciferase complex. FIGS. 28 and 29 show that complete DNA binding was achieved with each complex at N/P ratio 3.

In Vitro Gene Expression.

The in vitro gene transfection efficiencies of the GFP reporter gene and luciferase gene complexes of modified bPEI-25 polymers were investigated using HepG2, HeLa and SK-OV-3 cell lines. HepG2 and HeLa cells were seeded onto 12-well plates at a density of $2\times10^5$ cells per 1000 microliters per well for GFP gene delivery. HepG2 cells were seeded onto 24-well plates at a density of $1\times10^5$ cells per 500 microliters per well for luciferase gene delivery. SK-OV-3 cells were seeded onto 24 well plates at a density of $8\times10^4$ cells per 500 microliters per well for luciferase gene delivery. After 24 hours, the plating media were replaced with fresh growth media, followed by the drop-wise addition of 100 microliters of complex solution (containing 3.5 micrograms GFP plasmid DNA) or 50 microliters of complex solution (containing 2.5 micrograms luciferase plasmid DNA) at various N/P ratios. Following 4 hours of incubation, free complexes were removed by replacing the medium in each well. After a further 68 hours of incubation, the cell culture medium in each well was removed and the cells rinsed once with 0.5 mL of phosphate-buffered saline (PBS, pH 7.4).

For GFP protein expression analysis, 0.3 mL trypsin was added to detach cells in each well. Fresh growth medium (0.3 mL) was then added, and the cell suspension was centrifuged at 1500 rpm for 5 min. Two further cell-washing cycles of re-suspension and centrifugation were carried out in FACS buffer (PBS supplemented with 2% bovine serum albumin). The percentage of cells expressing GFP was then determined using a flow cytometer (FACSCalibur, BD Biosciences, USA) from 10000 events, and reported as mean±standard deviations of triplicates.

For luciferase expression assay, 0.2 mL of reporter lysis buffer was added to each well. The cell lysate collected after two cycles of freezing (−80° C., 30 min) and thawing was cleared by centrifugation at 14000 rpm for 5 min, after which 20 microliters of supernatant was mixed with 100 microliters of luciferase substrate for the determination of relative light units (RLU) using a luminometer (Lumat LB9507, Berthold, Germany). The RLU readings were normalized against the protein concentration of the supernatant determined using the BCA protein assay to give the overall luciferase expression efficiency. In all in vitro gene expression experiments, naked DNA was used as a negative control. Non-modified bPEI-25/gene complex and in some instances non-modified bPEI-2/gene complex were used as the positive control. These controls were prepared at the optimal N/P ratio (i.e., N/P 10 for bPEI-25, N/P 40 for bPEI-2), which induced high gene expression efficiency yet provided close to or more than 50% cell viability. Data were expressed as mean±standard deviations of four replicates.

The following procedures were used for siRNA transfection and real-time reverse transcription-polymerase chain reaction (RT-PCR) analysis. The in vitro siRNA delivery property of the polymers was investigated using HeLa cell line. Cells were seeded onto 12-well plates at a density of $1\times10^5$ cells per 1000 microliters per well. After 24 hours, the plating media were replaced with fresh growth media, followed by the drop-wise addition of 100 microliters of complex solution (containing 100 nM bcl-2 siRNA or negative control siRNA complexed with various polymers) at N/P ratio of 50. Following 4 hours of incubation, free complexes were removed by replacing the medium in each well. After a further 68 hours of incubation, the cell culture medium in each well was removed and the cells were subjected to RNA extraction.

Each condition was performed in duplicate to ensure the reproducibility of the results, and each sample was taken from an individual well of a 12 well plate. Total RNA from untreated HeLa cells or those transfected with polymer/bcl-2 siRNA or the negative control siRNA was extracted with RNeasy® Mini Kit (Qiagen, Singapore) according to the RNeasy® Mini Handbook. The total RNA was then reverse-transcribed by SuperScript™ III Reverse Transcriptase (Invitrogen, Singapore) using oligo(dT)$_{18}$ primer according to the manufacturer's instructions. The resulting cDNA was subjected to real-time PCR reaction, which was performed with SYBR® Green PCR master mix (2×) (Stategene, Singapore) and detected with Rotorgene 6000 (Corbett Research). Custom primers were purchased for Bcl-2 (target gene) and β-Actin (endogenous control), with sequences as follows: Bcl-2: sense 5'-CGACGACTTCTCCCGCCGC-TACCGC-3' (SEQ ID NO:3), antisense 5'-CCGCAT-GCTGGGGCCGTA CAGTTCC-3' (SEQ ID NO:4); 13-Actin, sense 5'-GCTCGTCGTCGACAACGGCTC-3' (SEQ ID NO:5), antisense 5'-CAAACATGATCTGGGTCATCT-TCTC-3' (SEQ ID NO:6). β-Actin primer sequence is based on Invitrogen primers provided with the Superscript III reverse-transcription kit, and yields a 353-bp product. Custom Bcl-2 primer is based on the literature (Huang, et al., Acta Pharmacologica Sinica, 2006 February; 27 (2): 242-248). A 25 microliter reaction mixture contained 12.5 microliters of SYBR® Green I PCR master mix (2×), 10 micromoles of each primer, 9.5 microliters of DEPC-treated water, and 2 microliters of cDNA sample. Reaction conditions were set as follows: (1) incubation at 95° C. for 10 min; (2) amplified for 45 cycles (95° C. for 45 sec, 55° C. for 45 sec, 72° C. for 90 sec for each cycle); (3) 1 cycle of 72° C. for 7 min for final extension; (4) ramp from 72° C. to 95° C., 1 degree change per step, 5 sec interval between steps. The mean fold change of Bcl-2 gene expression level upon various treatments was normalized against the house-keeping gene β-Actin using the $2^{-\Delta CT}$ method (Livak, et al., Methods, 25, 402-408 (2001)).

Figure 34:
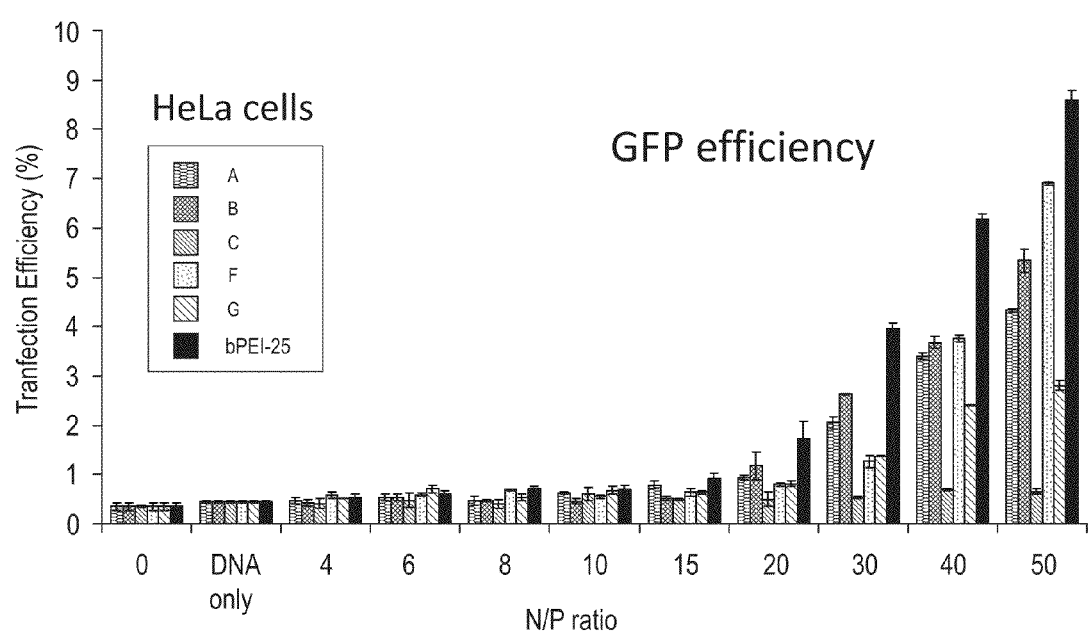
FIG. 34 is a bar graph showing the GFP transfection efficiency in HeLa cells as a function of N/P of GFP reporter gene complexes prepared with carbamate functionalized bPEI-25 polymers A, B, C, F, and G. The transfection efficiency of the gene alone (labeled DNA only) and a control complex prepared with bPEI-25 are also shown.

FIGS. 30 to 33 are bar graphs depicting the in vitro GFP gene transfection efficiency in HepG2 cells mediated by various modified bPEI-25 polymers at various N/P ratios. FIG. 34 is a bar graph depicting the in vitro GFP gene transfection efficiency in HeLa cells mediated by various modified bPEI-25 polymers at various N/P ratios. Results represent mean±standard deviation of triplicates. Polymer concentrations (mg/L) in the order of N/P ratios specified are as follows: non-modified bPEI-25—0, 0.8, 1.6, 2.4, 3.2, 4.0, 6.0, 8.0, 12.0, 16.0 and 20.0 mg/L; A, F, G, H, I, J—0, 3.3, 4.9, 6.6, 8.2, 12.3, 16.4, 24.6, 32.8 and 41.0 mg/L; B—0, 2.2, 3.3, 4.4, 5.5, 8.2, 11.0, 16.4, 21.9 and 27.4 mg/L; C—0, 6.6, 9.9, 13.1, 16.4, 24.6, 32.8, 49.3, 65.7 and 82.1 mg/L. K—0, 2.1, 3.1, 4.1, 5.2, 7.7, 10.3, 15.5, 20.6 and 25.8 mg/L; L—0, 4.4, 6.7, 8.9, 11.1, 16.7, 22.2, 33.3, 44.4, and 55.5 mg/L; M—0, 9.5, 14.3, 19.1, 23.9, 35.8, 47.7, 71.6, 95.5, and 119.3 mg/L; N—0, 28.1, 42.2, 56.3, 70.3, 105.5, 140.7, 211.0, 281.3, and 351.7 mg/L; T, U—0, 2.0, 3.1, 4.1, 5.1, 7.7, 10.2, 15.3, 20.4, 25.5 mg/L; R, S—0, 2.5, 3.7, 4.9, 6.2, 9.2, 12.3, 18.5, 24.6, and 30.8 mg/L; V—0, 1.7, 2.5, 3.3, 4.2, 6.2, 8.3, 12.5, 16.6, and 20.8 mg/L; P—0, 1.8, 2.7, 3.6, 4.5, 6.7, 8.9, 13.4, 17.8, and 22.3 mg/L; O—0, 2.4, 3.6, 4.8, 6.0, 9.1, 12.1, 18.1, 24.2, and 30.2 mg/L. P43—0, 2.7, 4.0, 5.3, 6.7, 10.0, 13.4, 20.0, 26.7, and 33.4 mg/L; P44—0, 3.0, 4.5, 5.9, 7.4, 11.1, 14.8, 22.3, 29.7, and 37.1 mg/L.

Figure 30:
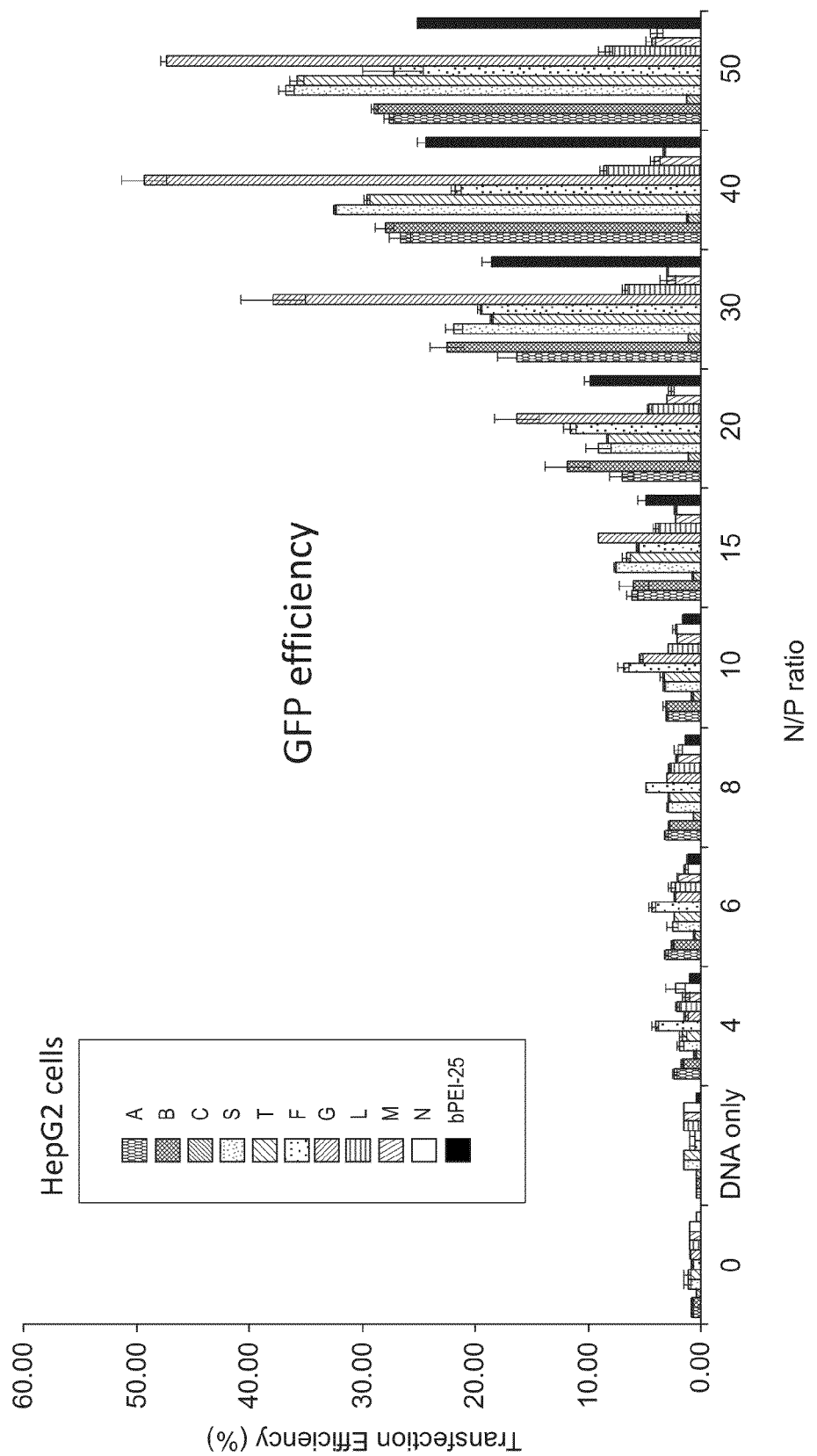
FIGS. 30-32 are bar graphs showing the GFP transfection efficiency in HepG2 cells as a function of N/P ratio of various carbamate functionalized bPEI-25 polymer complexes prepared with GFP reporter gene. The transfection efficiency of the gene alone (labeled DNA only) and a control complex prepared with bPEI-25 are also shown.

As shown in the bar graph of FIG. 30, GFP complexes of some of the mannose modified bPEI-25 polymers (A, B, S, T, and G) achieved high GFP transfection efficiency in HepG2 cells (about 20% to about 50%). Generally, increasing N/P ratio led to higher transfection efficiency. A control GFP reporter gene complex of non-modified bPEI-25 had 4.8% efficiency at N/P 15 and reached a plateau of about 25% efficiency at N/P 40 and 50. At N/P ratios below 30, A and B, which have more unreacted amine groups after MTC-IP-MAN attachment, had GFP transfection efficiencies that were comparable to non-modified bPEI-25. At N/P 30-50, the GFP transfection efficiencies of polymers A and B exceeded non-modified bPEI-25. GFP complexes of C, L, M and N had much lower transfection efficiency compared to non-modified bPEI-25 due to their large particle size, large size distribution, and low cationic charge density on the surface. Among all mannose-modified polymers, S, T and G showed the highest GFP transfection efficiencies (37%, 36% and 47% at N/P 50, respectively) exceeding the non-modified bPEI-25 at all N/P ratios tested (FIG. 30).

Figure 31:
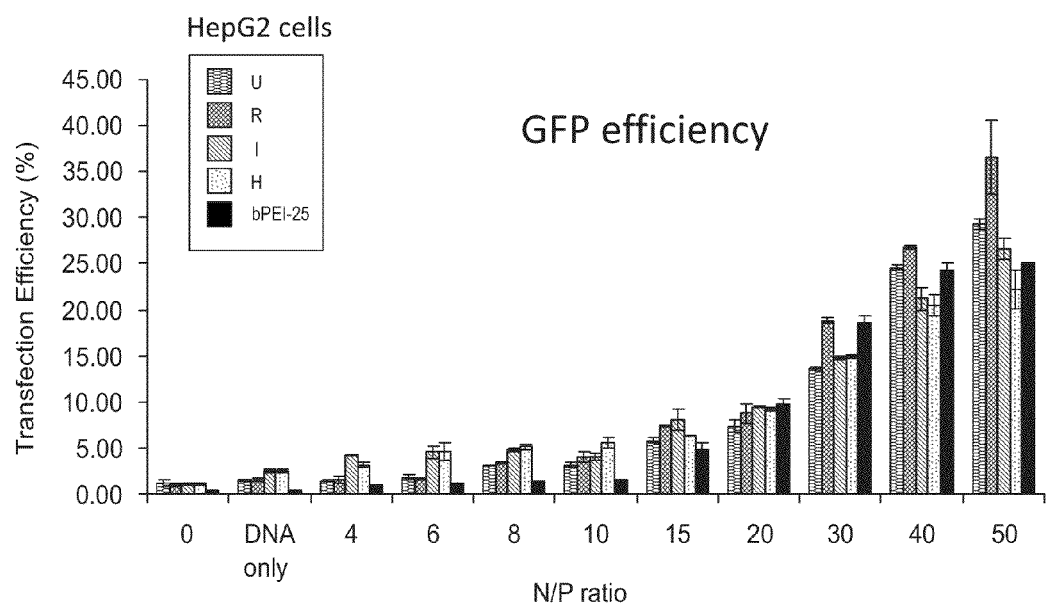

Of the glucose and galactose modified bPEI-25 polymers, polymer R (bPEI-25:Galactose=1:12.5) achieved the highest GFP transfection efficiency (37%) at N/P 50. Polymers U (bPEI-25:Galactose=1:6), I (bPEI-25:Galactose=1:25), H (bPEI-25:Glucose=1:25) had GFP transfection efficiencies comparable to that of non-modified bPEI-25 (FIG. 31).

Figure 32:
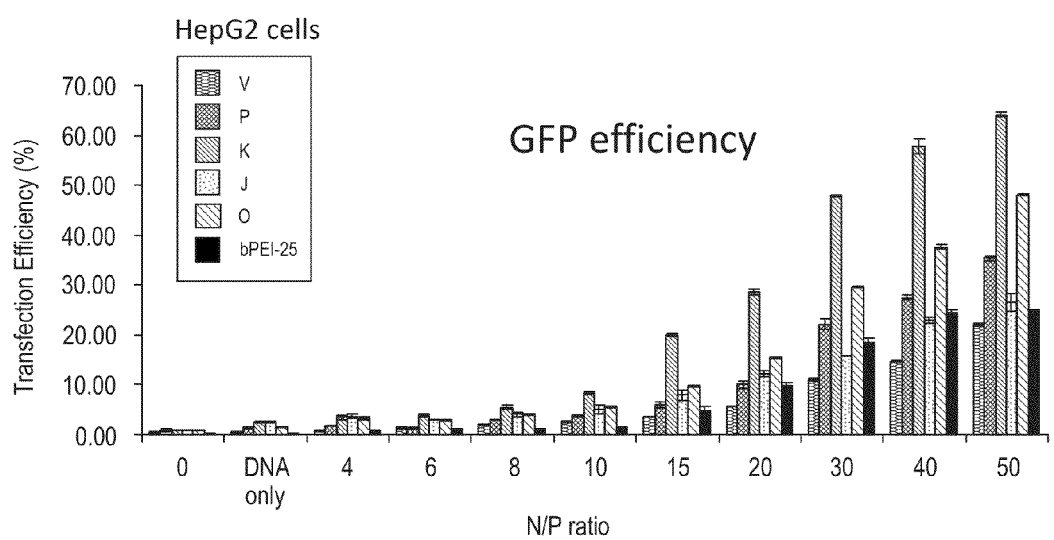
Figure 33:
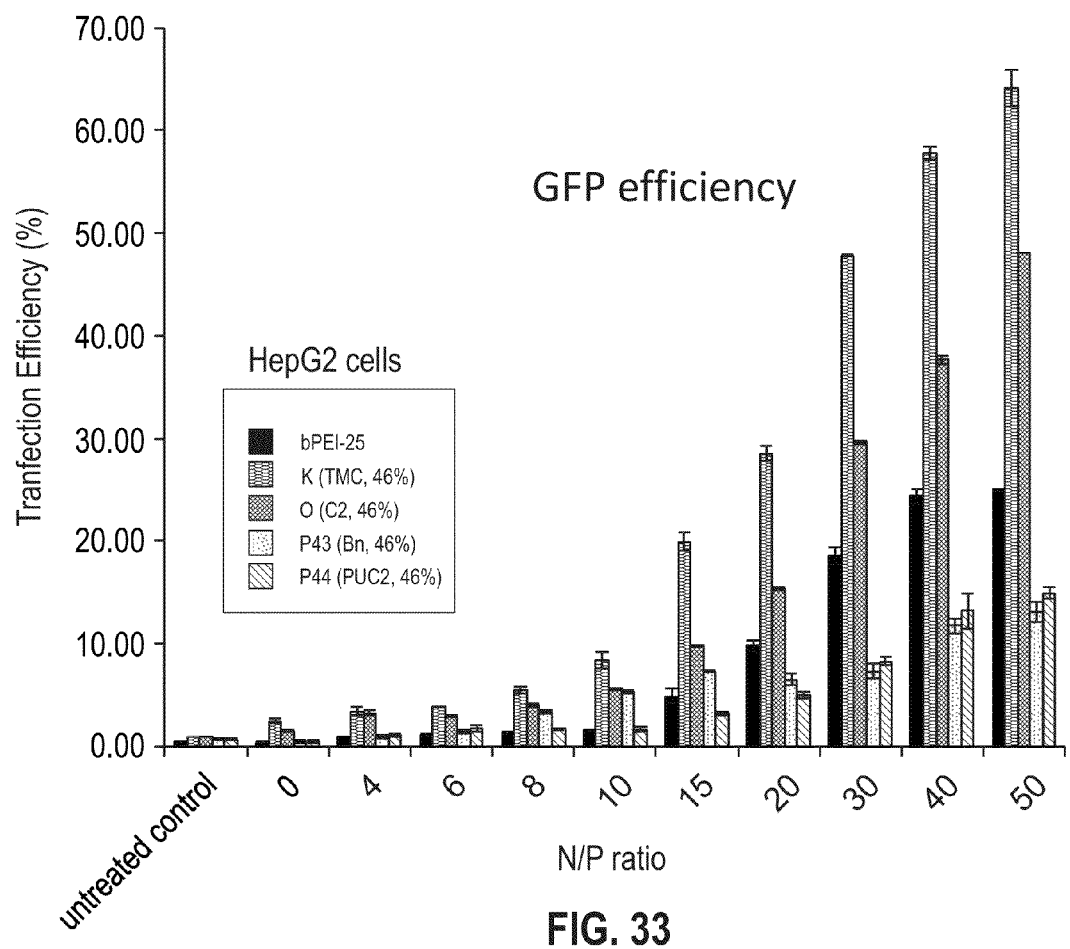
FIG. 33 is a bar graph showing the GFP transfection efficiency in HepG2 cells as a function of N/P of GFP reporter gene complexes prepared with carbamate functionalized bPEI-25 polymers O, K, P43, and P44. P43 has a benzyl ester and P44 has a 2-phenylurea ethyl ester group.

As shown in FIG. 32, modified bPEI-25 polymers P, K, and O prepared with hydrophobic cyclic carbonyl monomers (TMC and MTC-C2) had greatly enhanced GFP transfection efficiency in HepG2 cells compared to non-modified bPEI-25, especially polymer K (bPEI-25:TMC=1:25), whose transfection efficiency at N/P 50 reached 64%, currently the highest value achieved among all the polymers. Polymers P (bPEI-25:TMC=1:8) and O (bPEI-25:MTC-C2=1:25) had GFP transfection efficiencies of 35% and 48% at N/P 50, respectively. Polymers J (bPEI-25:TMC=1:100) and V (bPEI-25:TMC=1:1) had comparable GFP transfection efficiency (22-26%) to non-modified bPEI-25 at N/P 50.

Modified bPEI-25 polymers comprising a benzyl ester or a phenyl urea containing ester in the carbamate group had lower GFP transfection efficiencies in the HepG2 cell line (FIG. 33) compared to non-modified bPEI-25. Thus, polymer P43 (benzyl ester, 46% of the primary amine groups modified) and polymer P43 (phenyl urea ester, 46% of the primary amine groups modified) had GFP transfection efficiencies of about 12% and about 15% respectively at N/P 50.

GFP Transfection Efficiency in HeLa Cells.

In HeLa cells, the GFP reporter gene complex of non-modified bPEI-25 had higher GFP transfection efficiency (8-9%) compared to complexes of modified bPEI-25 polymers A, B, C, F, and G (FIG. 34). Polymer F had the highest GFP transfection efficiency of 6.9% at N/P 50 in HeLa cells. However, at N/P 50, non-modified bPEI-25 was also highly cytotoxic compared to polymer F (FIG. 40) at N/P 20 to 50. When GFP transfection efficiencies are compared at comparable cell viability, non-modified bPEI-25 had much lower transfection efficiency (<2% at N/P 20) (FIG. 34).

GFP Transfection Efficiency in SK-OV-3 Cells.

Figure 35:
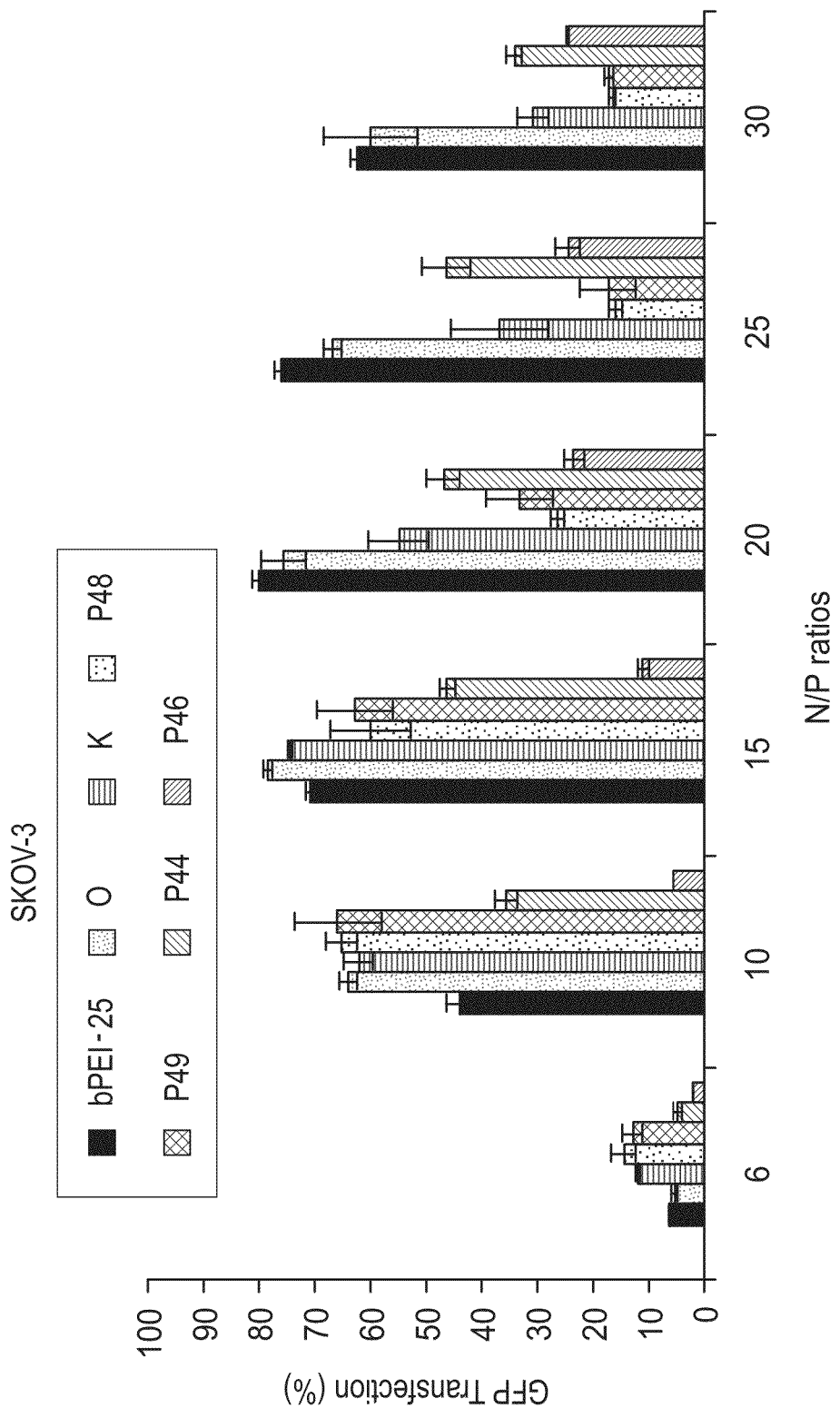
FIG. 35 is a bar graph showing the GFP transfection efficiency in SK-OV-3 cells as a function of N/P ratio for GFP reporter gene complexes of carbamate functionalized bPEI-25 polymers O, K, P44, P46, P48 to P49. P44 has an aromatic urea group. P46 has a cholesteryl group.

FIG. 35 compares the GFP transfection efficiencies of modified bPEI-25 polymers O, K, and P44, P46, P48, and P49 in the SK-OV-3 cell line. At N/P 10, the efficiencies of O, K, P48, and P49 (60% to 68%) exceeded non-modified bPEI-25 (45%). At N/P 15, polymers O and K had slightly higher GFP transfection efficiencies (about 72% and about 78%, respectively) compared to non-modified bPEI-25 (about 70%). Above N/P 15, the modified bPEI-25 polymers declined in efficiency relative to non-modified bPEI-25. Non-modified bPEI-25 had a maximum efficiency of about 80% at N/P 20. The cholesteryl modified bPEI-25 polymer P46 was the least efficient at N/P 10 to 20 (about 5% to 20%), and had a maximum efficiency of about 25% at N/P 20 to 30.

Luciferase Expression in HepG2 Cells.

Figure 36:
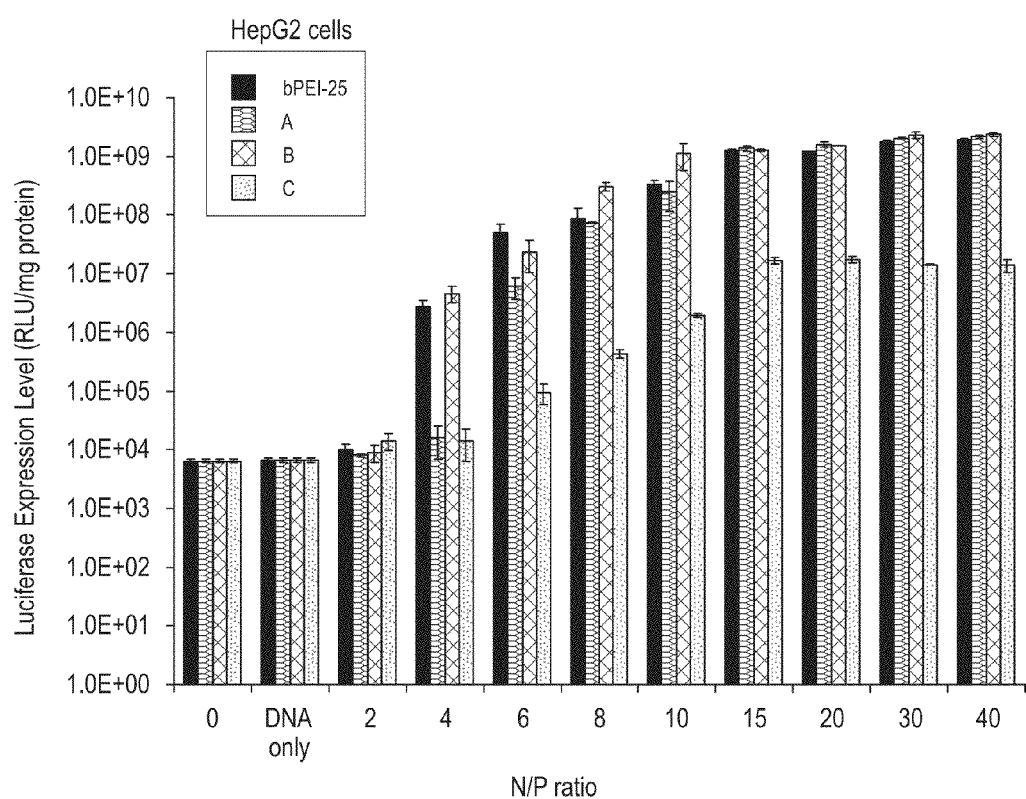
FIG. 36 is a bar graph showing the in vitro luciferase expression levels in HepG2 cells at different N/P ratios mediated by luciferase reporter gene complexes prepared with carbamate functionalized bPEI-25 polymers A, B, and C. Controls included a luciferase gene complex of bPEI-25, luciferase gene alone (labeled DNA only), and polymer alone (labeled "0"). Results represent mean 35 standard deviation of triplicates.

While GFP transfection efficiency reflects the percentage of cells successfully transfected with the GFP plasmid for GFP expression, luciferase assay detects the mean protein expression level in the transfected cells. As can be seen in FIG. 36, the luciferase expression profiles of polymers A, B and non-modified bPEI-25 were similar, with luciferase expression level increasing with N/P ratio up to about N/P 15, and leveling off at about 1×10$^9$ RLU/mg protein for N/P ratios 15 to 40. The luciferase expression level induced by C was two orders of magnitude lower than that mediated by non-modified bPEI-25. The low gene transfection mediated by C/DNA correlated with the size and zeta potential data for C (FIGS. 1 and 5). Polymer concentrations in the order of N/P ratios specified in FIG. 36 are as follows: non-modified PEI-25—0, 1.1, 2.3, 3.4, 4.6, 5.7, 8.6, 11.5, 17.2 and 22.9 mg/L; A—0, 2.3, 4.7, 7.0, 9.4, 11.7, 17.6, 23.4, 35.1 and 46.8 mg/L; B—0, 1.6, 3.1, 4.7, 6.3, 7.8, 11.7, 15.6 23.5 and 31.3 mg/L; C—0, 4.7, 9.4, 14.1, 18.8, 23.5, 35.2, 46.9, 70.4 and 93.8 mg/L.

Cytotoxicity Test Procedure.

The cytotoxicity of the modified bPEI-25/gene complexes and modified bPEI-25/siRNA complexes was studied using the standard MTT assay protocol on HepG2, HeLa and SK-OV-3 cells. The GFP plasmid was used for complex formation and treatment of HepG2 and HeLa cells, while the luciferase plasmid was used for complex formation and treatment of SK-OV-3 cells.

HepG2, HeLa and SK-OV-3 cells were seeded onto 96-well plates at densities of 10000 cells, 5000 and 16000 cells per well, respectively, and allowed to grow to 60% to 70% confluency before treatment. Polymer/gene or polymer/siRNA complexes at various N/P ratios were prepared in water as described above. The cells in each well were then incubated with growth medium comprising 10 microliters of polymer/nucleic acid complexes and 100 microliters of fresh medium for 4 hours at 37° C. Following incubation, the medium was replaced with fresh growth medium and incubated further for 68 hours. Subsequently, 100 microliters of growth medium and 20 microliters of MTT solution (5 mg/mL in PBS) were then added to each well and the cells were incubated for 4 hours at 37° C. Formazan crystals formed in each well were solubilized using 150 microliters of DMSO upon removal of growth media. A 100 microliter aliquot from each well was then transferred to a new 96-well plate for determination of absorbance using a microplate spectrophotometer at wavelengths of 550 nm and 690 nm. Relative cell viability was expressed as [($A_{550}$–$A_{690}$)sample/($A_{550}$–$A_{690}$)control]×100%. Data were expressed as mean±standard deviations of at least eight replicates per N/P ratio.

Cytotoxicity in HepG2 and Hela Cell Lines.

Figure 37:
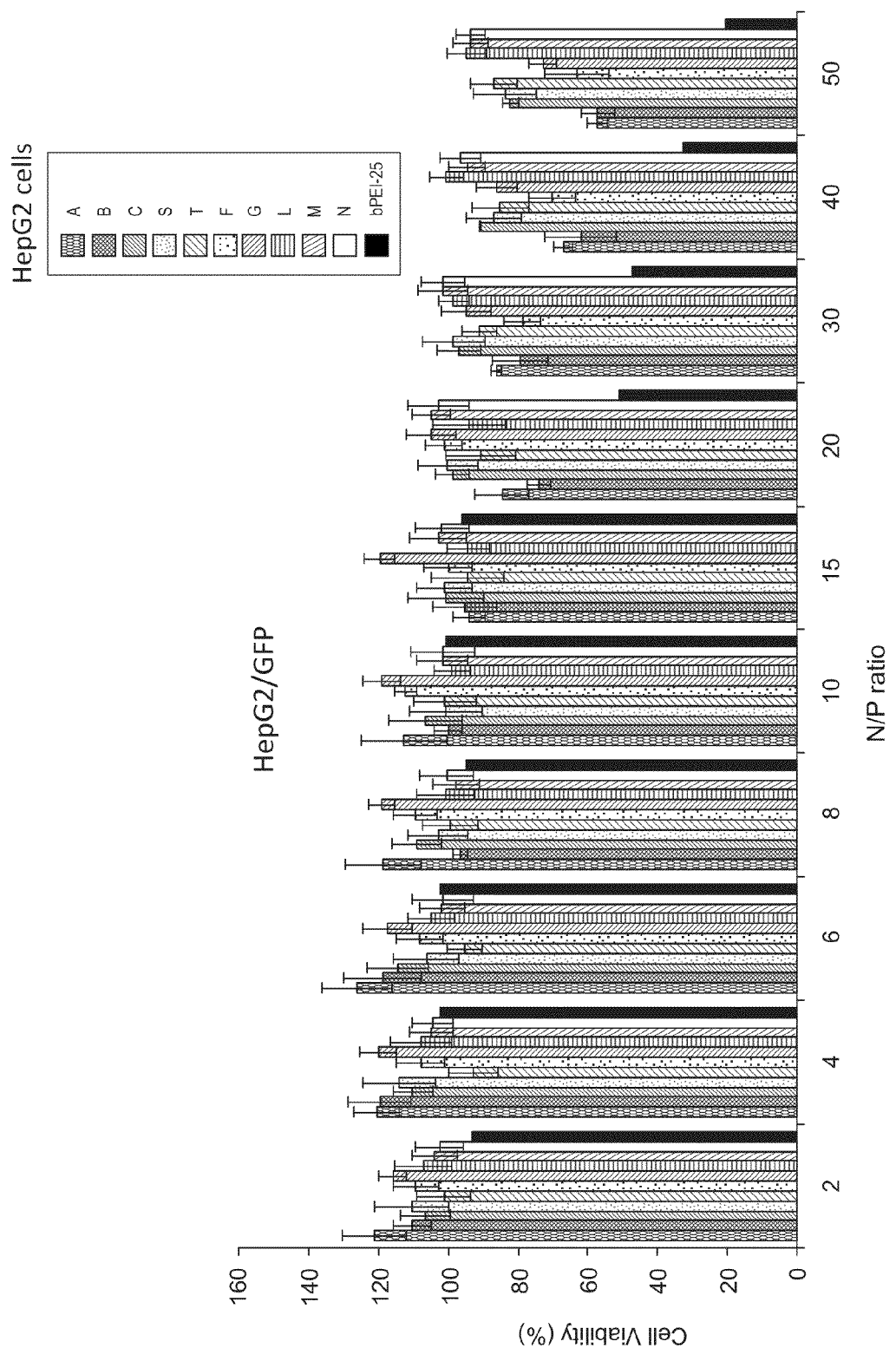
FIGS. 37-39 are bar graphs showing the cell viability of HepG2 cells after incubation with the GFP reporter gene complexes of various carbamate functionalized bPEI-25 polymers at N/P ratios 2 to 50. A control gene complex of bPEI-25 is also shown.
Figure 38:
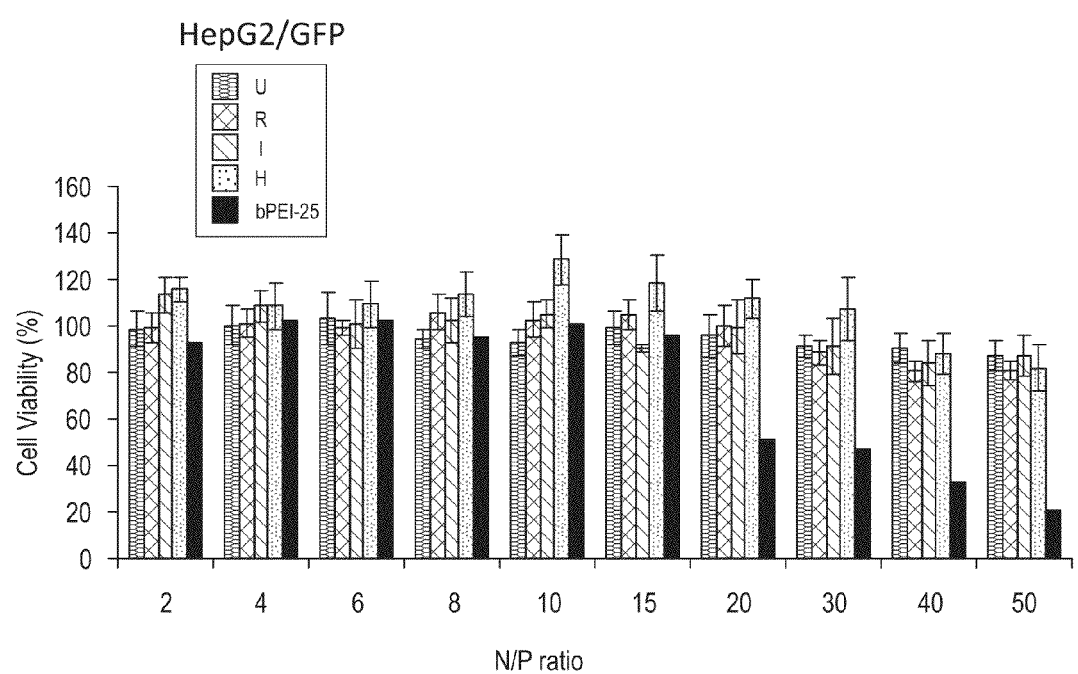
Figure 39:
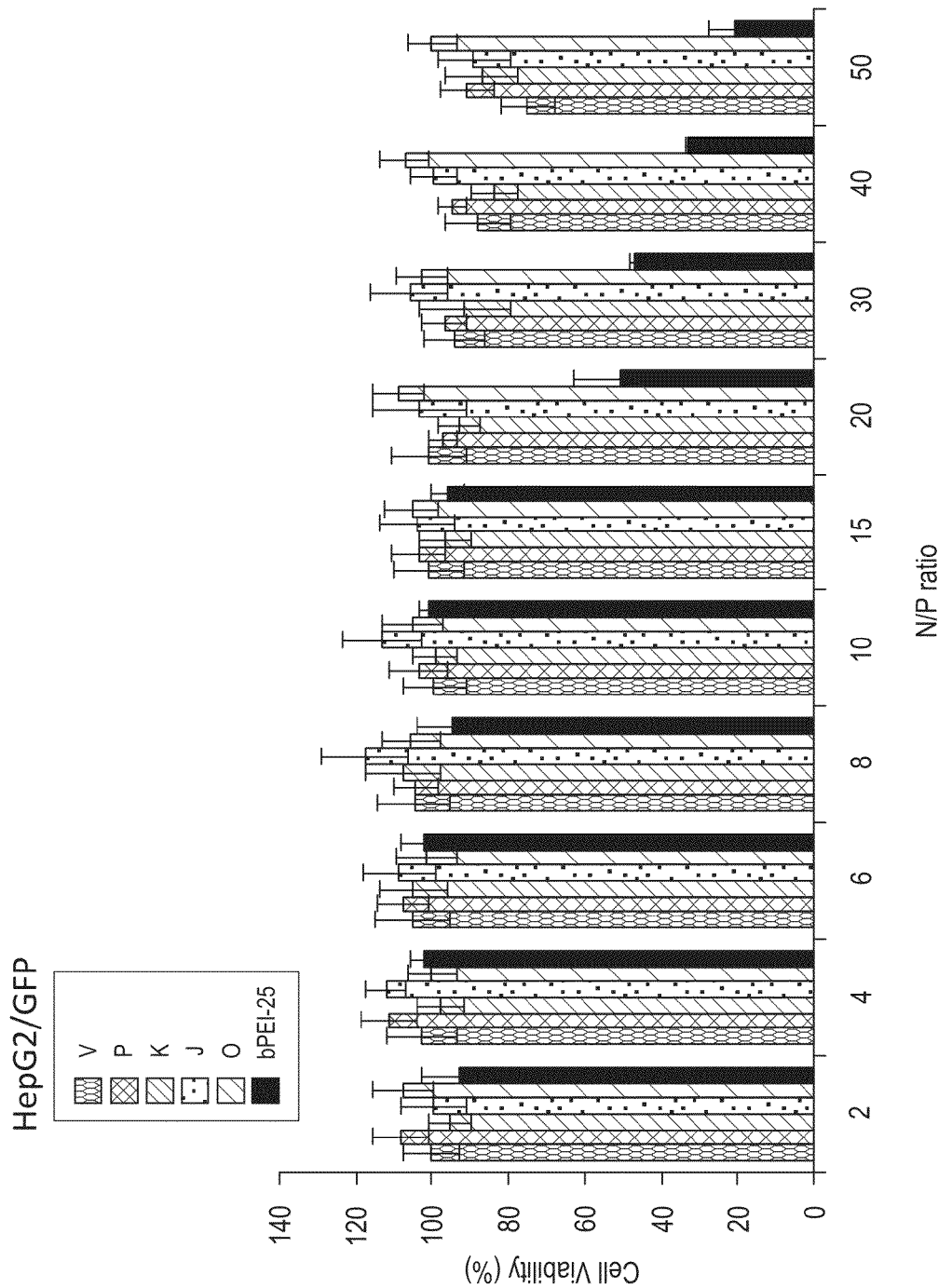
Figure 40:
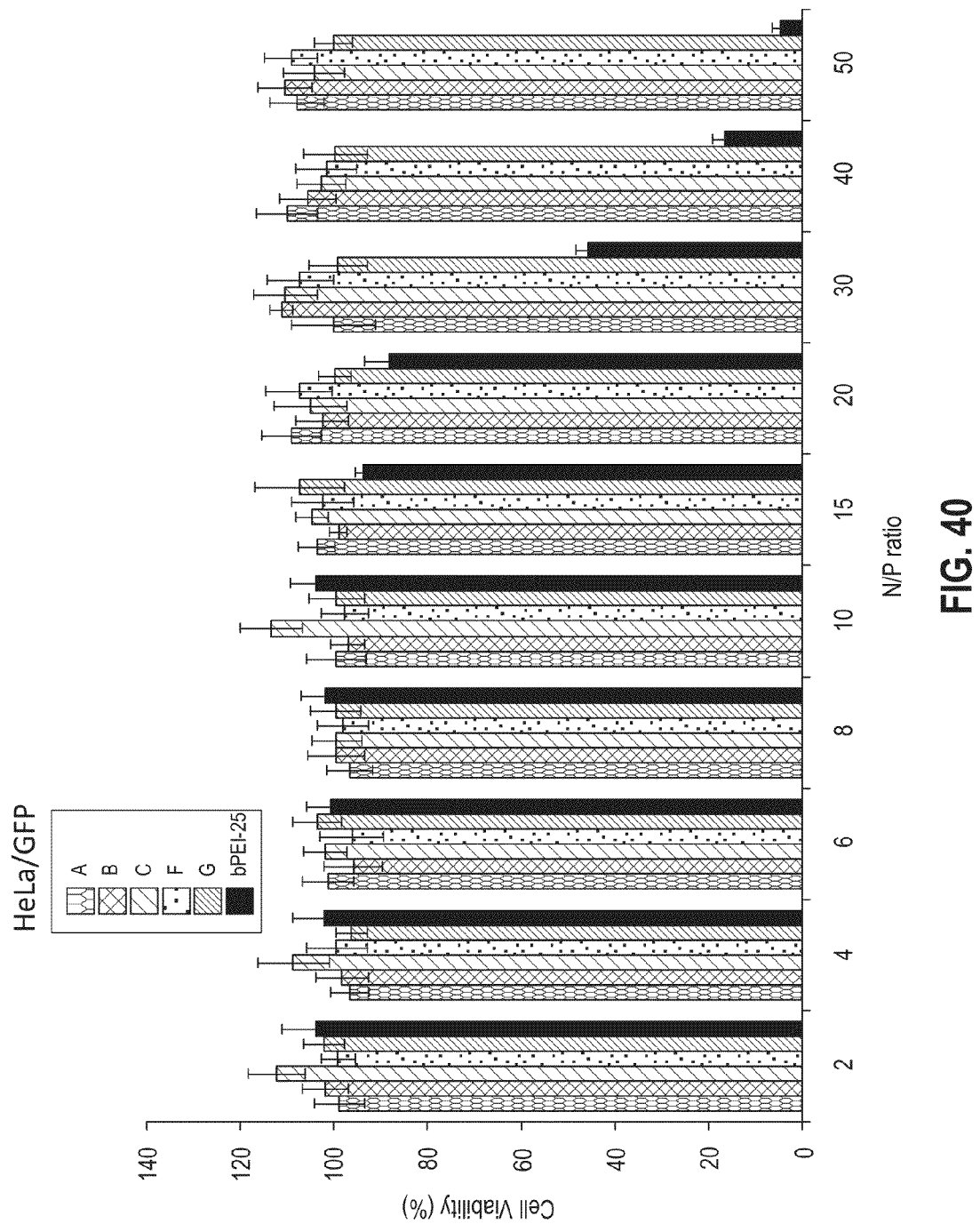
FIG. 40 is a bar graph showing the viability of HeLa cells after incubation with GFP reporter gene complexes of various carbamate functionalized bPEI-25 polymers at N/P ratios 2 to 50. A control gene complex formed with bPEI-25 is also shown.

FIGS. 37 to 39 are bar graphs showing the viability of HepG2 cells after incubation with GFP reporter gene complexes of modified bPEI-25 polymers A, B, C, S, T, F, G, L, M, N, U, R, I, H, V, P, K, J, O and non-modified bPEI-25 at various N/P ratios. FIG. 40 is a bar graph showing the viability of HeLa cells after incubation with GFP reporter gene complexes of modified bPEI-25 polymers A, B, C, F, and G and non-modified bPEI-25 at various N/P ratios. All gene complexes of the modified bPEI-25 polymers were much less cytotoxic than the gene complex of non-modified bPEI-25 at N/P 20 to 50 in both cell lines. Results represent mean±standard deviation of at least 8 replicates. Polymer concentrations in the order of N/P ratios specified: non-modified bPEI-25—0, 0.8, 1.6, 2.4, 3.2, 4.0, 6.0, 8.0, 12.0, 16.0 and 20.0 mg/L; A, F, G, H, I, J—0, 1.6, 3.3, 4.9, 6.6, 8.2, 12.3, 16.4, 24.6, 32.8 and 41.0 mg/L; B—0, 1.1, 2.2, 3.3, 4.4, 5.5, 8.2, 11.0, 16.4, 21.9 and 27.4 mg/L; C—0, 3.3, 6.6, 9.9, 13.1, 16.4, 24.6, 32.8, 49.3, 65.7 and 82.1 mg/L; K—0, 1.0, 2.1, 3.1, 4.1, 5.2, 7.7, 10.3, 15.5, 20.6 and 25.8 mg/L; L—0, 2.2, 4.4, 6.7, 8.9, 11.1, 16.7, 22.2, 33.3, 44.4, and 55.5 mg/L; M—0, 4.8, 9.5, 14.3, 19.1, 23.9, 35.8, 47.7, 71.6, 95.5, and 119.3 mg/L; N—0, 14.1, 28.1, 42.2, 56.3, 70.3, 105.5, 140.7, 211.0, 281.3, and 351.7 mg/L; T, U—0, 1.0, 2.0, 3.1, 4.1, 5.1, 7.7, 10.2, 15.3, 20.4, 25.5 mg/L; R, S—0, 1.2, 2.5, 3.7, 4.9, 6.2, 9.2, 12.3, 18.5, 24.6, and 30.8 mg/L; V—0, 0.8, 1.7, 2.5, 3.3, 4.2, 6.2, 8.3, 12.5, 16.6, and 20.8 mg/L; P—0, 0.9, 1.8, 2.7, 3.6, 4.5, 6.7, 8.9, 13.4, 17.8, and 22.3 mg/L; O—0, 1.2, 2.4, 3.6, 4.8, 6.0, 9.1, 12.1, 18.1, 24.2, and 30.2 mg/L.

As seen in FIGS. 37 to 40, the viability of HepG2 and HeLa cells treated with non-modified bPEI-25/gene complex steeply declines at N/P ratios greater than 15 (increasing non-modified bPEI-25 concentration). The HepG2 cell viability was less than 60% at N/P 20 and higher. The HeLa cell viability was less than 46% at N/P 30 and higher (FIG. 40). In particular, at N/P 50, the cell viability was only about 20% for HepG2 and only 4.6% for HeLa when treated with non-modified bPEI-25/DNA complexes. However, the viability of HepG2 cells treated with DNA complexes of A, B, C, S, T, F, G, L, M, N, U, R, I, H, V, P, K, J, and O at N/P 50 was 57%, 57%, 82%, 84%, 87%, 63%, 73%, 95%, 94%, 94%, 87%, 81%, 87%, 82%, 75%, 91%, 87%, 89%, 99%, respectively, (FIGS. 37 to 39). The viability of HeLa cells treated with DNA complexes of A, B, C, F, G at N/P 50 was 100% in each case (FIG. 40).

Although non-modified bPEI-25 exhibits peak transfection efficiencies of about 25% in the HepG2 cell line (N/P 40) and about 9% in the Hela cell line at N/P 50, its high toxicity above N/P 15 impedes its potential in vivo application, which usually requires a high polymer concentration to achieve distinctive therapeutic effects. In the present study, cell viability was significantly enhanced by modification with mannose functionalized cyclic carbonates and other functionalized cyclic carbonates. Mannose is a common metabolite and research has shown direct utilization of mannose for mammalian glycoprotein biosynthesis. Therefore it should not impose any toxic effects on the cells. Compared to non-modified bPEI-25 (cell viability<60% above N/P 15 in HepG2 cells and above N/P 20 in Hela cells), a much higher percentage of HepG2 cells remained viable using mannose modified bPEI-25 at N/P 30 to 50, and nearly all HeLa cells were viable even at N/P 50. Importantly, at N/P 30 to 50, gene transfection efficiency provided by the modified bPEI-25 polymers was significantly higher than that given by non-modified bPEI-25 at N/P 15 (FIGS. 30 to 34). bPEI-25 modified with galactose, glucose, and hydrophobic groups also showed reduced cytotoxicity compared to non-modified bPEI-25.

Cytotoxicity in SK-OV-3 Cell Line

Figure 47:
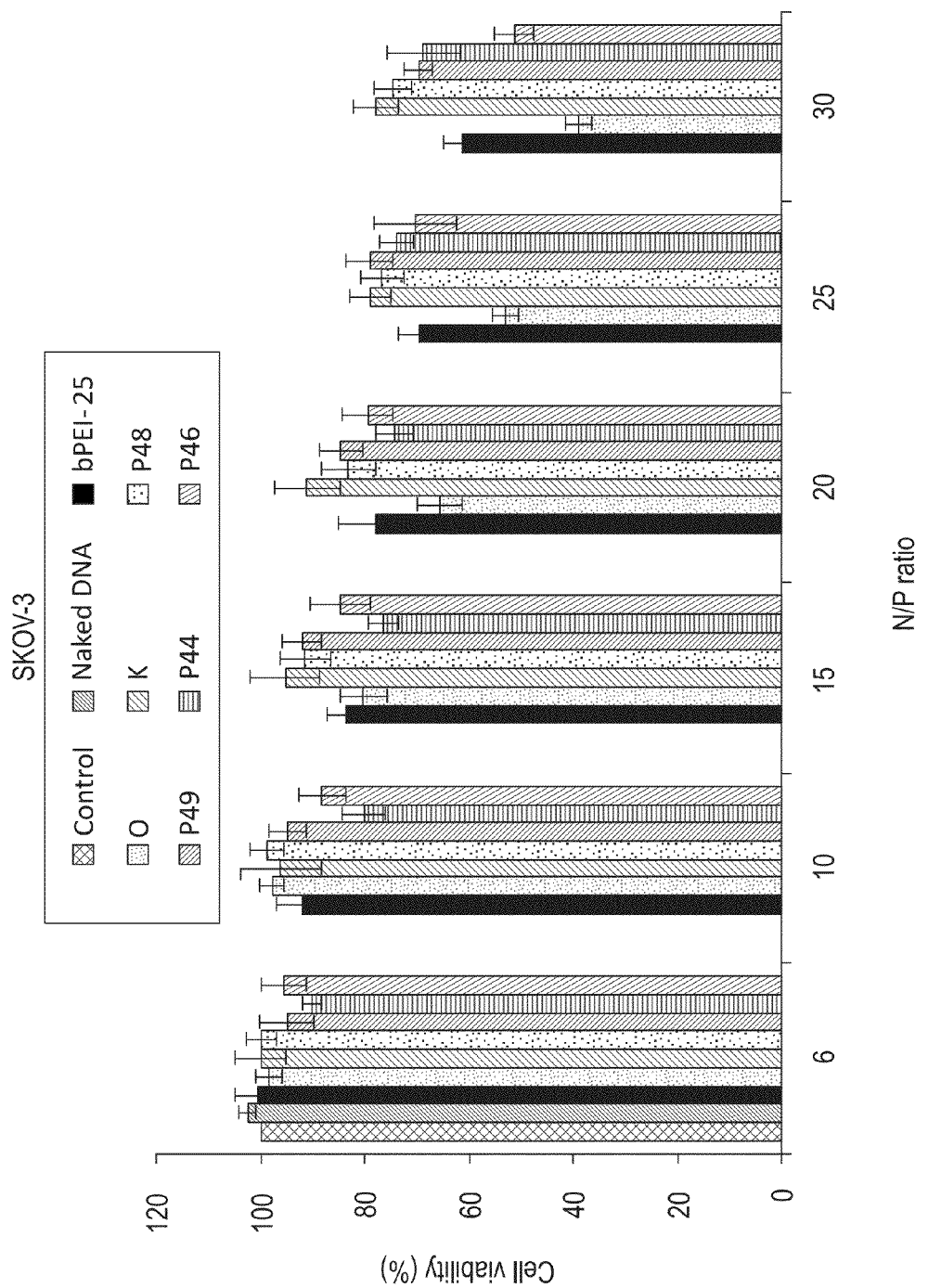
FIG. 47 is a bar graph comparing the SK-OV-3 cell viability in the presence of the GFP reporter gene complexes of carbamate functionalized bPEI-25 polymers 0, K, P44, P46, P48 to P49 at different N/P ratios.

The SK-OV-3 cell viability in the presence of the O/GFP gene complex was less than the cell viability for the control complex with non-modified bPEI-25 at N/P 15 to 40 (FIG. 47). However, polymer K (prepared with TMC at 46% amine modification) was favored over non-modified bPEI-25 in both efficiency (about 75%) and cell viability (90% or more) at N/P 10 and 15.

siRNA Mediated Bcl-2 Knockdown in HeLa Cells

Figure 41:
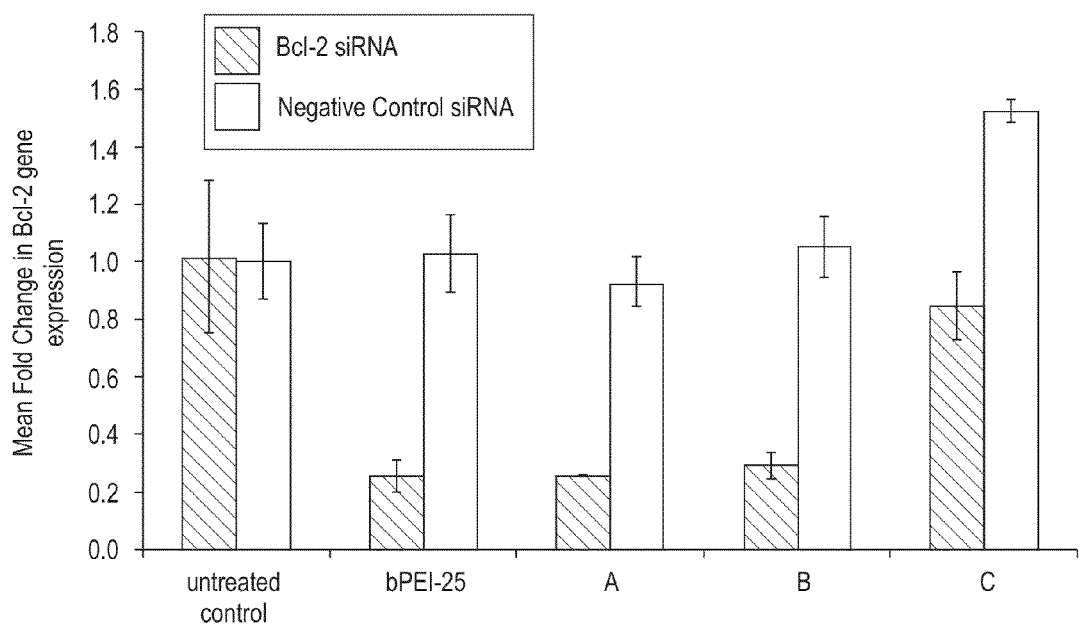
FIG. 41 is a graph showing downregulation of Bcl-2 mRNA in HeLa cells by siRNA complexes of carbamate functionalized bPEI-25 polymers A, B, and C at N/P 50. The siRNA concentration was 100 nM.

As shown in the bar chart of FIG. 41, siRNA was successfully delivered inside HeLa cells using Polymer A and Polymer B, and Bcl-2 downregulation at the mRNA level was manifest. In FIG. 41, the corresponding polymer concentrations used were: non-modified bPEI-25—8.4 mg/L; A—17.1 mg/L; B—11.4 mg/L; C—34.3 mg/L. For Bcl-2 knockdown mediated by polymer A/siRNA and polymer B/siRNA complexes, mRNA expression levels were reduced to 25% and 29% of that in the untreated HeLa cells, respectively, which was comparable to the knockdown level induced by non-modified bPEI-25/siRNA complexes (26%). In a control experiment where negative control siRNA (i.e., scrambled siRNA) was used, no mRNA downregulation was observed.

However, siRNA delivery by polymer C was not successful as the amount of Bcl-2 mRNA was still 85% of that in the untreated cells.

Viability of HeLa Cells after being Treated with Polymer/siRNA Complexes.

Figure 42:
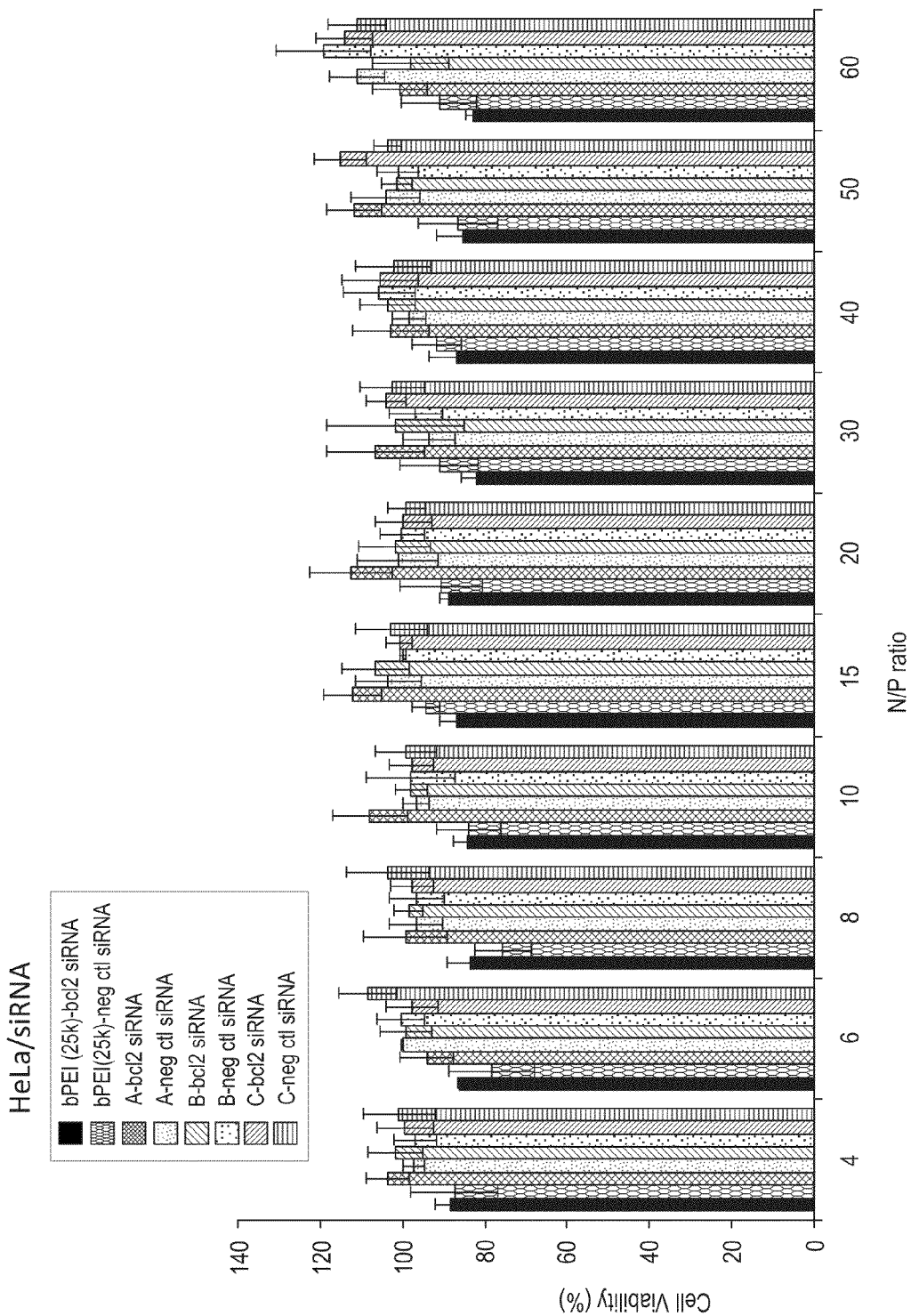
FIG. 42 is a bar graph showing the viability of HeLa cells after treatment with carbamate functionalized bPEI-25 polymer/siRNA complexes at various N/P ratios.

FIG. 42 is a bar graph showing the viability of HeLa cells after being treated with modified bPEI-25/siRNA complexes at various N/P ratios. The siRNA concentration was fixed at 100 nM. The polymer concentrations corresponding to different N/P ratios used: non-modified bPEI-25—0.7, 1.0, 1.3, 1.7, 2.5, 3.4, 5.0, 6.7, 8.4 and 10.1 mg/L; A—1.4, 2.1, 2.7, 3.4, 5.1, 6.9, 10.3, 13.7, 17.1 and 20.6 mg/L; B—0.9, 1.4, 1.8, 2.3, 3.4, 4.6, 6.9, 9.2, 11.4 and 13.7 mg/L; and C—2.7, 4.1, 5.5, 6.9, 10.3, 13.7, 20.6, 27.4, 34.3 and 41.2 mg/L.

The HeLa cells appeared to be resistant to Bcl-2 siRNA-induced cell death at the siRNA and polymer concentration tested in this study. As can be seen in FIG. 42, there was no difference between the cytotoxicity when Bcl-2 siRNA or scrambled siRNA (the negative control) was delivered into HeLa cells at various N/P ratios. Therefore any difference in cell viability was due to the nature of the polymers used. For the non-modified bPEI-25/Bcl-2 siRNA complexes, 82% of the cells were alive after treatment using N/P ratio 60. With A, B and C/Bcl-2 siRNA complexes, nearly 100% of the HeLa cells were viable at N/P 60. Together with the mRNA knockdown data, polymers A and B were effective in complexing with negatively charged siRNA and mediating siRNA uptake into HeLa cells, leading to successful Bcl-2 mRNA down-regulation at a level comparable to non-modified bPEI-25, while maintaining excellent cell viability. Although HeLa cells were resistant to death after Bcl-2 mRNA knockdown, this mRNA knockdown is reported to sensitize cancer cells to an anticancer drug.

Table 7 compares the maximum GFP transfection efficiencies obtained for selected modified bPEI-25 polymers and non-modified bPEI-25 in the HepG2, Hela and SK-OV-3 cell lines when the cell viability was 80% or more. Also listed in Table 7 is the maximum N/P ratio at which the cell viability was 80% or more.

TABLE 7

| Ex. | Polymer Name | Cyclic Monomer | Mass Feed Ratio (bPEI-2: Cyclic Monomer) | Molar Feed Ratio (bPEI: Cyclic Monomer) | Maximum N/P ratio and Maximum GFP Transfection Efficiency (%) for Cell Viability ≥80% | | | | | |
|---|---|---|---|---|---|---|---|---|---|---|
| | | | | | HepG2 | | HeLa | | SK-OV-3 | |
| | | | | | Max N/P | Max. Eff, (%) | Max N/P | Max. Eff (%) | Max N/P | Max. Eff (%) |
| (comp) | bPEI-25 | | | | 15 | 5 | 20 | 1.7 | 15 | 70 |
| 12 | A | MTC-IPMAN | 1:1 | 1:25 | 30 | 16 | 50 | 4.4 | | |
| 13 | B | MTC-IPMAN | 3:1 | 1:8 | 30 | 22 | 50 | 5.3 | | |
| 14 | C | MTC-IPMAN | 1:3 | 1:75 | 50 | 1 | 50 | 0.7 | | |
| 15 | F | MTC-IPMAN | 1:1 | 1:25 | 20 | 12 | 50 | 6.9 | | |
| 16 | G | MTC-IPMAN | 1:1 | 1:25 | 40 | 49 | 50 | 2.8 | | |
| 17 | L | MTC-IPMAN | 1:2.3 | 1:58 | 50 | 8 | | | | |
| 18 | M | MTC-IPMAN | 1:5 | 1:120 | 50 | 4 | | | | |
| 19 | N | MTC-IPMAN | 1:16 | 1:400 | 50 | 4 | | | | |
| 20 | S | MTC-IPMAN | 2:1 | 1:12.5 | 50 | 37 | | | | |
| 21 | T | MTC-IPMAN | 4:1 | 1:6 | 50 | 36 | | | | |
| 22 | H | MTC-IPGLU | 1:1 | 1:25 | 50 | 22 | | | | |
| 23 | I | MTC-IPGAL | 1:1 | 1:25 | 50 | 27 | | | | |
| 24 | R | MTC-IPGAL | 2:1 | 1:12.5 | 50 | 36 | | | | |
| 25 | U | MTC-IPGAL | 4:1 | 1:6 | 50 | 29 | | | | |
| 26 | J | TMC | 1:1 | 1:100 | 50 | 26 | | | | |
| 27 | K | TMC | 4:1 | 1:25 | 50 | 64 | | | 20 | 75 |
| 28 | P | TMC | 12:1 | 1:8 | 50 | 35 | | | | |
| 29 | V | TMC | 100:1 | 1:1 | 40 | 15 | | | | |
| 30 | O | MTC-C2 | 2:1 | 1:25 | 50 | 48 | | | 15 | 78 |
| 31 | P43 | MTC-Bn | 1.6:1 | 1:25 | | | | | | |
| 32 | P48 | MTC-Bn | 13.3:1 | 1:3 | | | | | 20 | 65 |
| 33 | P44 | MTC-PUC2 | 1.2:1 | 1:25 | | | | | 6 | 5 |
| 34 | P49 | MTC-PUC2 | 10.4:1 | 1:3 | | | | | 20 | 66 |
| 35 | P45 | Chol-MTC | 5.4:1 | 1:3 | 20 | 7 | | | | |
| 36 (comp) | P46 | Chol-Cl | 7:1 | 1:3.2 | 10 | 2 | | | 15 | 10 |
| 37 (comp) | P47 | BuOCOCl | 2.9:1 | 1:25.2 | 20 | 3 | | | | |

In the HepG2 cell line (Table 7), non-modified bPEI-25 has a maximum N/P ratio of 15 and a maximum GFP transfection efficiency of 5% for a cell viability of 80% or more. In general, the cyclic carbonate modified bPEI-25 polymers have higher maximum N/P ratios (N/P 20 to 50) and higher maximum GFP transfection efficiencies (8% to 64%) for a cell viability of 80% or more. With the exceptions of polymers J and V, GFP transfection efficiencies exceeded 10% using a bPEI-25:cyclic carbonate molar feed ratio of about 1:6 to about 1:25 (about 10% to about 45% of primary amine groups modified). Insolubility limited the cholesteryl modified BPEI-25 polymers P45 and P46 (comparative) to about 5% modification of the primary the amine groups. For this modification level, P45 and P46 had maximum N/P ratios and maximum GFP transfection efficiencies similar to non-modified bPEI-25. BuOCOCl modified bPEI-25 (P47, 43% of primary amine groups modified) also had a maximum N/P ratio and maximum GFP transfection efficiency comparable to non-modified bPEI-25. The results indicate that maximum N/P ratio and maximum GFP transfection efficiency were favored by modifying the primary amine groups with a cyclic carbonate, TMC being especially favored (polymer K) at about a 45% modification level (1:25 molar feed ratio).

The same trend was observed in the HeLa cell line at lower overall GFP transfection efficiencies for the selected polymers (Table 7).

Less differentiation between the modified bPEI-25 polymers and non-modified bPEI-25 (Table 7) was seen in the SK-OV-3 line. In this instance, the non-modified bPEI-25 had a maximum N/P ratio of 15 and a maximum efficiency of 70%. Polymer K had maximum N/P ratio of 20 and a maximum efficiency of 75%. Polymer O had maximum N/P ratio of 15 and a maximum efficiency of about 78%.

The results show that polymer K is a more efficient and less toxic transfection agent for multiple cancer cell lines compared non-modified bPEI-25.

In Vitro Luciferase Expression in Human Mesenchymal Stem Cells (hMSC)

Poietics™ human mesenchymal stem cells (mHSC) were purchased from Lonza, Singapore, and cultured in the mesenchymal stem cell basal medium (MSCBM) (Lonza, Singapore), which was supplemented with mesenchymal cell growth supplement (MCGS), L-glutamine and GA-1000 (MSCGM™ SingleQuots™, Lonza, Singapore). Cells were cultured at 37° C., under an atmosphere of 5% $CO_2$ and 95% humidified air. It was split using Trypsin/EDTA medium when reached 90% confluence.

To evaluate the in vitro gene transfection efficiency of the modified bPEI-25 polymer/DNA complexes in mHSC, cells were seeded onto 24-well plates at a density of $1 \times 10^5$ cells per 500 microliters per well. After 24 hours, the plating media were replaced with fresh growth media, followed by the dropwise addition of 50 microliters of complex solution (containing 1.75 micrograms of GFP plasmid DNA or 2.5 micrograms of luciferase plasmid DNA) at various N/P ratios. Following 4 hours of incubation, free complexes were removed by replacing the medium in each well. After a further 68 hours of incubation, the cell culture medium in each well was removed and the cells were rinsed once with 0.5 mL of phosphate-buffered saline (PBS, pH 7.4). 0.2 mL of reporter lysis buffer was added to each well. The cell lysate collected after two cycles of freezing (−80° C., 30 min) and thawing was cleared by centrifugation at 14,000 rpm for 5 min, after which 20 microliters of supernatant was mixed with 100 microliters of luciferase substrate for the determination of relative light units (RLU) using a luminometer (Lumat LB9507, Berthold, Germany). The RLU readings were normalized against the protein concentration of the supernatant determined using the BCA protein assay to give the overall luciferase expression efficiency. In all in vitro gene expression experiments, untreated cells were used as the negative control, and cells treated with non-modified bPEI-25/DNA complexes were used as the positive control. Data were expressed as mean±standard deviations of three replicates.

Figure 43:
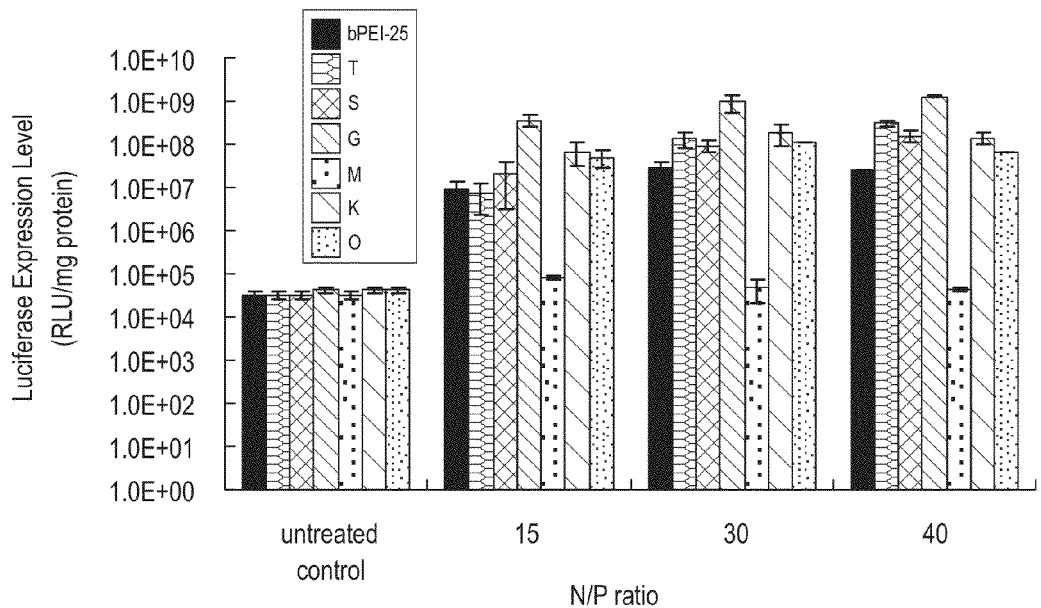
FIG. 43 is a graph of the luciferase expression level as a function of N/P ratio for luciferase reporter gene complexes of carbamate functionalized bPEI-25 polymers T, S, G, M, K, and O in human mesenchymal stem cells.

FIG. 43 is a graph showing the luciferase expression level as a function of N/P ratio for luciferase reporter gene complexes of modified bPEI-25 polymers T, S, G, M, K, and O in human mesenchymal stem cells (hMSC). Polymer G (mannose modified bPEI-25) had greater luciferase expression level in human mesenchymal stem cells compared to polymers K (TMC modified bPEI-25) and O (MTC-C2 modified bPEI-25) because the cells over express mannose receptors. Compared to other compositions, G was the best in mediating gene transfection.

The cytotoxicity of the polymer/DNA complexes was studied using the standard MTT assay protocol. The hMSC were seeded onto 96-well plates at densities of 10000 cells per well, one day before transfection. Polymer/DNA at various N/P ratios were prepared in water. The cells in each well were then incubated with growth medium comprising of 10 microliters of polymer/DNA complexes and 100 microliters of fresh medium for 4 hours at 37° C. Following incubation, the medium was replaced with fresh growth medium and incubated further for 68 hours. Subsequently, 100 microliters of growth medium and 20 microliters of MTT solution (5 mg/mL in PBS) were added to each well and the cells were incubated for 4 hours at 37° C. Formazan crystals formed in each well were solubilized using 150 microliters of DMSO upon removal of growth media. The absorbance was measured using a microplate spectrophotometer at wavelengths of 550 nm and 690 nm. Relative cell viability was expressed as [(A550−A690)sample/(A550−A690)control]×100%. Data were expressed as mean±standard deviations of at least eight replicates per N/P ratio.

Figure 44:
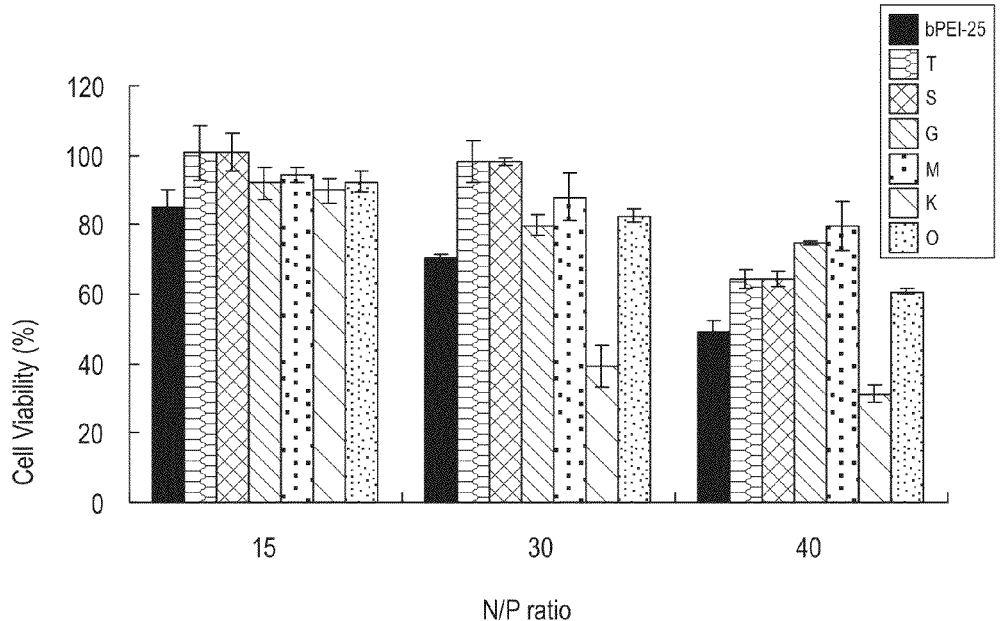
FIG. 44 is a graph showing the cytotoxicity of the luciferase complexes of T, S, G, M, K, and O toward human mesenchymal stem cells (hMSC).

FIG. 44 is a graph showing the cytotoxicity of the luciferase complexes of T, S, G, M, K, and O toward human mesenchymal stem cells. The G/DNA complexes were not significantly toxic to the cells. Cell viability was higher than 75% at N/P 40.

GFP Transfection Efficiency and HepG2 Cell Viability with P45 to P47

Figure 45:
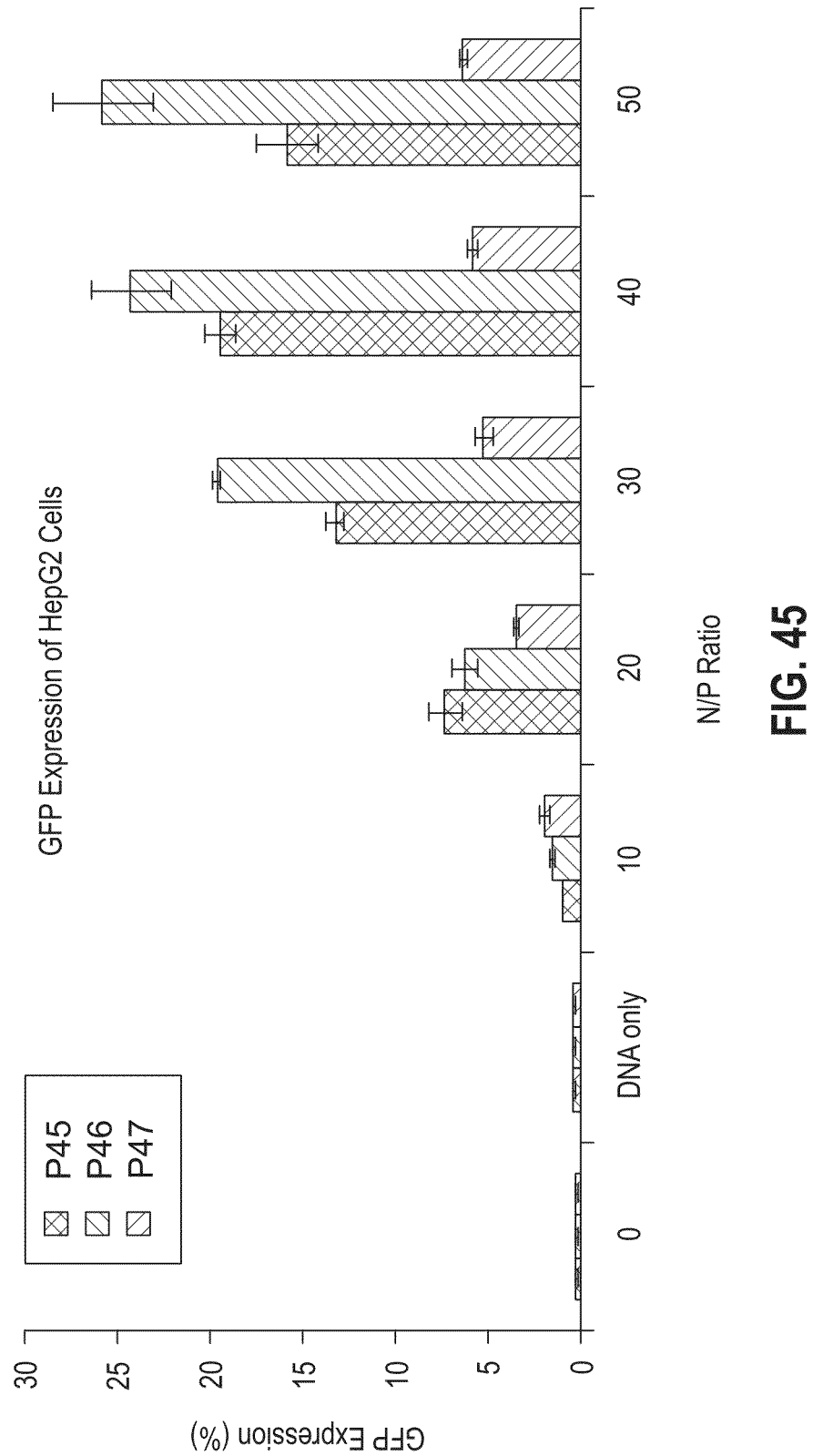
FIG. 45 is a bar graph comparing the transfection efficiency in HepG2 cells of GFP reporter gene complexes of carbamate functionalized bPEI-25 polymer P45, P46 (comparative), and P47 (comparative) at different N/P ratios. P45 was prepared from a cholesteryl substituted cyclic carbonate (Chol-MTC), P46 was prepared from cholesteryl chloroformate, and P47 was prepared from butyl chloroformate.

GFP reporter gene complexes of P45 to P47 were prepared at different N/P ratios according the general procedure described above. FIG. 45 is a bar graph comparing the GFP transfection efficiency of these complexes in HepG2 cells at the different N/P ratios. The butyl chloroformate modified bPEI-25 had the lowest efficiency, about 5%. Cholesteryl chloroformate modified bPEI-25 had the highest efficiency of the three modified bPEI-25 polymers, about 25%. The Chol-MTC modified bPEI-25 had a transfection efficiency of about 15%. The above results show that P45 to P47 have much lower GFP transfection efficiency in HepG2 cells compared to G (FIG. 30, about 50% efficiency) and K (FIG. 32, about 65% efficiency).

Figure 46:
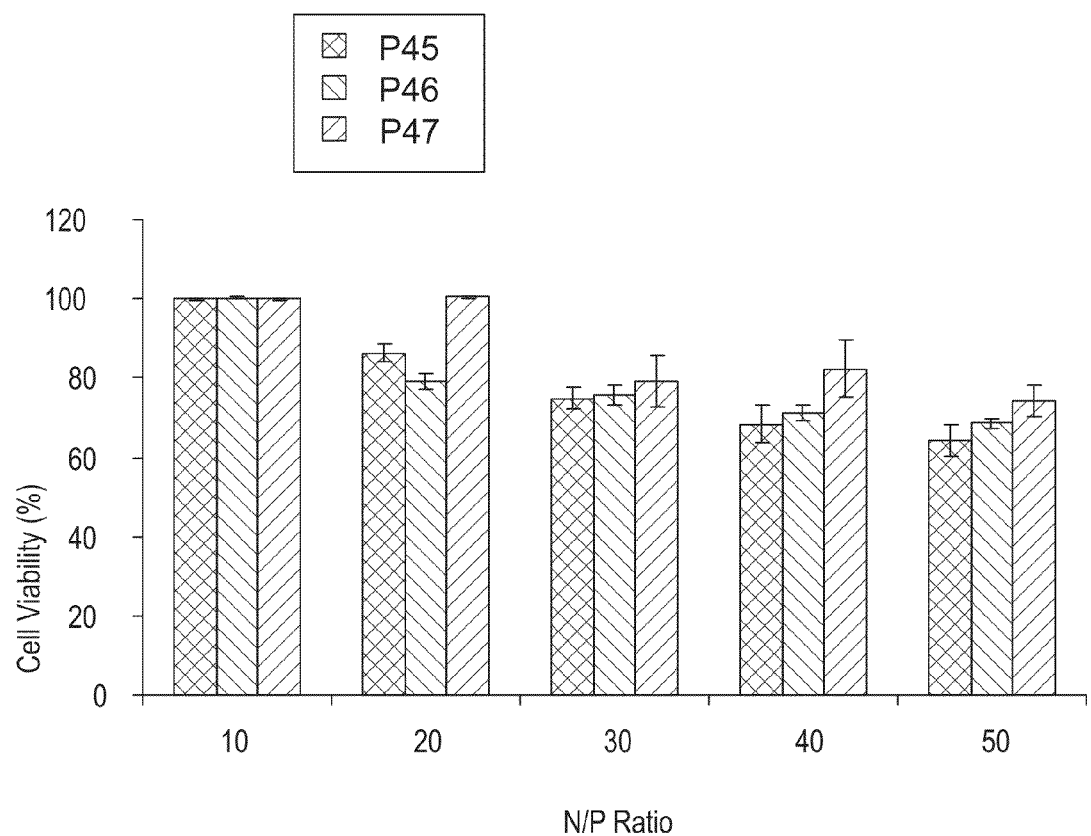
FIG. 46 is a bar graph comparing the HepG2 cell viability in the presence of the GFP reporter gene complexes of P45 to P47 at different N/P ratios.

FIG. 46 is a bar graph comparing the HepG2 cell viability with the GFP complexes of P45 to P47. About 70% of the transfected HepG2 cells were viable at N/P 30 to N/P 50 for P45 to P47.

Antimicrobial Activity of Modified bPEI-25 Polymers.

Mueller hinton broth II (MHB) powder and yeast mould broth (YMB) powder were used to prepare the broths according to the manufacture's instruction. *Staphylococcus aureus* (*S. aureus*) (ATCC No. 6538), and *Escherichia coli* (*E. coli*) (ATCC No. 25922) were obtained from ATCC (U.S.A) and re-cultured according to the suggested protocols. 3-[4,5-Dimethylthiazolyl-2]-2,5-diphenyl tetrazolium bromide (MTT) was used as received. All other chemicals were of analytical grade, and used as received.

The minimum inhibitory concentration (MIC) of the modified bPEI-25 polymers was measured using a broth microdilution method. The modified bPEI-25 polymers were dissolved in DI water at a concentration of 5000 mg/L. The samples were further diluted to 7.8125, 15.625, 31.25, 62.5, 125, 250.0, 500.0 and 1000.0 mg/L using MHB or YMB. The optical density of the bacterial solution was adjusted to $OD_{600}$ nm=0.07 to 0.08 by the addition of MHB or YMB. This bacterial solution was further diluted 1000 times. Cationic compound solution (100 microliters) was transferred to each well of 96 well plates (NUNC), followed by the addition of 100 microliters of the bacterial solution. MHB or YMB was used as control. The optical density readings of bacterial solutions were monitored by measuring $OD_{600nm}$ in predetermined times. The assay was performed in six replicates for each sample and the experiments were repeated at least three times. Table 8 lists the MICs against *E. coli* and *S. aureus* for selected modified bPEI-25 polymers.

TABLE 8

| Ex. | Polymer Name | Cyclic Carbonate Monomer | % Primary Amine Groups Modified (NMR)[a] | MIC (mg/L) E. coli | MIC (mg/L) S. Aureus |
|---|---|---|---|---|---|
| (comp) | BPEI-25 | | 0 | >500 | 62.5 |
| 16 | G | MTC-IPMAN | 39.7 | >500 | >500 |
| 20 | S | MTC-IPMAN | 21.0 | >500 | 62.5 |
| 21 | T | MTC-IPMAN | 9.5 | >500 | 62.5 |
| 27 | K | TMC | 46.6 | >125 | 62.5 |

The results indicate that the antimicrobial activity of modified bPEI-25 polymers G, S, T, and K against Gram negative *E. coli* and Gram positive *S. aureus* is comparable to non-modified bPEI-25.

SUMMARY

Non-modified bPEI-25 was successfully modified with carbonate-mannose/galactose/glucose/hydrophobic groups at various feed molar ratios. Transfection efficiency of gene complexes of the modified bPEI-25 polymers in HepG2 cells was favored by modification of about 9% to about 47% of the primary amine groups of bPEI-25 with cyclic carbonate monomer, represented by polymers A, B, F, G, S, T, H, I, R, U, K and P. Polymers C, L, M and N, which had more than 47% of the primary amine groups modified, produced large particles with low positive charges on the surface and had poor gene transfection efficiency. The cytotoxicity of gene complexes of the modified bPEI-25 polymers in HepG2 and HeLa cells was significantly less than the corresponding complex of the non-modified bPEI-25, and gene transfection efficiency was increased by as much as 2 fold in HepG2 cells (50% versus 25% for the non-modified bPEI-25). In addition, the mannose-modified polymers effectively delivered Bcl-2 siRNA into HeLa cells and downregulated Bcl-2 mRNA to one quarter of the normal level without apparent cytotoxicity. Such modified bPEI-25 polymers with various functionalities have great potential as vectors for targeted therapeutic gene delivery (e.g., mannose towards keratinocytes, macrophages and dendritic cells; galactose targeting liver cells).

Notably, transfection efficiency and cell viability were improved using only non-charged carbamate modifying groups. Further, none of the modified bPEI polymers contained a quaternary amine.

The modified branched polyethylenimine polymers can also be used as delivery vehicles for proteins and/or drugs.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A branched polyamine, comprising:
about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of formula (2):

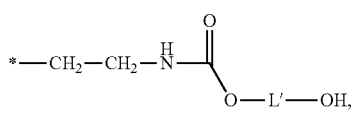

(2)

wherein:
(n'+q) is a number equal to about 45 to about 70,
the starred bond of formula (2) is linked to a backbone nitrogen of the branched polyamine,
L' is a divalent radical comprising 3 to 30 carbons, and
q/(n'+q)×100% equals about 9% to about 47%.

2. The branched polyamine of claim 1, wherein the branched polyamine consists essentially of n' primary ethylenimine repeat units, about 90 to about 140 secondary ethylenimine repeat units, about 45 to about 70 tertiary ethylenimine repeat units, and q carbamate groups of formula (2).

3. The branched polyamine of claim 1, wherein the branched polyamine is a carbamate functionalized branched polyethylenimine having a number average molecular weight of about 8500 to about 15000.

4. The branched polyamine of claim 1, wherein the branched polyamine is non-cytotoxic at N/P 10 to N/P 50.

5. The branched polyamine of claim 1, wherein L' comprises a sugar moiety.

6. The branched polyamine of claim 5, wherein the sugar moiety is a mannose, galactose, or glucose moiety.

7. The branched polyamine of claim 1, wherein q/(n'+q)×100% equals about 9% to about 25%.

8. The branched polyamine of claim 1, wherein q/(n'+q)×100% equals about 9% to about 12%.

9. The branched polyamine of claim 1, wherein the carbamate groups are not charged.

10. The branched polyamine of claim 1, wherein the branched polyamine has no quaternary amine groups.

11. The branched polyamine of claim 1, wherein the branched polyamine is capable of acting as a gene carrier in a process of gene transfection.

12. A branched polyamine, comprising:
about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of the formula (4):

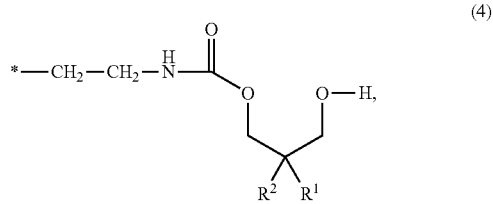

(4)

wherein
the starred bond of formula (4) is linked to a backbone nitrogen of the branched polyamine,
$R^1$ is hydrogen, methyl, or ethyl,
$R^2$ is hydrogen or a monovalent radical comprising 1 to 27 carbons,
(n'+q) is a number equal to about 45 to about 70, and
q/(n'+q)×100% equals about 9% to about 47%.

13. The branched polyamine of claim 12, wherein $R^2$ is an ester *—C(=O)O$R^3$, wherein $R^3$ comprises 1 to 26 carbons.

14. A method, comprising:
  treating a branched first polymer comprising about 45 to about 70 primary amine groups, a plurality of secondary amine groups, and a plurality of tertiary amine groups with a cyclic carbonate monomer without polymerizing the cyclic carbonate monomer, thereby forming a branched polyamine comprising i) about 45 to about 70 backbone tertiary amine groups, ii) about 90 to about 140 backbone secondary amine groups, iii) a positive number n' greater than 0 of backbone terminating primary amine groups, and iv) a positive number q greater than 0 of backbone terminating carbamate groups of formula (2):

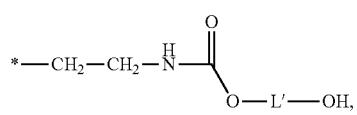

(2)

wherein:
  (n'+q) is a number equal to about 45 to about 70,
  the starred bond of formula (2) is linked to a backbone nitrogen of the branched polyamine,
  L' is a divalent radical comprising 3 to 30 carbons, and
  q/(n'+q)×100% equals about 9% to about 47%.

15. The method of claim 14, wherein the cyclic carbonate monomer comprises one or more protecting groups, and the method further comprises deprotecting the branched polyamine.

16. The method of claim 14, wherein the cyclic carbonate is a 6-membered ring cyclic carbonate.

17. The method of claim 14, wherein the branched first polymer is a branched polyethylenimine consisting essentially of:
  about 45 to about 70 primary ethylenimine repeat units having a structure

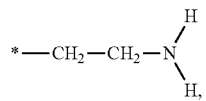

about 90 to about 140 secondary ethylenimine repeat units having a structure

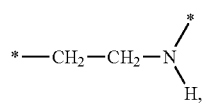

and
  about 45 to about 70 tertiary ethylenimine repeat units having a structure

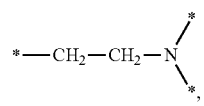

wherein each starred bond represents an attachment point to another repeat unit of the backbone.

18. The method of claim 14, wherein the cyclic carbonate monomer is selected from the group consisting of

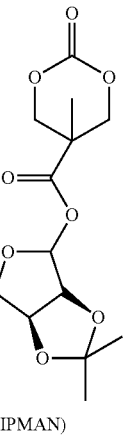

(MTC-IPMAN)

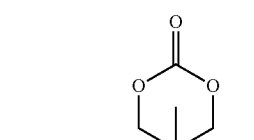

(MTC-IPGLU)

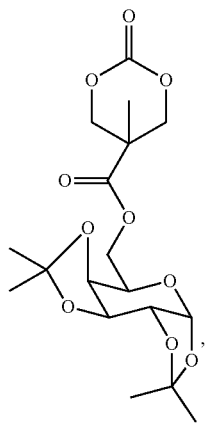

(MTC-IPGAL)

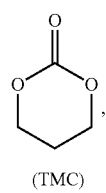

(TMC)

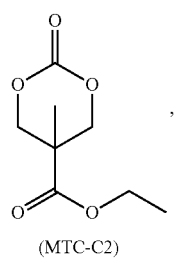

(MTC-C2)

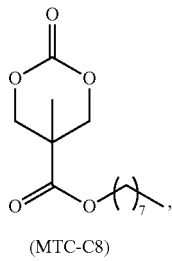

(MTC-C8)

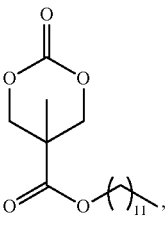

(MTC-C12)

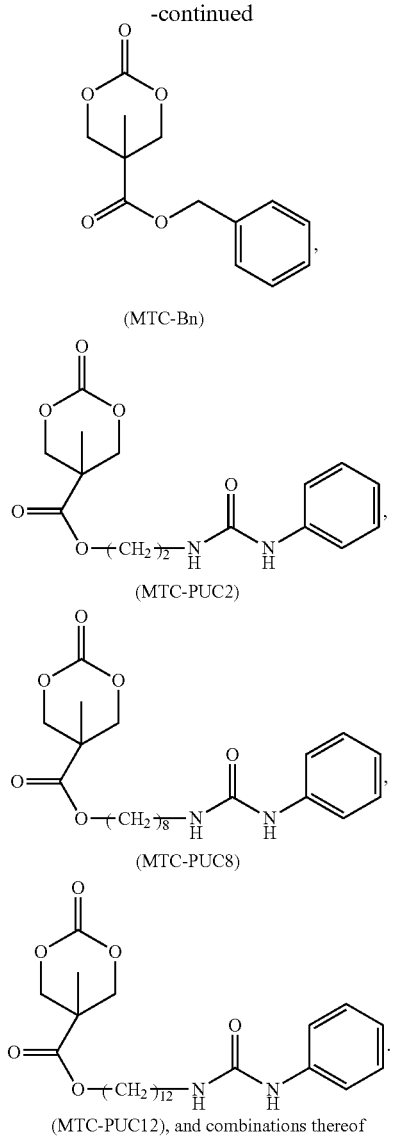

19. A complex comprising:
a gene; and
a branched polyamine comprising about 45 to about 70 backbone tertiary amine groups, about 90 to about 140 backbone secondary amine groups, a positive number n' greater than 0 of backbone terminating primary amine groups, and a positive number q greater than 0 of backbone terminating carbamate groups of formula (2):

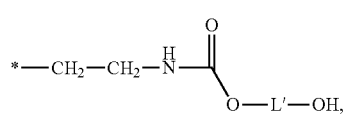

wherein:
(n'+q) is a number equal to about 45 to about 70,
the starred bond of formula (2) is linked to a backbone nitrogen of the branched polyamine,
L' is a divalent linking group comprising 3 to 30 carbons, and
q/(n'+q)×100% equals about 9% to about 47%.

20. The complex of claim 19, wherein the gene is siRNA.

21. A method of treating a cell, comprising contacting the cell with the complex of claim 19.

22. The method of claim 21, wherein the cell is a human tumor cell.

23. The method of claim 21, wherein the cell is a cancerous liver cell.

24. The method of claim 21, wherein the cell is a cancerous cervical cell.

25. The method of claim 21, wherein the cell is a cancerous ovarian cell.

26. The method of claim 21, wherein the cell is a human mesenchymal stem cell.

27. A branched polyamine having a structure according to formula (5):

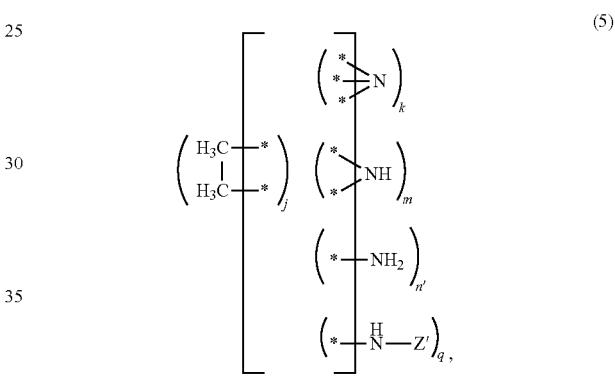

wherein j, k, m, n' and q represent molar amounts greater than 0, j has a value about 185 to about 280, k has a value of about 45 to about 70, m has a value of about 90 to about 140, (n'+q) has a value of about 45 to about 70, and q/(n'+q)×100% has a value of about 9% to about 47%, and each Z' is an independent moiety selected from the group consisting of

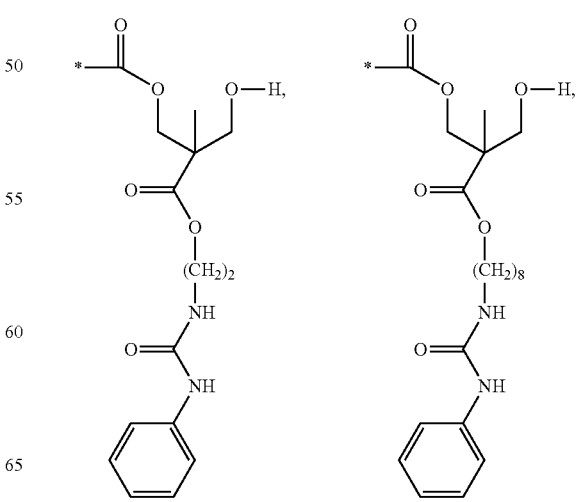

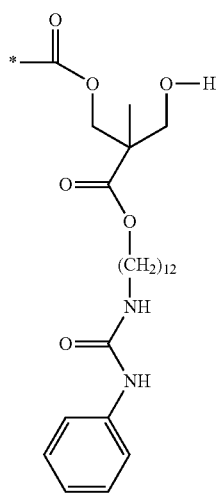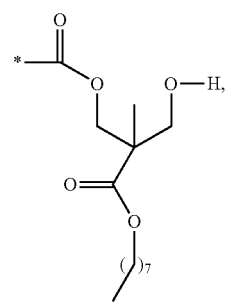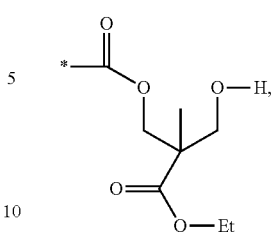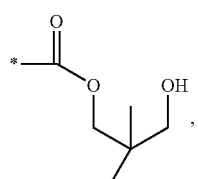
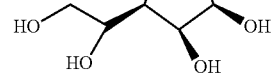
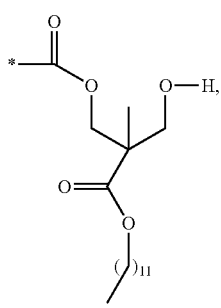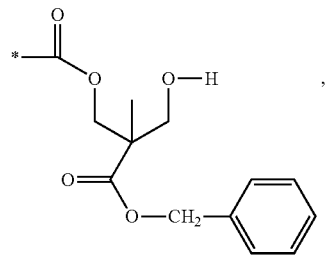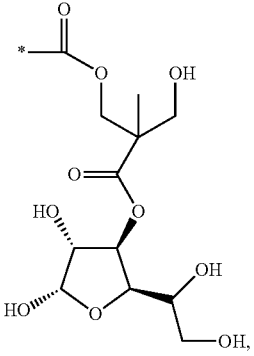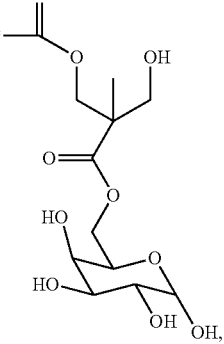
and combinations thereof.
* * * * *

SEQUENCE LISTING

<160> NUMBER OF SEQ ID NOS: 6

<210> SEQ ID NO 1
<211> LENGTH: 19
<212> TYPE: RNA
<213> ORGANISM: human

<400> SEQUENCE: 1
guacauccau uauaagcug                                                    19

<210> SEQ ID NO 2
<211> LENGTH: 19
<212> TYPE: RNA
<213> ORGANISM: human

<400> SEQUENCE: 2
cagcuuauaa uggauguac                                                    19

<210> SEQ ID NO 3
<211> LENGTH: 25
<212> TYPE: DNA
<213> ORGANISM: human

<400> SEQUENCE: 3

```
cgacgacttc tcccgccgct accgc                                        25

<210> SEQ ID NO 4
<211> LENGTH: 25
<212> TYPE: DNA
<213> ORGANISM: human

<400> SEQUENCE: 4
ccgcatgctg gggccgtaca gttcc                                        25

<210> SEQ ID NO 5
<211> LENGTH: 21
<212> TYPE: DNA
<213> ORGANISM: human

<400> SEQUENCE: 5
gctcgtcgtc gacaacggct c                                            21

<210> SEQ ID NO 6
<211> LENGTH: 25
<212> TYPE: DNA
<213> ORGANISM: human

<400> SEQUENCE: 6
caaacatgat ctgggtcatc ttctc                                        25
```